(12) United States Patent
Röhrig et al.

(10) Patent No.: US 9,765,070 B2
(45) Date of Patent: Sep. 19, 2017

(54) SUBSTITUTED OXOPYRIDINE DERIVATIVES

(71) Applicant: Bayer Pharma Aktiengesellschaft, Berlin (DE)

(72) Inventors: Susanne Röhrig, Hilden (DE); Alexander Hillisch, Solingen (DE); Julia Strassburger, Wuppertal (DE); Stefan Heitmeier, Wülfrath (DE); Martina Victoria Schmidt, Köln (DE); Karl-Heinz Schlemmer, Wuppertal (DE); Adrian Tersteegen, Wuppertal (DE); Anja Buchmüller, Essen (DE); Christoph Gerdes, Köln (DE); Martina Schäfer, Berlin (DE); Henrik Teller, Schwaan (DE); Eloisa Jimenez Nunez, Wuppertal (DE); Hartmut Schirok, Langenfeld (DE); Jürgen Klar, Wuppertal (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/032,212

(22) PCT Filed: Oct. 28, 2014

(86) PCT No.: PCT/EP2014/073132
§ 371 (c)(1),
(2) Date: Apr. 26, 2016

(87) PCT Pub. No.: WO2015/063093
PCT Pub. Date: May 7, 2015

(65) Prior Publication Data
US 2016/0272637 A1    Sep. 22, 2016

(30) Foreign Application Priority Data

Oct. 30, 2013  (EP) .................... 13190940
Sep. 24, 2014  (EP) .................... 14186078

(51) Int. Cl.
C07D 471/02   (2006.01)
A61K 31/44    (2006.01)
C07D 471/04   (2006.01)
A61K 31/437   (2006.01)
C07D 487/04   (2006.01)

(52) U.S. Cl.
CPC .......... *C07D 471/04* (2013.01); *A61K 31/437* (2013.01); *C07D 487/04* (2013.01)

(58) Field of Classification Search
CPC ... C07D 471/04; C07D 471/14; A61K 31/437
USPC .................. 546/118, 121; 514/303, 299, 301
See application file for complete search history.

(56) References Cited

FOREIGN PATENT DOCUMENTS

| GB | 2497806 A      | 6/2013 |
| WO | 02/042273 A2   | 5/2002 |
| WO | 2006/030032 A1 | 3/2006 |
| WO | 2008/079787 A2 | 7/2008 |

OTHER PUBLICATIONS

Baumgart et al. "inflammatory bowel disease: clinical aspect and established and evolving therapies," The Lancet, May 2007, vol. 369, Issue 9573, pp. 1641-1657.*
Bork "Diagnosis and Treatment of Hereditary angioedema with normal C1 inhibitor," Allergy, Asthma & Clinical Immunology, 2010, vol. 6, No. 15, pp. 1-8.*
Aponick, et al., "Chirality Transfer in Au-Catalyzed Cyclization Reactions of Monoallylic Diols: Selective Access to Specific Enantiomers Based on Olefin Geometry", Organic Letters, vol. 13, No. 6, 2011, pp. 1330-1333.
Castells, et al., "1-Alkoxycarbonylalkylidenetriphenylarsonanes: Preparation and Reactions", Tetrahedron, vol. 50, No. 48, 1994, pp. 13765-13774.
Fier, et al., "Synthesis of Difluoromethyl Ethers with Difluoromethyltriflate", Angew. Chem. Int. Ed., 52, 2013, 4 pages.
Ikemoto, et al., "A Practical Synthesis of the Chronic Renal Disease Agent, 4,5-Dihydro-3H-1,4,8b-triazaacenaphthylen-3-one Derivatives, Using Regioselective chlorination of Ethyl 5-mthylimidazo[1,2-a]pyridine-3-carboxylate with N-Chlorosuccinimide", Tetrahedron 56, 2000, pp. 7915-7921.
Kendall, et al., "Discovery of pyrazolo[1,5-a]pyridines as p110α-selective PI3 kinase inhibitors", Bioorganic and Medicinal Chemistry, 20, 2012, pp. 69-85.
Levin, et al., "Reaction of the Ruppert-Prakash reagent with perfluorosulfonic acids", Journal of Fluorine Chemistry, 130, 2009, pp. 667-670.
European Patent Office, Written Opinion for International Patent Application No. PCT/EP2014/073132, May 7, 2015, 4 pages.
European Patent Office, International Search Report (including English Translation) for International Patent Application No. PCT/EP2014/073132, Jan. 15, 2015, 6 pages.

* cited by examiner

*Primary Examiner* — Shengjun Wang
(74) *Attorney, Agent, or Firm* — Nixon & Vanderhye P.C.

(57) ABSTRACT

The invention relates to substituted oxopyridine derivatives and to processes for their preparation, and also to their use for preparing medicaments for the treatment and/or prophylaxis of diseases, in particular cardiovascular disorders, preferably thrombotic or thromboembolic disorders, and oedemas, and also ophthalmic disorders.

9 Claims, No Drawings

SUBSTITUTED OXOPYRIDINE DERIVATIVES

CROSS-REFERENCE TO RELATED APPLICATIONS

This application is a U.S. national phase application of International Patent Application No. PCT/EP2014/073132, filed Oct. 28, 2014 and titled SUBSTITUTED OXOPYRIDINE DERIVATIVES, which claims priority to both European Patent Application No. 13190940.0, filed Oct. 30, 2013, titled SUBSTITUTED OXOPYRIDINE DERIVATIVES, and European Patent Application No. 14186078.3, filed Sep. 24, 2014, titled SUBSTITUTED OXOPYRIDINE DERIVATIVES, the contents of each of which are incorporated herein by reference in their entirety.

The invention relates to substituted oxopyridine derivatives and to processes for their preparation, and also to their use for preparing medicaments for the treatment and/or prophylaxis of diseases, in particular cardiovascular disorders, preferably thrombotic or thromboembolic disorders, and oedemas, and also ophthalmic disorders.

Blood coagulation is a protective mechanism of the organism which helps to "seal" defects in the wall of the blood vessels quickly and reliably. Thus, loss of blood can be avoided or kept to a minimum. Haemostasis after injury of the blood vessels is effected mainly by the coagulation system in which an enzymatic cascade of complex reactions of plasma proteins is triggered. Numerous blood coagulation factors are involved in this process, each of which factors converts, on activation, the respectively next inactive precursor into its active form. At the end of the cascade comes the conversion of soluble fibrinogen into insoluble fibrin, resulting in the formation of a blood clot. In blood coagulation, traditionally the intrinsic and the extrinsic system, which end in a final joint reaction path, are distinguished. Here, factors Xa and IIa (thrombin) play key roles: Factor Xa bundles the signals of the two coagulation paths since it is formed both via factor VIIa/tissue factor (extrinsic path) and via the tenase complex (intrinsic path) by conversion of factor X. The activated serine protease Xa cleaves prothrombin to thrombin which, via a series of reactions, transduces the impulses from the cascade to the coagulation state of the blood.

In the more recent past, the traditional theory of two separate regions of the coagulation cascade (extrinsic and intrinsic path) has been modified owing to new findings: In these models, coagulation is initiated by binding of activated factor VIIa to tissue factor (TF). The resulting complex activates factor X, which in turn leads to generation of thrombin with subsequent production of fibrin and platelet activation (via PAR-1) as injury-sealing end products of haemostasis. Compared to the subsequent amplification/propagation phase, the thrombin production rate in this first phase is low and as a result of the occurrence of TFPI as inhibitor of the TF-FVIIa-FX complex is limited in time.

A central component of the transition from initiation to amplification and propagation of coagulation is factor XIa: in positive feedback loops, thrombin activates, in addition to factor V and factor VIII, also factor XI to factor XIa, whereby factor IX is converted into factor IXa, and, via the factor IXa/factor VIIIa complex generated in this manner, the factor X is activated and thrombin formation is in turn therefore highly stimulated leading to strong thrombus growth and stabilizing the thrombus.

In addition, it becomes the focus that, in addition to the stimulation via tissue factor, the coagulation system can be activated particularly on negatively charged surfaces, which include not only surface structures of foreign cells (e.g. bacteria) but also artificial surfaces such as vascular prostheses, stents and extracoporeal circulation. On the surface, initially factor XII (FXII) is activated to factor XIIa which subsequently activates factor XI, attached to cell surfaces, to factor XIa. This leads to further activation of the coagulation cascade as described above. In addition, factor XIIa also activates bound plasma prokallikrein to plasma kallikrein (PK) which, in a potentiation loop, firstly leads to further factor XII activation, overall resulting in amplification of the initiation of the coagulation cascade. In addition, PK is an important bradikinin-releasing protease which, inter alia, thus leads to increased endothelial permeability. Further substrates that have been described are prorenin and prourokinase, whose activation may influence the regulatory processes of the renin-angiotensin system and fibrinolysis. The activation of PK is therefore an important link between coagulative and inflammatory processes.

Uncontrolled activation of the coagulation system or defective inhibition of the activation processes may lead to the formation of local thromboses or embolisms in vessels (arteries, veins, lymph vessels) or cardiac cavities. In addition, systemic hypercoagulability may lead to system-wide formation of thrombi and finally to consumption coagulopathy in the context of a disseminated intravasal coagulation. Thromboembolic complications may also occur in extracorporeal circulatory systems such as during haemodialysis and also in vascular prostheses or prosthetic heart valves and stents.

In the course of many cardiovascular and metabolic disorders, there is an increased tendency for coagulation and platelet activation owing to systemic factors such as hyperlipidaemia, diabetes or smoking, owing to changes in blood flow with stasis, for example in atrial fibrillation, or owing to pathological changes in vessel walls, for example endothelial dysfunctions or atherosclerosis. This unwanted and excessive activation of coagulation may, by formation of fibrin- and platelet-rich thrombi, lead to thromboembolic disorders and thrombotic complications with life-threatening conditions. Inflammable processes may also be involved here. Accordingly, thromboembolic disorders are still one of the most frequent causes of morbidity and mortality in most industrialized countries.

The anticoagulants known from the prior art, that is to say substances for inhibiting or preventing blood coagulation, have various disadvantages. Accordingly, in practice, efficient treatment methods or the prophylaxis of thrombotic/thromboembolic disorders is found to be very difficult and unsatisfactory.

In the therapy and prophylaxis of thromboembolic disorders, use is made, firstly, of heparin which is administered parenterally or subcutaneously. Because of more favourable pharmacokinetic properties, preference is these days increasingly given to low-molecular-weight heparin; however, the known disadvantages described hereinbelow encountered in heparin therapy cannot be avoided either in this manner. Thus, heparin is orally ineffective and has only a comparatively short half-life. In addition, there is a high risk of bleeding, there may in particular be cerebral haemorrhages and bleeding in the gastrointestinal tract, and there may be thrombopaenia, alopecia medicomentosa or osteoporosis. Low-molecular-weight heparins do have a lower probability of leading to the development of heparin-induced thrombocytopaenia; however, they can also only be administered subcutaneously. This also applies to fondaparinux, a synthetically produced selective factor Xa inhibitor having a long half-life.

A second class of anticoagulants are the vitamin K antagonists. These include, for example, 1,3-indanediones and in particular compounds such as warfarin, phenprocoumon, dicumarol and other coumarin derivatives which non-selectively inhibit the synthesis of various products of certain vitamin K-dependent coagulation factors in the liver. Owing to the mechanism of action, the onset of action is only very slow (latency to the onset of action 36 to 48 hours). The compounds can be administered orally; however, owing to the high risk of bleeding and the narrow therapeutic index complicated individual adjustment and monitoring of the patient are required. In addition, other side-effects such as gastrointestinal problems, hair loss and skin necroses have been described.

More recent approaches for oral anticoagulants are in various phases of clinical evaluation or in clinical use, and have demonstrated their effectiveness in various studies. However, taking these medicaments can also lead to bleeding complications, particularly in predisposed patients. Thus, for antithrombotic medicaments, the therapeutic window is of central importance: The interval between the therapeutically active dose for coagulation inhibition and the dose where bleeding may occur should be as large as possible so that maximum therapeutic activity is achieved at a minimum risk profile.

In various in vitro and in vivo models with, for example, antibodies as factor XIa inhibitors, but also in factor XIa knock-out models, the antithrombotic effect with small/no prolongation of bleeding time or extension of blood volume was confirmed. In clinical studies, elevated factor XIa concentrations were associated with an increased event rate. In contrast, factor XI deficiency (haemophilia C) did not lead to spontaneous bleeding and was apparent only in the course of surgical operations and traumata, but did show protection with respect to certain thromboembolic events.

In addition, plasma kallikrein (PK) is associated with other disorders, which are associated with increased vascular permeability or chronic inflammatory disorders such as is the case in diabetic retinopathy, macular oedema and hereditary angiooedema or chronic inflammatory intestinal disorders. Diabetic retinopathy is primarily caused by microvascular deficiency, which leads to basal membrane thickening of the vessels and loss of vascularized pericytes followed by vascular occlusion and retinal ischaemia which, owing to the retinal hypoxia thus caused, may lead to enhanced vessel permeability with subsequent formation of a macular oedema and, due to all of the processes present, to the patient going blind. In hereditary angiooedema (HAE), reduced formation of the physiological kallikrein inhibitor C1-esterase inhibitor causes uncontrolled plasma kallikrein activation leading to inflammations with fulminant oedema formation and strong pains. From experimental animal models, there are indications that inhibition of plasma kallikrein inhibits increased vascular permeability and may therefore prevent formation of a macular oedema and/or diabetic retinopathy or may improve the acute symptoms of HAE. Oral plasma kallikrein inhibitors could also be used for prophylaxis of HAE.

The kinins generated by means of plasma kallikrein especially have a causative role in the progression of chronic inflammatory intestinal disorders (CID). Their pro-inflammatory effect via activation of bradykinin receptors induces and potentiates the disease progression. Studies on Crohn's disease patients show a correlation between the kallikrein concentration in the intestinal epithelium and the degree of intestinal inflammation. Activation of the kallikrein-kinin system was likewise observed in experimental animal studies. Inhibition of bradykinin synthesis by kallikrein inhibitors could accordingly be used also for prophylaxis and/or therapy of chronic inflammatory intestinal disorders.

Furthermore, for many disorders the combination of anti-thrombotic and antiinflammatory principles may also be particularly attractive to prevent the mutual enhancement of coagulation and inflammation.

It is therefore an object of the present invention to provide novel compounds for the treatment of cardiovascular disorders, in particular of thrombotic or thromboembolic disorders, and/or oedematous disorders, and/or ophthalmic disorders, in particular diabetic retinopathy and/or macular oedema, in humans and animals, which compounds have a wide therapeutic bandwidth.

WO 2006/030032 describes inter alia substituted pyridinones as allosteric modulators of the mGluR2 receptor, and WO 2008/079787 describes substituted pyridin-2-ones and their use as glucokinase activators.

The invention provides compounds of the formula

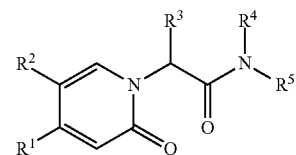

(I)

in which
R$^1$ represents a group of the formula

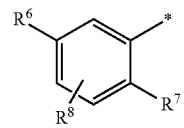

where * is the point of attachment to the oxopyridine ring,
R$^6$ represents bromine, chlorine, fluorine, methyl, difluoromethyl, trifluoromethyl, methoxy, difluoromethoxy or trifluoromethoxy,
R$^7$ represents bromine, chlorine, fluorine, cyano, nitro, hydroxy, methyl, difluoromethyl, trifluoromethyl, methoxy, ethoxy, difluoromethoxy, trifluoromethoxy, ethynyl, 3,3,3-trifluoroprop-1-yn-1-yl or cyclopropyl,
R$^8$ represents hydrogen, chlorine or fluorine,
R$^2$ represents hydrogen, bromine, chlorine, fluorine, cyano, C$_1$-C$_3$-alkyl, difluoromethyl, trifluoromethyl, 1,1-difluoroethyl, 2,2-difluoroethyl, 2,2,2-trifluoroethyl, C$_1$-C$_3$-alkoxy, difluoromethoxy, trifluoromethoxy, 1,1-difluoroethoxy, 2,2-difluoroethoxy, 2,2,2-trifluoroethoxy, hydroxycarbonyl, methylcarbonyl or cyclopropyl,
R$^3$ represents hydrogen, C$_1$-C$_5$-alkyl, C$_1$-C$_4$-alkoxy, difluoromethyl, trifluoromethyl, 1,1-difluoroethyl, 3,3,3-trifluoro-2-hydroxyprop-1-yl, 3,3,3-trifluoro-2-methoxyprop-1-yl, 3,3,3-trifluoro-2-ethoxyprop-1-yl, prop-2-yn-1-yl, cyclopropyloxy or cyclobutyloxy,
where alkyl may be substituted by a substituent selected from the group consisting of fluorine, cyano, hydroxy, difluoromethyl, trifluoromethyl, methoxy, ethoxy, difluoromethoxy, trifluoromethoxy, C$_3$-C$_6$-cycloalkyl, 4- to 6-membered oxoheterocyclyl, 1,4-dioxanyl, oxazolyl, phenyl and pyridyl,
where cycloalkyl may be substituted by 1 to 2 substituents independently of one another selected from the group consisting of fluorine, hydroxy, methyl, ethyl, methoxy, ethoxy, difluoromethyl, trifluoromethyl, difluoromethoxy and trifluoromethoxy, $R^4$ represents hydrogen,
$R^5$ represents a group of the formula

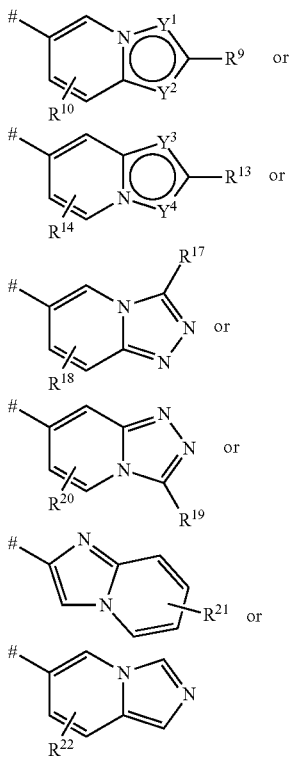

where # is the point of attachment to the nitrogen atom,
$Y^1$ represents a nitrogen atom or C—$R^{11}$,
where
$R^{11}$ represents hydrogen, chlorine, hydroxy, methoxy or $C_1$-$C_3$-alkoxycarbonyl,
$Y^2$ represents a nitrogen atom or C—$R^{12}$,
where
$R^{12}$ represents hydrogen, chlorine, hydroxy or methoxy,
$R^9$ represents hydrogen, hydroxycarbonyl, hydroxycarbonylmethyl or phenyl,
where phenyl may be substituted by 1 to 2 fluorine substituents,
$R^{10}$ represents hydrogen, chlorine, fluorine or methyl,
$Y^3$ represents a nitrogen atom or C—$R^{15}$,
where
$R^{15}$ represents hydrogen, chlorine, hydroxy or methoxy,
$Y^4$ represents a nitrogen atom or C—$R^{16}$,
where
$R^{16}$ represents hydrogen, chlorine, hydroxy or methoxy,
$R^{13}$ represents hydrogen, hydroxycarbonyl, hydroxycarbonylmethyl, $C_1$-$C_3$-alkoxycarbonyl or aminocarbonyl,
$R^{14}$ represents hydrogen, chlorine, fluorine or methyl,
$R^{17}$ represents hydrogen, chlorine, hydroxy, $C_1$-$C_4$-alkyl, methoxy, $C_1$-$C_3$-alkylaminomethyl or morpholinylmethyl,
$R^{18}$ represents hydrogen, chlorine, fluorine or methyl,
$R^{19}$ represents hydrogen, chlorine, hydroxy or methoxy,
$R^{20}$ represents hydrogen, chlorine, fluorine or methyl,
$R^{21}$ represents hydrogen, hydroxycarbonyl or hydroxycarbonylmethyl,
$R^{22}$ represents hydrogen, chlorine, fluorine or methyl,
and the salts thereof, the solvates thereof and the solvates of the salts thereof.

Compounds according to the invention are the compounds of the formula (I) and the salts, solvates and solvates of the salts thereof, and also the compounds encompassed by formula (I) and specified hereinafter as working example(s), and the salts, solvates and solvates of the salts thereof, to the extent that the compounds encompassed by formula (I) and specified hereinafter are not already salts, solvates and solvates of the salts.

The compounds of the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. The stereoisomerically uniform constituents can be isolated from such mixtures of enantiomers and/or diastereomers in a known manner; chromatography processes are preferably used for this, especially HPLC chromatography on an achiral or chiral phase.

If the compounds according to the invention can occur in tautomeric forms, the present invention encompasses all the tautomeric forms.

The present invention also encompasses all suitable isotopic variants of the compounds of the invention. An isotopic variant of a compound of the invention is understood here to mean a compound in which at least one atom within the compound of the invention has been exchanged for another atom of the same atomic number, but with a different atomic mass from the atomic mass which usually or predominantly occurs in nature. Examples of isotopes which can be incorporated into a compound of the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I an $^{131}$I. Particular isotopic variants of a compound of the invention, especially those in which one or more radioactive isotopes have been incorporated, may be beneficial, for example, for the examination of the mechanism of action or of the active ingredient distribution in the body; due to comparatively easy preparability and detectability, especially compounds labelled with $^3$H or $^{14}$C isotopes are suitable for this purpose. In addition, the incorporation of isotopes, for example of deuterium, may lead to particular therapeutic benefits as a consequence of greater metabolic stability of the compound, for example an extension of the half-life in the body or a reduction in the active dose required; such modifications of the compounds of the invention may therefore in some cases also constitute a preferred embodiment of the present invention. Isotopic variants of the compounds of the invention can be prepared by the processes known to those skilled in the art, for example by the methods described further down and the procedures described in the working examples, by using corresponding isotopic modifications of the respective reagents and/or starting compounds.

Preferred salts in the context of the present invention are physiologically acceptable salts of the compounds according to the invention. However, the invention also encompasses salts which themselves are unsuitable for pharmaceutical applications but which can be used, for example, for the isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

Solvates in the context of the invention are described as those forms of the compounds according to the invention which form a complex in the solid or liquid state by coordination with solvent molecules. Hydrates are a specific form of the solvates in which the coordination is with water.

The present invention additionally also encompasses prodrugs of the compounds of the invention. The term "prodrugs" encompasses compounds which for their part may be biologically active or inactive but are converted during their residence time in the body into compounds according to the invention (for example by metabolism or hydrolysis).

The two ways (A) and (B) of representing a 1,4-disubstituted cyclohexyl derivative shown below are equivalent to one another and identical, and in both cases describe a trans-1,4-disubstituted cyclohexyl derivative.

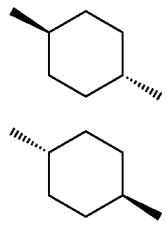

(A)

(B)

This applies in particular to the structural element of (trans-4-hydroxycyclohexyl)methyl in 3-(trans-4-hydroxycyclohexyl)propanamide.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is used here synonymously with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

In the context of the present invention, unless specified otherwise, the substituents are defined as follows:

Alkyl represents a straight-chain or branched alkyl radical having 1 to 5 carbon atoms, preferably 1 to 3 carbon atoms, by way of example and with preference methyl, ethyl, n-propyl, isopropyl, 2-methylprop-1-yl, n-butyl, tert-butyl and 2,2-dimethylprop-1-yl.

Alkoxy represents a straight-chain or branched alkoxy radical having 1 to 4 carbon atoms, preferably 1 to 3 carbon atoms, by way of example and with preference methoxy, ethoxy, n-propoxy, isopropoxy, 2-methylprop-1-oxy, n-butoxy and tert-butoxy.

Alkoxycarbonyl represents a straight-chain or branched alkoxy radical attached via a carbonyl group and having 1 to 3 carbon atoms, preferably 1 to 2 carbon atoms, for example and with preference methoxycarbonyl, ethoxycarbonyl, n-propoxycarbonyl and isopropoxycarbonyl.

Alkylaminomethyl represents an amino group having one or two independently selected, identical or different, straight-chain or branched alkyl substituents each having 1 to 3 carbon atoms, attached via a methyl group, for example and with preference methylaminomethyl, ethylaminomethyl, n-propylaminomethyl, isopropylaminomethyl, N,N-dimethylaminomethyl, N,N-diethylaminomethyl, N-ethyl-N-methylaminomethyl, N-methyl-N-n-propylaminomethyl, N-isopropyl-N-n-propylaminomethyl and N,N-diisopropylaminomethyl. $C_1$-$C_3$-Alkylaminomethyl represents, for example, a monoalkylaminomethyl radical having 1 to 3 carbon atoms or a dialkylaminomethyl radical having in each case 1 to 3 carbon atoms in each alkyl substituent.

Cycloalkyl represents a monocyclic cycloalkyl group having 3 to 6 carbon atoms, preferred examples of cycloalkyl being cyclopropyl, cyclobutyl, cyclopentyl and cyclohexyl.

4- to 6-membered oxoheterocyclyl in the definition of the radical $R^3$ represents a saturated monocyclic radical having 4 to 6 ring atoms in which one ring atom is an oxygen atom, by way of example and with preference oxetanyl, tetrahydrofuranyl and tetrahydro-2H-pyranyl.

In the formulae of the group which may represent $R^1$, the end point of the line marked by * in each case does not represent a carbon atom or a $CH_2$ group, but is part of the bond to the atom to which $R^1$ is attached.

In the formulae of the group which may represent $R^5$, the end point of the line marked by # in each case does not represent a carbon atom or a $CH_2$ group, but is part of the bond to the atom to which $R^5$ is attached.

Preference is given to compounds of the formula (I) in which $R^1$ represents a group of the formula

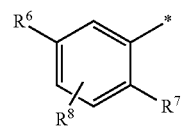

where * is the point of attachment to the oxopyridine ring,
$R^6$ represents bromine, chlorine, fluorine, methyl, difluoromethyl, trifluoromethyl, methoxy, difluoromethoxy or trifluoromethoxy,
$R^7$ represents bromine, chlorine, fluorine, cyano, nitro, hydroxy, methyl, difluoromethyl, trifluoromethyl, methoxy, ethoxy, difluoromethoxy, trifluoromethoxy, ethynyl, 3,3,3-trifluoroprop-1-yn-1-yl or cyclopropyl,
$R^8$ represents hydrogen, chlorine or fluorine,
$R^2$ represents hydrogen, bromine, chlorine, fluorine, cyano, $C_1$-$C_3$-alkyl, difluoromethyl, trifluoromethyl, 1,1-difluoroethyl, 2,2-difluoroethyl, 2,2,2-trifluoroethyl, $C_1$-$C_3$-alkoxy, difluoromethoxy, trifluoromethoxy, 1,1-difluoroethoxy, 2,2-difluoroethoxy, 2,2,2-trifluoroethoxy, methylcarbonyl or cyclopropyl,
$R^3$ represents hydrogen, $C_1$-$C_5$-alkyl, $C_1$-$C_4$-alkoxy, difluoromethyl, trifluoromethyl, 1,1-difluoroethyl, 3,3,3-trifluoro-2-hydroxyprop-1-yl, 3,3,3-trifluoro-2-methoxyprop-1-yl, 3,3,3-trifluoro-2-ethoxyprop-1-yl, prop-2-yn-1-yl, cyclopropyloxy or cyclobutyloxy,
where alkyl may be substituted by a substituent selected from the group consisting of fluorine, cyano, hydroxy, difluoromethyl, trifluoromethyl, methoxy, ethoxy, difluoromethoxy, trifluoromethoxy, $C_3$-$C_6$-cycloalkyl, 4- to 6-membered oxoheterocyclyl, 1,4-dioxanyl, phenyl and pyridyl,
where cycloalkyl may be substituted by 1 to 2 substituents independently of one another selected from the group consisting of fluorine, hydroxy, methyl, ethyl, methoxy, ethoxy, difluoromethyl, trifluoromethyl, difluoromethoxy and trifluoromethoxy,
$R^4$ represents hydrogen,
$R^5$ represents a group of the formula

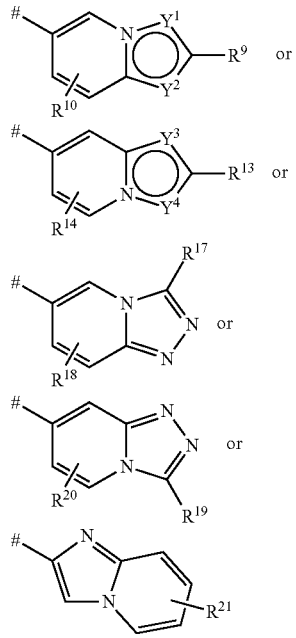

where # is the point of attachment to the nitrogen atom,
$Y^1$ represents a nitrogen atom or C—$R^{11}$,
where
$R^{11}$ represents hydrogen, chlorine, hydroxy or methoxy,
$Y^2$ represents a nitrogen atom or C—$R^{12}$,
where
$R^{12}$ represents hydrogen, chlorine, hydroxy or methoxy,
$R^9$ represents hydrogen, hydroxycarbonyl or hydroxycarbonylmethyl,
$R^{10}$ represents hydrogen, chlorine, fluorine or methyl,
$Y^3$ represents a nitrogen atom or C—$R^{15}$,
where
$R^{15}$ represents hydrogen, chlorine, hydroxy or methoxy,
$Y^4$ represents a nitrogen atom or C—$R^{16}$,
where
$R^{16}$ represents hydrogen, chlorine, hydroxy or methoxy,
$R^{13}$ represents hydrogen, hydroxycarbonyl or hydroxycarbonylmethyl,
$R^{14}$ represents hydrogen, chlorine, fluorine or methyl,
$R^{17}$ represents hydrogen, chlorine, hydroxy or methoxy,
$R^{18}$ represents hydrogen, chlorine, fluorine or methyl,
$R^{19}$ represents hydrogen, chlorine, hydroxy or methoxy,
$R^{20}$ represents hydrogen, chlorine, fluorine or methyl,
$R^{21}$ represents hydrogen, hydroxycarbonyl or hydroxycarbonylmethyl,
and the salts thereof, the solvates thereof and the solvates of the salts thereof.

Preference is also given to compounds of the formula (I) in which
$R^1$ represents a group of the formula

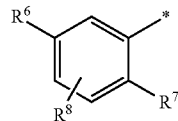

where * is the point of attachment to the oxopyridine ring,
$R^6$ represents chlorine,
$R^7$ represents cyano, difluoromethyl, trifluoromethyl, difluoromethoxy or trifluoromethoxy,
$R^8$ represents hydrogen,
$R^2$ represents chlorine, cyano, methoxy, ethoxy or difluoromethoxy,
$R^3$ represents hydrogen, methyl, ethyl, n-propyl, 2-methylprop-1-yl, n-butyl or ethoxy,
where methyl may be substituted by a substituent selected from the group consisting of difluoromethyl, trifluoromethyl, cyclopropyl, cyclobutyl, cyclohexyl, oxetanyl, tetrahydrofuranyl, tetrahydro-2H-pyranyl and 1,4-dioxanyl,
where cyclopropyl, cyclobutyl, cyclohexyl and oxetanyl may be substituted by 1 to 2 substituents independently of one another selected from the group consisting of fluorine, hydroxy, methyl, ethyl and methoxy,
and
where ethyl, n-propyl and n-butyl may be substituted by a substituent selected from the group consisting of fluorine, methoxy and trifluoromethoxy,
$R^4$ represents hydrogen,
$R^5$ represents a group of the formula

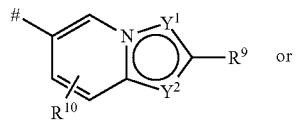

-continued

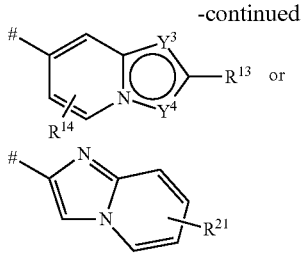

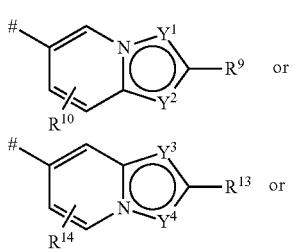

where # is the point of attachment to the nitrogen atom,
$Y^1$ represents a nitrogen atom or $C-R^{11}$,
where
$R^{11}$ represents hydrogen, chlorine, hydroxy or methoxy,
$Y^2$ represents a nitrogen atom or $C-R^{12}$,
where
$R^{12}$ represents hydrogen, chlorine, hydroxy or methoxy,
$R^9$ represents hydrogen or hydroxycarbonyl,
$R^{10}$ represents hydrogen or fluorine,
$Y^3$ represents a nitrogen atom or $C-R^{15}$,
where
$R^{15}$ represents hydrogen, chlorine, hydroxy or methoxy,
$Y^4$ represents a nitrogen atom or $C-R^{16}$,
where
$R^{16}$ represents hydrogen, chlorine, hydroxy or methoxy,
$R^{13}$ represents hydrogen or hydroxycarbonyl,
$R^{14}$ represents hydrogen or fluorine,
$R^{21}$ represents hydrogen or hydroxycarbonyl,
and the salts thereof, the solvates thereof and the solvates of the salts thereof.

Preference is also given to compounds of the formula (I) in which
$R^1$ represents a group of the formula

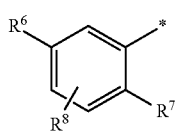

where * is the point of attachment to the oxopyridine ring,
$R^6$ represents chlorine,
$R^7$ represents cyano or difluoromethoxy,
$R^8$ represents hydrogen,
$R^2$ represents methoxy,
$R^3$ represents hydrogen, methyl or ethyl,
where methyl may be substituted by a cyclobutyl substituent,
$R^4$ represents hydrogen,
$R^5$ represents a group of the formula

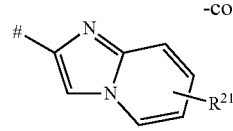

-continued where # is the point of attachment to the nitrogen atom,
$Y^1$ represents $C-R^{11}$,
where
$R^{11}$ represents hydrogen,
$Y^2$ represents a nitrogen atom,
$R^9$ represents hydrogen or hydroxycarbonyl,
$R^{10}$ represents hydrogen,
$Y^3$ represents a nitrogen atom,
$Y^4$ represents $C-R^{16}$,
where
$R^{16}$ represents hydrogen,
$R^{13}$ represents hydroxycarbonyl,
$R^{14}$ represents hydrogen,
$R^{21}$ represents hydroxycarbonyl,
and the salts thereof, the solvates thereof and the solvates of the salts thereof.

Preference is also given to compounds of the formula (I) in which
$R^1$ represents a group of the formula

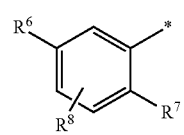

where * is the point of attachment to the oxopyridine ring,
$R^6$ represents chlorine,
$R^7$ represents cyano or difluoromethoxy,
$R^8$ represents hydrogen,
$R^2$ represents methoxy,
$R^3$ represents methyl or ethyl
where methyl may be substituted by a substituent selected from the group consisting of cyclobutyl and tetrahydro-2H-pyranyl,
and
where ethyl may be substituted by a methoxy substituent,
$R^4$ represents hydrogen,
$R^5$ represents a group of the formula

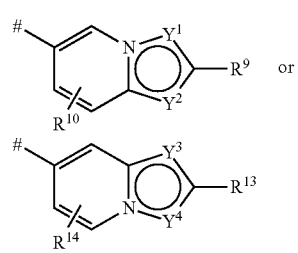

where # is the point of attachment to the nitrogen atom,
$Y^1$ represents $C-R^{11}$,
where
$R^{11}$ represents hydrogen or chlorine,
$Y^2$ represents a nitrogen atom,
$R^9$ represents hydrogen or hydroxycarbonyl,
$R^{10}$ represents hydrogen, Y³ represents a nitrogen atom,
and
Y⁴ represents C—R¹⁶,
where
R¹⁶ represents hydrogen,
or
Y³ represents C—R¹⁵,
where
R¹⁵ represents hydrogen or chlorine,
and
Y⁴ represents a nitrogen atom,
R¹³ represents hydrogen or hydroxycarbonyl,
R¹⁴ represents hydrogen,
and the salts thereof, the solvates thereof and the solvates of the salts thereof.

Preference is also given to compounds of the formula (I) in which
R¹ represents a group of the formula

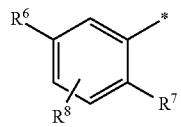

where * is the point of attachment to the oxopyridine ring,
R⁶ represents chlorine,
R⁷ represents cyano or difluoromethoxy,
R⁸ represents hydrogen.

Preference is also given to compounds of the formula (I) in which R² represents chlorine, cyano, methoxy, ethoxy or difluoromethoxy.

Preference is also given to compounds of the formula (I) in which R² represents methoxy.

Preference is also given to compounds of the formula (I) in which
R³ represents methyl, ethyl, n-propyl, 2-methylprop-1-yl, n-butyl or ethoxy,
where methyl may be substituted by a substituent selected from the group consisting of difluoromethyl, trifluoromethyl, cyclopropyl, cyclobutyl, cyclohexyl, oxetanyl, tetrahydrofuranyl, tetrahydro-2H-pyranyl and 1,4-dioxanyl,
where cyclopropyl, cyclobutyl, cyclohexyl and oxetanyl may be substituted by 1 to 2 substituents independently of one another selected from the group consisting of fluorine, hydroxy, methyl, ethyl and methoxy,
and
where ethyl, n-propyl and n-butyl may be substituted by a substituent selected from the group consisting of fluorine, methoxy and trifluoromethoxy.

Preference is also given to compounds of the formula (I) in which
R³ represents methyl or ethyl
where methyl may be substituted by a substituent selected from the group consisting of cyclobutyl and tetrahydro-2H-pyranyl,
and
where ethyl may be substituted by a methoxy substituent.

Preference is also given to compounds of the formula (I) in which
R³ represents hydrogen, methyl or ethyl,
where methyl may be substituted by a cyclobutyl substituent.

Preference is also given to compounds of the formula (I) in which
R³ represents methyl or ethyl
where methyl may be substituted by a cyclobutyl substituent.

Preference is also given to compounds of the formula (I) in which
R⁵ represents a group of the formula

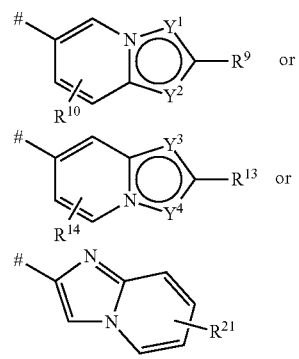

where # is the point of attachment to the nitrogen atom,
Y¹ represents C—R¹¹,
where
R¹¹ represents hydrogen,
Y² represents a nitrogen atom,
R⁹ represents hydrogen or hydroxycarbonyl,
R¹⁰ represents hydrogen,
Y³ represents a nitrogen atom,
Y⁴ represents C—R¹⁶,
where
R¹⁶ represents hydrogen,
R¹³ represents hydroxycarbonyl,
R¹⁴ represents hydrogen,
R²¹ represents hydroxycarbonyl.

Preference is also given to compounds of the formula (I) in which
R⁵ represents a group of the formula

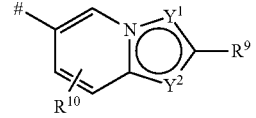

where # is the point of attachment to the nitrogen atom,
Y¹ represents C—R¹¹,
where
R¹¹ represents hydrogen,
Y² represents a nitrogen atom,
R⁹ represents hydrogen or hydroxycarbonyl,
R¹⁰ represents hydrogen.

Preference is also given to compounds of the formula (I) in which
R⁵ represents a group of the formula

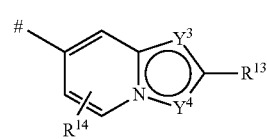

where # is the point of attachment to the nitrogen atom, $Y^3$ represents a nitrogen atom,
and
$Y^4$ represents C—$R^{16}$,
where
$R^{16}$ represents hydrogen,
or
$Y^3$ represents C—$R^{15}$,
where
$R^{15}$ represents hydrogen or chlorine,
and
$Y^4$ represents a nitrogen atom,
$R^{13}$ represents hydrogen or hydroxycarbonyl,
$R^{14}$ represents hydrogen.

Preference is also given to compounds of the formula (I) in which
$R^5$ represents a group of the formula

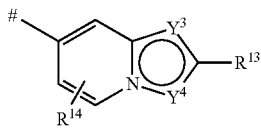

where # is the point of attachment to the nitrogen atom,
$Y^3$ represents C—$R^{15}$,
where
$R^{15}$ represents hydrogen,
$Y^4$ represents a nitrogen atom,
$R^{13}$ represents hydrogen,
$R^{14}$ represents hydrogen.

Preference is also given to compounds of the formula (I) in which $R^{13}$ represents hydrogen or hydroxycarbonyl.

Preference is also given to compounds of the formula (Ia)

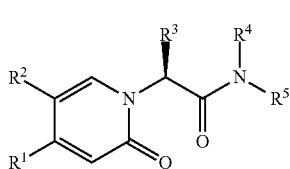 (Ia)

in which $R^1$, $R^2$, $R^3$, $R^4$ and $R^5$ are as defined above.

The invention further provides a process for preparing the compounds of the formula (I), or the salts thereof, solvates thereof or the solvates of the salts thereof, wherein

[A] the compounds of the formula

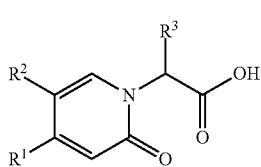 (II)

in which
$R^1$, $R^2$ and $R^3$ have the meaning given above
are in the first step reacted with compounds of the formula

 (III)

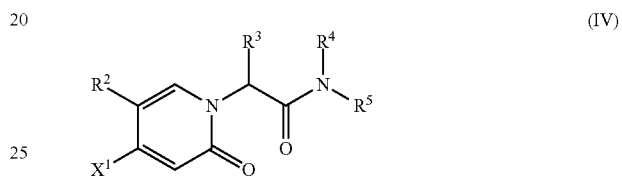

in which
$R^4$ and $R^5$ have the meaning given above,
in the presence of a dehydrating agent, and
optionally in a second step converted by acidic or basic ester hydrolysis into compounds of the formula (I),
or
[B] the compounds of the formula

 (IV)

in which
$R^2$, $R^3$, $R^4$ and $R^5$ have the meaning given above and
$X^1$ represents chlorine, bromine or iodine,
are reacted with compounds of the formula $R^1$-Q    (V)

in which
$R^1$ is as defined above, and
Q represents —B(OH)$_2$, a boronic ester, preferably boronic acid pinacol ester, or —BF$_3^-$K$^+$,
under Suzuki coupling conditions to give compounds of the formula (I).

The reaction of the first step according to process [A] is generally carried out in inert solvents, if appropriate in the presence of a base, preferably in a temperature range from 0° C. to room temperature at atmospheric pressure.

Suitable dehydrating agents here are, for example, carbodiimides such as N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC) (optionally in the presence of pentafluorophenol (PFP)), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulphate or 2-tert-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or bis-(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU), (benzotriazol-1-yloxy)bisdimethylaminomethylium fluoroborate (TBTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or ethyl cyano(hydroxyimino)acetate (Oxyma), or (1-cyano-2-ethoxy-2-oxo-ethylideneaminooxy)dimethylaminomorpholinocarbenium hexafluorophosphate (COMU), or N-[(dimethylamino)(3H-[1,2,3]triazolo[4,5-b]pyridin-3-yloxy)methylidene]-N-methylmethanaminium hexafluorophosphate, or 2,4,6-tripropyl-1,3,5,2,4,6-trioxatriphosphinane 2,4,6-trioxide (T3P), or mixtures of these, with bases. The condensation is preferably carried out using HATU.

Bases are, for example, alkali metal carbonates such as sodium carbonate or potassium carbonate, or sodium bicarbonate or potassium bicarbonate, or organic bases such as trialkylamines, for example triethylamine, N-methylmorpholine, N-methylpiperidine, 4-dimethylaminopyridine or diisopropylethylamine, or pyridine. The condensation is preferably carried out using diisopropylethylamine.

Inert solvents are, for example, halogenated hydrocarbons such as dichloromethane or trichloromethane, hydrocarbons such as benzene, or other solvents such as nitromethane, dioxane, dimethylformamide, dimethyl sulphoxide or acetonitrile. It is also possible to use mixtures of the solvents. Particular preference is given to dimethylformamide.

The compounds of the formula (III) are known, can be synthesized from the corresponding starting compounds by known processes or can be prepared analogously to the processes described in the Examples section.

In an acidic ester hydrolysis, the reaction of the second step according to process [A] is generally carried out in inert solvents, preferably in a temperature range from room temperature to 60° C. at atmospheric pressure.

Inert solvents are, for example, halogenated hydrocarbons such as dichloromethane, trichloromethane, carbon tetrachloride or 1,2-dichloroethane, or ethers such as tetrahydrofuran or dioxane, preference being given to dichloromethane.

Acids are, for example, trifluoroacetic acid or hydrogen chloride in dioxane, preference being given to trifluoroacetic acid.

In a basic ester hydrolysis, the reaction of the second step according to process [A] is generally carried out in inert solvents, preferably within a temperature range from room temperature up to the reflux of the solvents at standard pressure.

Inert solvents are, for example, halogenated hydrocarbons such as dichloromethane, trichloromethane, carbon tetrachloride or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvents with water, preference being given to a mixture of tetrahydrofuran and water.

Bases are, for example, alkali metal hydroxides such as sodium hydroxide, lithium hydroxide or potassium hydroxide, or alkali metal carbonates such as caesium carbonate, sodium carbonate or potassium carbonate, or alkoxides such as potassium tert-butoxide or sodium tert-butoxide, preference being given to lithium hydroxide.

The reaction in process [B] is generally effected in inert solvents, in the presence of a catalyst, optionally in the presence of an additional reagent, optionally in a microwave, preferably within a temperature range from room temperature to 150° C. at standard pressure to 3 bar.

Catalysts are, for example, palladium catalysts customary for Suzuki reaction conditions, preference being given to catalysts such as dichlorobis(triphenylphosphine)palladium, tetrakistriphenylphosphinepalladium(0), palladium(II) acetate/tricyclohexylphosphine, tris(dibenzylideneacetone) dipalladium, bis(diphenylphosphaneferrocenyl)palladium (II) chloride, 1,3-bis(2,6-diisopropylphenyl)imidazol-2-ylidene(1,4-naphthoquinone)palladium dimer, allyl(chloro) (1,3-dimesityl-1,3-dihydro-2H-imidazol-2-ylidene) palladium, palladium(II) acetate/dicyclohexyl(2',4',6'-triisopropyl-biphenyl-2-yl)phosphine, [1,1-bis (diphenylphosphino)ferrocene]palladium(II) chloride monodichloromethane adduct or XPhos precatalyst [(2'-aminobiphenyl-2-yl)(chloro)palladium dicyclohexyl(2',4', 6'-triisopropylbiphenyl-2-yl)phosphane (1:1)], preference being given to tetrakistriphenylphosphinepalladium(0), [1,1-bis-(diphenylphosphino)ferrocene]palladium(II) chloride monodichloromethane adduct or XPhos precatalyst [(2'-aminobiphenyl-2-yl)(chloro)palladium dicyclohexyl(2', 4',6'-triisopropylbiphenyl-2-yl)phosphine (1:1)].

Additional reagents are, for example, potassium acetate, caesium carbonate, potassium carbonate or sodium carbonate, potassium tert-butoxide, caesium fluoride or potassium phosphate, where these may be present in aqueous solution; preferred are additional reagents such as potassium carbonate or aqueous potassium phosphate solution.

Inert solvents are, for example, ethers such as dioxane, tetrahydrofuran or 1,2-dimethoxyethane, hydrocarbons such as benzene, xylene or toluene, or carboxamides such as dimethylformamide or dimethylacetamide, alkyl sulphoxides such as dimethyl sulphoxide, oder N-methylpyrrolidone or acetonitrile, or mixtures of the solvents with alcohols such as methanol or ethanol and/or water; preference is given to tetrahydrofuran, dioxane or acetonitrile.

The compounds of the formula (V) are known or can be synthesized by known processes from the appropriate starting materials.

The compounds of the formula (II) are known or can be prepared by

[C] reacting compounds of the formula

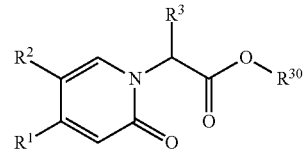

(VIa)

in which
$R^1$, $R^2$ and $R^3$ have the meaning given above and
$R^{30}$ represents tert-butyl,
with an acid,
or

[D] reacting compounds of the formula

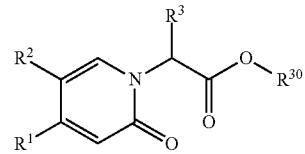

(VIb)

in which
$R^1$, $R^2$ and $R^3$ have the meaning given above and
$R^{30}$ represents methyl or ethyl,
with a base.

The compounds of the formulae (VIa) and (VIb) together form the group of the compounds of the formula (VI).

The reaction according to process [C] is generally carried out in inert solvents, preferably in a temperature range from room temperature to 60° C. at atmospheric pressure.

Inert solvents are, for example, halogenated hydrocarbons such as dichloromethane, trichloromethane, carbon tetrachloride or 1,2-dichloroethane, or ethers such as tetrahydrofuran or dioxane, preference being given to dichloromethane.

Acids are, for example, trifluoroacetic acid or hydrogen chloride in dioxane, preference being given to trifluoroacetic acid.

The reaction in process [D] is generally effected in inert solvents, preferably within a temperature range from room temperature up to the reflux of the solvents at standard pressure.

Inert solvents are, for example, halogenated hydrocarbons such as dichloromethane, trichloromethane, carbon tetrachloride or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvents with water, preference being given to a mixture of tetrahydrofuran and water.

Bases are, for example, alkali metal hydroxides such as sodium hydroxide, lithium hydroxide or potassium hydroxide, or alkali metal carbonates such as caesium carbonate, sodium carbonate or potassium carbonate, or alkoxides such as potassium tert-butoxide or sodium tert-butoxide, preference being given to lithium hydroxide.

The compounds of the formula (VI) are known or can be prepared by

[E] reacting compounds of the formula

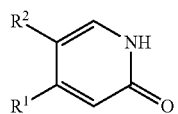

(VII)

in which
R$^1$ and R$^2$ are each as defined above,
with compounds of the formula

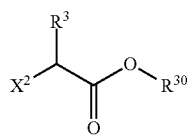

(VIII)

in which
R$^3$ has the meaning given above,
R$^{30}$ represents methyl, ethyl or tert-butyl, and
X$^2$ represents chlorine, bromine, iodine, methane sulphonyloxy or trifluoromethanesulphonyloxy,
or
[F] reacting compounds of the formula

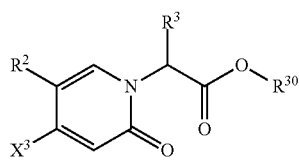

(IX)

in which
R$^2$ and R$^3$ are each as defined above,
R$^{30}$ represents methyl, ethyl or tert-butyl, and
X$^3$ represents chlorine, bromine or iodine,
with compounds of the formula (V) under Suzuki coupling conditions.

The reaction according to process [E] is generally carried out in inert solvents, optionally in the presence of a base, preferably in a temperature range from room temperature to reflux of the solvents at atmospheric pressure.

Inert solvents are, for example, halogenated hydrocarbons such as dichloromethane, trichloromethane, carbon tetrachloride or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvents with water; preference is given to dimethylformamide.

Bases are, for example, alkali metal hydroxides such as sodium hydroxide, lithium hydroxide or potassium hydroxide, or alkali metal carbonates such as caesium carbonate, sodium carbonate or potassium carbonate, or potassium tert-butoxide or sodium tert-butoxide, sodium hydride or a mixture of these bases or a mixture of sodium hydride and lithium bromide; preference is given to potassium carbonate or sodium hydride.

The compounds of the formula (VIII) are known or can be synthesized by known processes from the appropriate starting materials.

The reaction in process [F] is carried out as described for process [B].

The compounds of the formula (VII) are known or can be prepared by reacting compounds of the formula

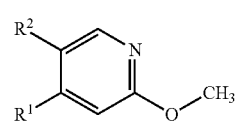

(X)

in which
R$^1$ and R$^2$ are each as defined above,
with pyridinium hydrochloride or pyridinium hydrobromide.

The reaction is generally carried out in inert solvents, preferably in a temperature range of from 80° C. to 120° C. at atmospheric pressure.

Inert solvents are, for example, hydrocarbons such as benzene, or other solvents such as nitromethane, dioxane, dimethylformamide, dimethyl sulphoxide or acetonitrile. It is also possible to use mixtures of the solvents. Particular preference is given to dimethylformamide The compounds of the formula (X) are known or can be prepared by reacting compounds of the formula

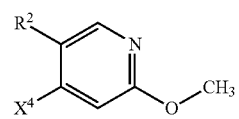

(XI)

in which $R^2$ has the meaning given above and $X^4$ represents chlorine, bromine or iodine, with compounds of the formula (V) under Suzuki coupling conditions.

The reaction is carried out as described for process [B].

The compounds of the formula (XI) are known or can be synthesized by known processes from the appropriate starting materials.

The compounds of the formula (IX) are known or can be prepared by reacting compounds of the formula

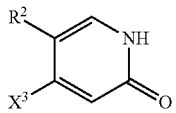
(XII)

in which $R^2$ has the meaning given above and $X^3$ represents chlorine, bromine or iodine, with compounds of the formula (VIII).

The reaction is carried out as described for process [E].

The compounds of the formula (XII) are known or can be synthesized by known processes from the appropriate starting materials.

The compounds of the formula (IV) are known or can be prepared by reacting compounds of the formula

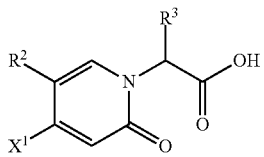
(XIII)

in which $R^2$ and $R^3$ are each as defined above, and $X^1$ represents chlorine, bromine or iodine, with compounds of the formula (III) in the presence of a dehydrating reagent.

The reaction is carried out as described for process [A].

The compounds of the formula (XIII) are known or can be prepared by

[G] reacting compounds of the formula

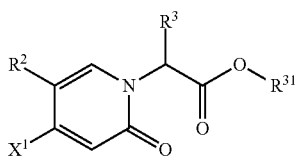
(XIVa)

in which $R^2$ and $R^3$ are each as defined above, $R^{31}$ represents tert-butyl and $X^1$ represents chlorine, bromine or iodine, with an acid, or

[H] reacting compounds of the formula

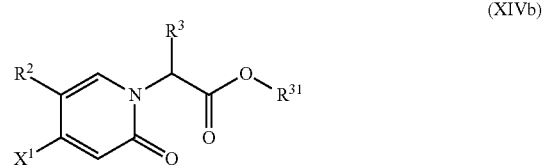
(XIVb)

in which $R^2$ and $R^3$ are each as defined above, $R^{31}$ is methyl or ethyl, and $X^1$ represents chlorine, bromine or iodine, with a base.

The compounds of the formulae (XIVa) and (XIVb) together form the group of the compounds of the formula (XIV).

The reaction according to process [G] is carried out as described for process [C].

The reaction according to process [H] is carried out as described for process [D].

The compounds of the formula (XIV) are known or can be prepared by reacting compounds of the formula

(XV)

in which $R^2$ has the meaning given above and $X^1$ represents chlorine, bromine or iodine, with compounds of the formula

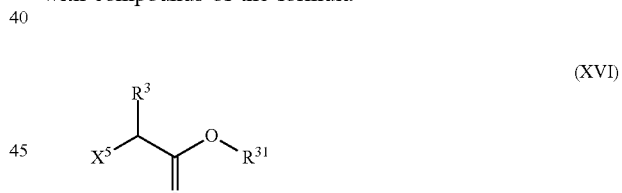
(XVI)

in which $R^3$ has the meaning given above, $R^{31}$ represents methyl, ethyl or tert-butyl, and $X^5$ represents chlorine, bromine, iodine, methanesulphonyloxy or trifluoromethanesulphonyloxy.

The reaction is carried out as described for process [E].

The compounds of the formulae (XV) and (XVI) are known or can be synthesized by known processes from the appropriate starting compounds.

In an alternative process, the compounds of the formula (VI) can be prepared by reacting compounds of the formula

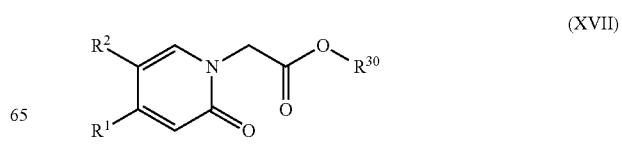
(XVII)

in which $R^1$ and $R^2$ are each as defined above, and $R^{30}$ represents methyl, ethyl or tert-butyl, with compounds of the formula $$R^3-X^6 \quad (XVIII)$$

in which $R^3$ has the meaning given above and $X^6$ represents chlorine, bromine, iodine, methanesulphonyloxy, trifluoromethanesulphonyloxy or para-toluenesulphonyloxy.

The reaction is generally carried out in inert solvents, if appropriate in the presence of a base, preferably in a temperature range from −78° C. to room temperature at atmospheric pressure.

Inert solvents are, for example, halogenated hydrocarbons, such as dichloromethane, trichloromethane, carbon tetrachloride or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvent with water; preference is given to tetrahydrofuran.

Bases are, for example, potassium tert-butoxide or sodium tert-butoxide, sodium hydride, N-butyllithium or bis(trimethylsilyl)lithium amide, preference is given to bis(trimethylsilyl)lithium amide.

The compounds of the formula (XVII) are known or can be synthesized by the processes described above, for example process [E], from the appropriate starting materials.

The compounds of the formula (XVIII) are known or can be synthesized by known processes from the appropriate starting materials.

In an alternative process, the compounds of the formula (II) can be prepared by reacting compounds of the formula

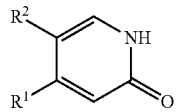

(VII)

in which $R^1$ and $R^2$ are each as defined above, with compounds of the formula

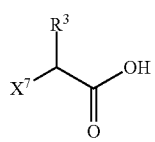

(XIX)

in which $R^3$ has the meaning given above and $X^7$ represents chlorine, bromine or iodine.

The reaction is generally carried out in inert solvents, if appropriate in the presence of a base, preferably in a temperature range from −10° C. to 90° C. at atmospheric pressure.

Inert solvents are, for example, halogenated hydrocarbons, such as dichloromethane, trichloromethane, carbon tetrachloride or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvent with water; preference is given to tetrahydrofuran.

Bases are, for example, potassium tert-butoxide or sodium tert-butoxide, sodium hydride or bis(trimethylsilyl)lithium amide or a mixture of magnesium di-tert-butoxide and potassium tert-butoxide, preference is given to a mixture of magnesium di-tert-butoxide and potassium tert-butoxide.

The compounds of the formula (XIX) are known or can be synthesized by known processes from the appropriate starting materials.

In an alternative process, the compounds of the formula (XIII) can be prepared by reacting compounds of the formula

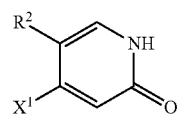

(XV)

in which $R^2$ has the meaning given above and $X^1$ represents chlorine, bromine or iodine, with compounds of the formula

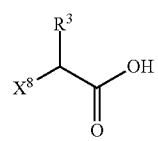

(XX)

in which $R^3$ has the meaning given above and $X^8$ represents chlorine, bromine or iodine.

The reaction is carried out as described for the reaction of compounds of the formula (VII) with compounds of the formula (XIX).

The compounds of the formula (XX) are known or can be synthesized by known processes from the appropriate starting materials.

The preparation of the starting compounds and of the compounds of the formula (I) can be illustrated by the synthesis scheme below.

Scheme 1:

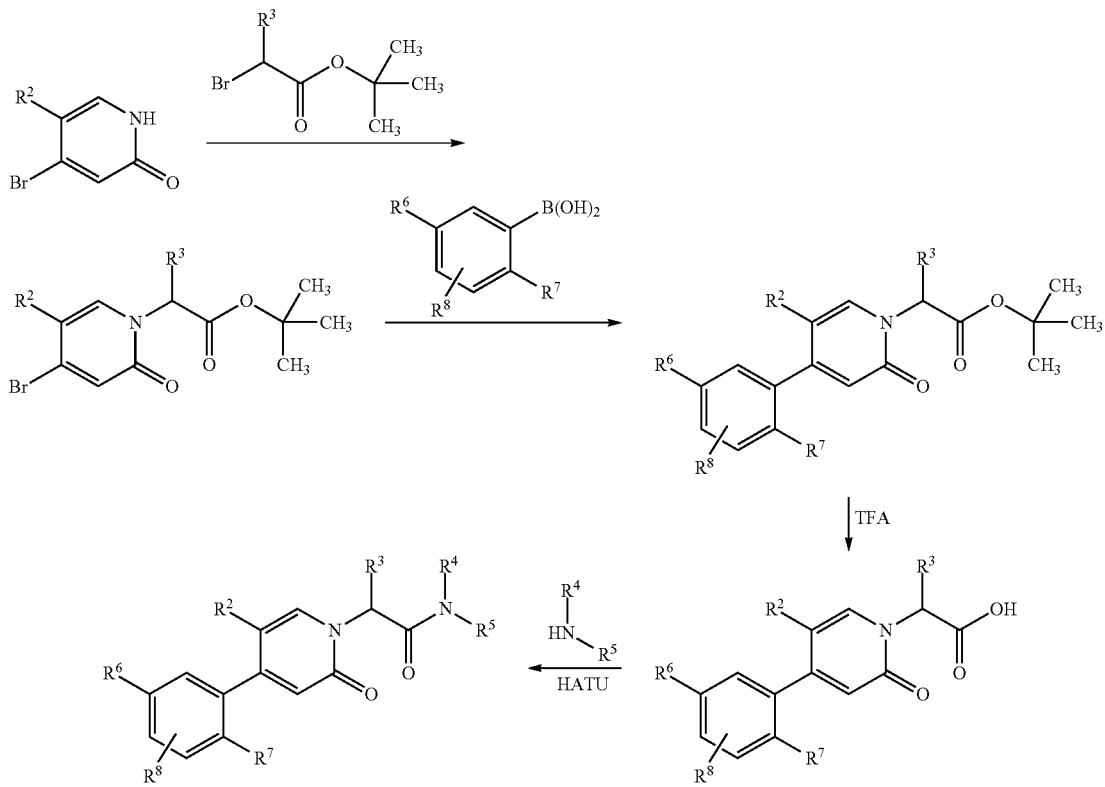

The compounds according to the invention have an unforeseeable useful pharmacological activity spectrum and good pharmacokinetic behaviour. They are compounds that influence the proteolytic activity of the serine protease factor XIa (FXIa) and/or the serine protease plasma kallikrein (PK). The compounds according to the invention inhibit the enzymatic cleavage of substrates, catalysed by FXIa and/or PK, which have essential roles in the activation of blood coagulation, in the aggregation of blood platelets via reduction of the thrombin necessary for the PAR-1 activation of the platelets, and in inflammatory processes, which particularly involve an increase in vascular permeability.

They are therefore suitable for use as medicaments for the treatment and/or prophylaxis of diseases in humans and animals.

The present invention further provides for the use of the compounds according to the invention for the treatment and/or prophylaxis of disorders, in particular cardiovascular disorders, preferably thrombotic or thromboembolic disorders and/or thrombotic or thromboembolic complications, and/or ophthalmic disorders, in particular of diabetic retinopathy or macular oedema, and/or inflammatory disorders, in particular those associated with excess plasma kallikrein activity, such as hereditary angiooedema (HAE) or chronic inflammatory disorders, particularly of the intestine such as Crohn's disease.

Factor XIa (FXIa) is an important enzyme in the context of coagulation, which can be activated both by thrombin and factor XIIa (FXIIa), and is therefore involved in two essential processes of coagulation. It is a central component of the transition from initiation to amplification and propagation of coagulation: in positive feedback loops, thrombin activates, in addition to factor V and factor VIII, also factor XI to factor XIa, whereby factor IX is converted into factor IXa, and, via the factor IXa/factor VIIIa complex generated in this manner, the factor X is activated and thrombin formation is in turn therefore highly stimulated leading to strong thrombus growth and stabilizing the thrombus.

Moreover, factor XIa is an important component for the intrinsic initiation of coagulation: In addition to the stimulation via tissue factor (TF), the coagulation system can be activated also particularly on negatively charged surfaces, which include not only surface structures of foreign cells (e.g. bacteria) but also artificial surfaces such as vascular prostheses, stents and extracoporeal circulation. On the surface, initially factor XII (FXII) is activated to factor XIIa (FXIIA) which subsequently activates FXI, attached to cell surfaces, to FXIa. This leads to further activation of the coagulation cascade as described above.

In contrast, thrombin generation in the initiation phase remains uninfluenced via TF/factor VIIa and factor X activation and finally thrombin formation, the physiological reaction on vascular injuries, remains uninfluenced. This could explain why no prolongations of bleeding times were found in FXIa knockout mice, as in rabbits and other species, with administration of FXIa inhibitor. This low bleeding tendency caused by the substance is of great advantage for use in humans, particularly in patients with increased risk of bleeding.

In addition, factor XIIa also activates plasma prokallikrein to plasma kallikrein (PK) in the context of the intrinsic activation which, inter alia, in a potentiation loop, leads to further factor XII activation, overall resulting in amplification of the initiation of the coagulation cascade on surfaces. A PK-inhibiting activity of a compound according to the invention thus reduces coagulation via surface activation and thus has an anticoagulatory effect. An advantage could be in the combination of factor XIa inhibitory activity and PK inhibitory activity allowing a balanced antithrombotic effect.

Accordingly, the compounds according to the invention are suitable for the treatment and/or prophylaxis of disorders or complications which may arise from the formation of clots.

For the purpose of the present invention, the "thrombotic or thromboembolic disorders" include disorders which occur both in the arterial and in the venous vasculature and which can be treated with the compounds according to the invention, in particular disorders in the coronary arteries of the heart, such as acute coronary syndrome (ACS), myocardial infarction with ST segment elevation (STEMI) and without ST segment elevation (non-STEMI), stable angina pectoris, unstable angina pectoris, reocclusions and restenoses after coronary interventions such as angioplasty, stent implantation or aortocoronary bypass, but also thrombotic or thromboembolic disorders in further vessels leading to peripheral arterial occlusive disorders, pulmonary embolisms, venous thromboembolisms, venous thromboses, in particular in deep leg veins and kidney veins, transitory ischaemic attacks and also thrombotic stroke and thromboembolic stroke.

Stimulation of the coagulation system may occur by various causes or associated disorders. In the context of surgical interventions, immobility, confinement to bed, infections, inflammation or cancer or cancer therapy, inter alia, the coagulation system can be highly activated, and there may be thrombotic complications, in particular venous thromboses. The compounds according to the invention are therefore suitable for the prophylaxis of thromboses in the context of surgical interventions in patients suffering from cancer. The compounds according to the invention are therefore also suitable for the prophylaxis of thromboses in patients having an activated coagulation system, for example in the stimulation situations described.

The inventive compounds are therefore also suitable for the prevention and treatment of cardiogenic thromboembolisms, for example brain ischaemias, stroke and systemic thromboembolisms and ischaemias, in patients with acute, intermittent or persistent cardiac arrhythmias, for example atrial fibrillation, and in patients undergoing cardioversion, and also in patients with heart valve disorders or with artificial heart valves.

In addition, the inventive compounds are suitable for the treatment and prevention of disseminated intravascular coagulation (DIC) which may occur in connection with sepsis inter alia, but also owing to surgical interventions, neoplastic disorders, burns or other injuries and may lead to severe organ damage through microthromboses.

Thromboembolic complications furthermore occur in microangiopathic haemolytical anaemias and by the blood coming into contact with foreign surfaces in the context of extracorporeal circulation such as, for example, haemodialysis, ECMO ("extracorporeal membrane oxygenation"), LVAD ("left ventricular assist device") and similar methods, AV fistulas, vascular and heart valve prostheses.

Moreover, the compounds according to the invention are suitable for the treatment and/or prophylaxis of disorders involving microclot formation or fibrin deposits in cerebral blood vessels which may lead to dementia disorders such as vascular dementia or Alzheimer's disease. Here, the clot may contribute to the disorder both via occlusions and by binding further disease-relevant factors.

Moreover, the compounds according to the invention are suitable in particular for the treatment and/or prophylaxis of disorders where, in addition to the pro-coagulant component, the pro-inflammatory component also plays an essential role. Mutual enhancement of coagulation and inflammation in particular can be prevented by the compounds according to the invention, thus decisively lowering the probability of thrombotic complications. In this case, both the factor XIa-inhibitory component (via inhibition of thrombin production) and the PK-inhibitory component can contribute to the anticoagulant and antiinflammatory effect (e.g. via bradykinin). Therefore, the treatment and/or prophylaxis in the context of atherosclerotic vascular disorders, inflammations in the context of rheumatic disorders of the locomotor system, inflammatory disorders of the lung, such as pulmonary fibroses, inflammatory disorders of the kidney, such as glomerulonephritides, inflammatory disorders of the intestine, such as Crohn's disease or ulcerative colitis, or disorders which may be present in the context of a diabetic underlying disease, such as diabetic retinopathy or nephropathy, may be considered, inter alia.

Kinins generated by means of plasma kallikrein, inter alia, have a causative role in the progression of chronic inflammatory intestinal disorders (CID). Their pro-inflammatory effect via activation of bradykinin receptors induces and potentiates the disease progression. Studies on Crohn's disease patients show a correlation between the kallikrein concentration in the intestinal epithelium and the degree of intestinal inflammation. Activation of the kallikrein-kinin system was likewise observed in experimental animal studies. Inhibition of bradykinin synthesis by kallikrein inhibitors could accordingly be used also for prophylaxis and/or therapy of chronic inflammatory intestinal disorders.

Moreover, the compounds according to the invention can be used for inhibiting tumour growth and the formation of metastases, and also for the prophylaxis and/or treatment of thromboembolic complications, such as, for example, venous thromboembolisms, for tumour patients, in particular those undergoing major surgical interventions or chemo- or radiotherapy.

In addition, the inventive compounds are also suitable for the prophylaxis and/or treatment of pulmonary hypertension.

In the context of the present invention, the term "pulmonary hypertension" includes pulmonary arterial hypertension, pulmonary hypertension associated with disorders of the left heart, pulmonary hypertension associated with pulmonary disorders and/or hypoxia and pulmonary hypertension owing to chronic thromboembolisms (CTEPH).

"Pulmonary arterial hypertension" includes idiopathic pulmonary arterial hypertension (IPAH, formerly also referred to as primary pulmonary hypertension), familial pulmonary arterial hypertension (FPAH) and associated pulmonary arterial hypertension (APAH), which is associated with collagenoses, congenital systemic-pulmonary shunt vitia, portal hypertension, HIV infections, the ingestion of certain drugs and medicaments, with other disorders (thyroid disorders, glycogen storage disorders, Morbus Gaucher, hereditary teleangiectasia, haemoglobinopathies, myeloproliferative disorders, splenectomy), with disorders having a significant venous/capillary contribution, such as pulmonary-venoocclusive disorder and pulmonary-capillary haemangiomatosis, and also persisting pulmonary hypertension of neonatants.

Pulmonary hypertension associated with disorders of the left heart includes a diseased left atrium or ventricle and mitral or aorta valve defects.

Pulmonary hypertension associated with pulmonary disorders and/or hypoxia includes chronic obstructive pulmonary disorders, interstitial pulmonary disorder, sleep apnoea syndrome, alveolar hypoventilation, chronic high-altitude sickness and inherent defects.

Pulmonary hypertension owing to chronic thromboembolisms (CTEPH) comprises the thromboembolic occlusion of proximal pulmonary arteries, the thromboembolic occlusion of distal pulmonary arteries and non-thrombotic pulmonary embolisms (tumour, parasites, foreign bodies).

The present invention further provides for the use of the inventive compounds for production of medicaments for the treatment and/or prophylaxis of pulmonary hypertension associated with sarcoidosis, histiocytosis X and lymphangiomatosis.

In addition, the inventive substances may also be useful for the treatment of pulmonary and hepatic fibroses.

In addition, the inventive compounds may also be suitable for the treatment and/or prophylaxis of disseminated intravascular coagulation in the context of an infectious disease, and/or of systemic inflammatory syndrome (SIRS), septic organ dysfunction, septic organ failure and multiorgan failure, acute respiratory distress syndrome (ARDS), acute lung injury (ALI), septic shock and/or septic organ failure.

In the course of an infection, there may be a generalized activation of the coagulation system (disseminated intravascular coagulation or consumption coagulopathy, hereinbelow referred to as "DIC") with microthrombosis in various organs and secondary haemorrhagic complications. Moreover, there may be endothelial damage with increased permeability of the vessels and diffusion of fluid and proteins into the extravasal space. As the infection progresses, there may be failure of an organ (for example kidney failure, liver failure, respiratory failure, central-nervous deficits and cardiovascular failure) or multiorgan failure.

In the case of DIC, there is a massive activation of the coagulation system at the surface of damaged endothelial cells, the surfaces of foreign bodies or crosslinked extravascular tissue. As a consequence, there is coagulation in small vessels of various organs with hypoxia and subsequent organ dysfunction. A secondary effect is the consumption of coagulation factors (for example factor X, prothrombin and fibrinogen) and platelets, which reduces the coagulability of the blood and may result in heavy bleeding.

Compounds according to the invention which inhibit plasma kallikrein alone or in combination with factor XIa, are also useful for the treatment and/or prophylaxis of disorders in the course of which plasma kallikrein is involved. In addition to the anticoagulant activity, plasma kallikrein is an important bradikinin-releasing protease which, inter alia, thus leads to increased endothelial permeability. The compounds can therefore be used for the treatment and/or prophylaxis of disorders involving oedema formations such as ophthalmic disorders, in particular, diabetic retinopathy or macular oedema or hereditary angiooedema.

"Ophthalmic disorders" in the context of the present invention include in particular disorders such as diabetic retinopathy, diabetic macular oedema (DME), macular oedema, macular oedema associated with retinal vein occlusion, age-related macular degeneration (AMD), choroidal neovascularization (CNV), choroidal neovascular membranes (CNVM), cystoid macula oedema (CME), epiretinal membranes (ERM) and macula perforations, myopia-associated choroidal neovascularization, angioid streaks, vascular streaks, retina detachment, atrophic changes of the retinal pigment epithelium, hypertrophic changes of the retinal pigment epithelium, retinal vein occlusion, choroidal retinal vein occlusion, retinitis pigmentosa, Stargardt's disease, retinopathy of prematurity, glaucoma, inflammatory eye disorders such as uveitis, scleritis or endophthalmitis, cataract, refraction anomalies such as myopia, hyperopia or astigmatism and keratoconus, disorders of the anterior eye such as corneal angiogenesis as sequela of, for example, ceratitis, cornea transplantation or keratoplasty, corneal angiogenesis as sequela of hypoxia (for example by excessive use of contact lenses), pterygium conjunctivae, subcorneal oedema and intracorneal oedema.

The compounds according to the invention are also suitable for the primary prophylaxis of thrombotic or thromboembolic disorders and/or inflammatory disorders and/or disorders with increased vascular permeability in patients in which gene mutations lead to enhanced activity of the enzymes, or increased levels of the zymogens and these are established by relevant tests/measurements of the enzyme activity or zymogen concentrations.

The present invention further provides for the use of the compounds according to the invention for the treatment and/or prophylaxis of disorders, especially the disorders mentioned above.

The present invention further provides for the use of the compounds according to the invention for production of a medicament for the treatment and/or prophylaxis of disorders, especially the disorders mentioned above.

The present invention further provides a method for the treatment and/or prophylaxis of disorders, especially the disorders mentioned above, using a therapeutically effective amount of a compound according to the invention.

The present invention further provides the compounds according to the invention for use in a method for the treatment and/or prophylaxis of disorders, especially the disorders mentioned above, using a therapeutically effective amount of a compound according to the invention.

The present invention further provides medicaments comprising a compound according to the invention and one or more further active compounds.

In addition, the compounds according to the invention can also be used for preventing coagulation ex vivo, for example for the protection of organs to be transplanted against organ damage caused by formation of clots and for protecting the organ recipient against thromboemboli from the transplanted organ, for preserving blood and plasma products, for cleaning/pretreating catheters and other medical auxiliaries and instruments, for coating synthetic surfaces of medical auxiliaries and instruments used in vivo or ex vivo or for biological samples which may comprise factor XIa or plasma kallikrein.

The present invention furthermore provides a method for preventing the coagulation of blood in vitro, in particular in banked blood or biological samples which may comprise factor XIa or plasma kallikrein or both enzymes, which method is characterized in that an anticoagulatory effective amount of the compound according to the invention is added.

The present invention further provides medicaments comprising a compound according to the invention and one or more further active compounds, in particular for the treatment and/or prophylaxis of the disorders mentioned above. Preferred examples of active compounds suitable for combinations include:

lipid-lowering substances, especially HMG-CoA (3-hydroxy-3-methylglutaryl-coenzyme A) reductase inhibitors, for example lovastatin (Mevacor), simvastatin (Zocor), pravastatin (Pravachol), fluvastatin (Lescol) and atorvastatin (Lipitor);

coronary therapeutics/vasodilators, especially ACE (angiotensin converting enzyme) inhibitors, for example captopril, lisinopril, enalapril, ramipril, cilazapril, benazepril, fosinopril, quinapril and perindopril, or AII (angiotensin II) receptor antagonists, for example embusartan, losartan, valsartan, irbesartan, candesartan, eprosartan and temisartan, or (3-adrenoceptor antagonists, for example carvedilol, alprenolol, bisoprolol, acebutolol, atenolol, betaxolol, carteolol, metoprolol, nadolol, penbutolol, pindolol, propanolol and timolol, or alpha-1-adrenoceptor antagonists, for example prazosine, bunazosine, doxazosine and terazosine, or diuretics, for example hydrochlorothiazide, furosemide, bumetanide, piretanide, torasemide, amiloride and dihydralazine, or calcium channel blockers, for example verapamil and diltiazem, or dihydropyridine derivatives, for example nifedipin (Adalat) and nitrendipine (Bayotensin), or nitro preparations, for example isosorbide 5-mononitrate, isosorbide dinitrate and glycerol trinitrate, or substances causing an increase in cyclic guanosine monophosphate (cGMP), for example stimulators of soluble guanylate cyclase, for example riociguat;

plasminogen activators (thrombolytics/fibrinolytics) and compounds which promote thrombolysis/fibrinolysis such as inhibitors of the plasminogen activator inhibitor (PAI inhibitors) or inhibitors of the thrombin-activated fibrinolysis inhibitor (TAFT inhibitors) such as, for example, tissue plasminogen activator (t-PA, for example Actilyse®), streptokinase, reteplase and urokinase or plasminogen-modulating substances causing increased formation of plasmin;

anticoagulatory substances (anticoagulants), for example heparin (UFH), low-molecular-weight heparins (LMWH), for example tinzaparin, certoparin, parnaparin, nadroparin, ardeparin, enoxaparin, reviparin, dalteparin, danaparoid, semuloparin (AVE 5026), adomiparin (M118) and EP-42675/ORG42675;

direct thrombin inhibitors (DTI) such as, for example, Pradaxa (dabigatran), atecegatran (AZD-0837), DP-4088, SSR-182289A, argatroban, bivalirudin and tanogitran (BIBT-986 and prodrug BIBT-1011), hirudin;

direct factor Xa inhibitors, for example, rivaroxaban, apixaban, edoxaban (DU-176b), betrixaban (PRT-54021), R-1663, darexaban (YM-150), otamixaban (FXV-673/RPR-130673), letaxaban (TAK-442), razaxaban (DPC-906), DX-9065a, LY-517717, tanogitran (BIBT-986, prodrug: BIBT-1011), idraparinux and fondaparinux, substances which inhibit the aggregation of platelets (platelet aggregation inhibitors, thrombocyte aggregation inhibitors), such as, for example, acetylsalicylic acid (such as, for example, aspirin), P2Y12 antagonists such as, for example, ticlopidine (Ticlid), clopidogrel (Plavix), prasugrel, ticagrelor, cangrelor, elinogrel, PAR-1 antagonists such as, for example, vorapaxar, PAR-4 antagonists, EP3 antagonists such as, for example, DG041;

platelet adhesion inhibitors such as GPVI and/or GPIb antagonists such as, for example, Revacept or caplacizumab;

fibrinogen receptor antagonists (glycoprotein-IIb/IIIa antagonists), for example abciximab, eptifibatide, tirofiban, lamifiban, lefradafiban and fradafiban;

recombinant human activated protein C such as, for example, Xigris or recombinant thrombomudulin;

and also antiarrhythmics;

inhibitors of VEGF and/or PDGF signal paths such as, for example, aflibercept, ranibizumab, bevacizumab, KH-902, pegaptanib, ramucirumab, squalamin or bevasiranib, apatinib, axitinib, brivanib, cediranib, dovitinib, lenvatinib, linifanib, motesanib, pazopanib, regorafenib, sorafenib, sunitinib, tivozanib, vandetanib, vatalanib, Vargatef and E-10030;

inhibitors of angiopoietin-Tie signal paths such as, for example, AMG386;

inhibitors of Tie2 receptor tyrosine kinase;

inhibitors of the integrin signal paths such as, for example, volociximab, cilengitide and ALG1001;

inhibitors of the PI3K-Akt-mTor signal paths such as, for example, XL-147, perifosine, MK2206, sirolimus, temsirolimus and everolimus;

corticosteroids such as, for example, anecortave, betamethasone, dexamethasone, triamcinolone, fluocinolone and fluocinolone acetonide;

inhibitors of the ALK1-Smad1/5 signal path such as, for example, ACE041;

cyclooxygenase inhibitors such as, for example, bromfenac and nepafenac;

inhibitors of the kallikrein-kinin system such as, for example, safotibant and ecallantide;

inhibitors of the sphingosine 1-phosphate signal paths such as, for example, sonepcizumab;

inhibitors of the complement-C5a receptor such as, for example, eculizumab;

inhibitors of the 5HT1a receptor such as, for example, tandospirone;

inhibitors of the Ras-Raf-Mek-Erk signal path; inhibitors of the MAPK signal paths; inhibitors of the FGF signal paths; inhibitors of endothelial cell proliferation; apoptosis-inducing active compounds;

photodynamic therapy consisting of an active compound and the action of light, the active compound being, for example, verteporfin.

"Combinations" for the purpose of the invention mean not only dosage forms which contain all the components (so-called fixed combinations) and combination packs which contain the components separate from one another, but also components which are administered simultaneously or sequentially, provided that they are used for the prophylaxis and/or treatment of the same disease. It is likewise possible to combine two or more active ingredients with one another, meaning that they are thus each in two-component or multicomponent combinations.

The compounds of the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds of the invention can be administered in administration forms suitable for these administration routes.

Suitable administration forms for oral administration are those which function according to the prior art and deliver the inventive compounds rapidly and/or in modified fashion, and which contain the inventive compounds in crystalline and/or amorphized and/or dissolved form, for example tablets (uncoated or coated tablets, for example having enteric coatings or coatings which are insoluble or dissolve with a delay, which control the release of the compound according to the invention), tablets which disintegrate rapidly in the mouth, or films/wafers, films/lyophilisates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilisates or sterile powders.

Suitable for extraocular (topic) administration are administration forms which operate in accordance with the prior art, which release the active compound rapidly and/or in a modified or controlled manner and which contain the active compound in crystalline and/or amorphized and/or dissolved form such as, for example, eye drops, sprays and lotions (e.g. solutions, suspensions, vesicular/colloidal systems, emulsions, aerosols), powders for eye drops, sprays and lotions (e.g. ground active compound, mixtures, lyophilisates, precipitated active compound), semisolid eye preparations (e.g. hydrogels, in-situ hydrogels, creams and ointments), eye inserts (solid and semisolid preparations, e.g. bioadhesives, films/wafers, tablets, contact lenses).

Intraocular administration includes, for example, intravitreal, subretinal, subscleral, intrachoroidal, subconjunctival, retrobulbar and subtenon administration. Suitable for intraocular administration are administration forms which operate in accordance with the prior art, which release the active compound rapidly and/or in a modified or controlled manner and which contain the active compound in crystalline and/or amorphized and/or dissolved form such as, for example, preparations for injection and concentrates for preparations for injection (e.g. solutions, suspensions, vesicular/colloidal systems, emulsions), powders for preparations for injection (e.g. ground active compound, mixtures, lyophilisates, precipitated active compound), gels for preparations for injection (semisolid preparations, e.g. hydrogels, in-situ hydrogels) and implants (solid preparations, e.g. biodegradable and nonbiodegradable implants, implantable pumps).

Preference is given to oral administration or, in the case of ophthalmologic disorders, extraocular and intraocular administration.

Suitable administration forms for the other administration routes are, for example, pharmaceutical forms for inhalation (including powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

The compounds of the invention can be converted to the administration forms mentioned. This can be accomplished in a manner known per se by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colourants (e.g. inorganic pigments, for example iron oxides) and flavour and/or odour correctants.

The present invention further provides medicaments comprising at least one inventive compound, preferably together with one or more inert nontoxic pharmaceutically suitable excipients, and the use thereof for the purposes mentioned above.

In the case of parenteral administration, it has generally been found to be advantageous to administer amounts of about 5 to 250 mg every 24 hours to achieve effective results. In the case of oral administration, the amount is about 5 to 500 mg every 24 hours.

In spite of this, it may be necessary, if appropriate, to deviate from the amounts specified, specifically depending on body weight, administration route, individual behaviour towards the active ingredient, type of formulation, and time or interval of administration.

Unless stated otherwise, the percentages in the tests and examples which follow are percentages by weight; parts are parts by weight. Solvent ratios, dilution ratios and concentration data for the liquid/liquid solutions are based in each case on volume. "w/v" means "weight/volume". For example, "10% w/v" means: 100 ml of solution or suspension comprise 10 g of substance.

A) EXAMPLES

Abbreviations:
Boc tert.-butyloxycarbonyl
ca. circa
d day(s), doublet (in NMR)
DABCO 1,4-diazabicyclo[2.2.2]octane
TLC thin-layer chromatography
DCI direct chemical ionization (in MS)
dd doublet of doublets (in NMR)
DIC N,N'-diisopropylcarbodiimide
DIEA N,N-diisopropylethylamine
DMAP 4-dimethylaminopyridine
DMF N,N-dimethylformamide
DMSO dimethyl sulphoxide
eq. equivalent(s)
ESI electrospray ionization (in MS)
h hour(s)
HATU O-(7-azabenzotriazol-1-yl)-N,N,N',N'-tetramethyluronium hexafluorophosphate
HPLC high-pressure, high-performance liquid chromatography
HV high vacuum
LC-MS liquid chromatography-coupled mass spectroscopy
LDA lithium diisopropylamide
m multiplet (in NMR)
min minute(s)
MS mass spectroscopy
NMR nuclear magnetic resonance spectroscopy
Oxima ethyl hydroxyiminocyanoacetate
q quartet (in NMR)
quant. quantitative
quin quintet (in NMR)
RP reversed phase (in HPLC)
RT room temperature
$R_t$ retention time (in HPLC)
s singlet (in NMR)
sxt sextet (in NMR)

SFC supercritical fluid chromatography (with supercritical carbon dioxide as mobile phase)
t triplet (in NMR)
THF tetrahydrofuran
TFA trifluoroacetic acid
T3P 2,4,6-tripropyl-1,3,5,2,4,6-trioxatriphosphinane 2,4,6-trioxide
Xantphos 4,5-bis(diphenylphosphino)-9,9-dimethylxanthene
XPhos precatalyst [(2'-aminobiphenyl-2-yl)(chloro)palladium dicyclohexyl(2',4',6'-triisopropylbiphenyl-2-yl)phosphane (1:1)], J. Am. Chem. Soc. 2010, 132, 14073-14075
CATAXCium A precatalyst (2'-aminobiphenyl-2-yl)(methanesulphonate)palladium butyl[di-precatalyst (3S,5S,7S) tricyclo[3.3.1.13,7]dec-1-yl]phosphane (1:1)

HPLC, LC-MS and GC Methods:

Method 1: Instrument: Waters ACQUITY SQD UPLC system; column: Waters Acquity UPLC HSS T3 1.8µ 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 208-400 nm.

Method 2: Instrument: Waters ACQUITY SQD UPLC system; column: Waters Acquity UPLC HSS T3 1.8µ 50 mm×1 mm; mobile phase A: 1 l of water+0.25 ml of 99% strength formic acid, mobile phase B: 1 l of acetonitrile+0.25 ml of 99% strength formic acid; gradient: 0.0 min 95% A→6.0 min 5% A→7.5 min 5% A; oven: 50° C.; flow rate: 0.35 ml/min; UV detection: 210-400 nm.

Method 3: Instrument: Micromass Quattro Premier with Waters UPLC Acquity; column: Thermo Hypersil GOLD 1.9µ 50 mm×1 mm; mobile phase A: 1 l of water+0.5 ml of 50% strength formic acid, mobile phase B: 1 l of acetonitrile+0.5 ml of 50% strength formic acid; gradient 0.0 min 97% A→0.5 min 97% A→3.2 min 5% A→4.0 min 5% A; oven: 50° C.; flow rate: 0.3 ml/min; UV detection: 210 nm.

Method 4: MS instrument: Waters (Micromass) Quattro Micro; HPLC instrument: Agilent 1100 series; column: YMC-Triart C18 3µ 50 mm×3 mm; mobile phase A: 1 l of water+0.01 mol of ammonium carbonate, mobile phase B: 1 l of acetonitrile; gradient: 0.0 min 100% A→2.75 min 5% A→4.5 min 5% A; oven: 40° C.; flow rate: 1.25 ml/min; UV detection: 210 nm.

Method 5: MS instrument: Waters (Micromass) QM; HPLC instrument: Agilent 1100 series; column: Agient ZORBAX Extend-C18 3.0 mm×50 mm 3.5 micron; mobile phase A: 1l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 6: MS instrument: Waters (Micromass) ZQ; HPLC instrument: Agilent 1100 series; column: Agient ZORBAX Extend-C18 3.0 mm×50 mm 3.5 micron; mobile phase A: 1l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 7: Instrument: Thermo DFS, Trace GC Ultra; column: Restek RTX-35, 15 m×200 µm×0.33 µm; constant helium flow rate: 1.20 ml/min; oven: 60° C.; inlet: 220° C.; gradient: 60° C., 30° C./min→300° C. (maintained for 3.33 min)

Method 8: Instrument: Agilent MS Quad 6150; HPLC: Agilent 1290; column: Waters Acquity UPLC HSS T3 1.8µ 50 mm×2.1 mm; mobile phase A: 1 l of water+0.25 ml of 99% strength formic acid, mobile phase B: 1 l of acetonitrile+0.25 ml of 99% strength formic acid; gradient 0.0 min 90% A→0.3 min 90% A→1.7 min 5% A→3.0 min 5% A; oven: 50° C.; flow rate: 1.20 ml/min; UV detection: 205-305 nm.

Method 9: Instrument: Thermo Scientific DSQII, Thermo Scientific Trace GC Ultra; column: Restek RTX-35MS, 15 m×200 µm×0.33 µm; constant flow rate with helium: 1.20 ml/min; oven: 60° C.; inlet: 220° C.; gradient: 60° C., 30° C./min→300° C. (maintained for 3.33 min)

Microwave: The microwave reactor used was a "single-mode" instrument of the Emrys™ Optimizer type.

When compounds according to the invention are purified by preparative HPLC by the above-described methods in which the eluents contain additives, for example trifluoroacetic acid, formic acid or ammonia, the compounds according to the invention may be obtained in salt form, for example as trifluoroacetate, formate or ammonium salt, if the compounds according to the invention contain a sufficiently basic or acidic functionality Such a salt can be converted to the corresponding free base or acid by various methods known to the person skilled in the art.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "sodium salt" or "x HCl", "x CF$_3$COOH", "x Na$^+$" should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

Starting Materials

General Method 1A: Preparation of a Boronic Acid

At −78° C., lithium diisopropylamide (2 M in tetrahydrofuran/heptane/ethylbenzene) was added to a solution of the appropriate pyridine derivative in tetrahydrofuran (3 ml/mmol), the mixture was stirred for 2-4 h and triisopropyl borate was then added quickly. The reaction mixture was maintained at −78° C. for a further 2-3 h and then slowly thawed to RT overnight. After addition of water, the tetrahydrofuran was removed under reduced pressure and the aqueous phase was extracted twice with ethyl acetate. The aqueous phase was acidified with aqueous hydrochloric acid (2M), generally resulting in formation of a precipitate which was filtered off, washed with water and dried. The aqueous phase was extracted three times with ethyl acetate. The combined organic phases were dried (sodium sulphate or magnesium sulphate), filtered and concentrated under reduced pressure.

General Method 2A: Suzuki Coupling

In a flask which had been dried by heating and flushed with argon, 1.0 eq. of the appropriate boronic acids, 1.0 eq. of the aryl bromide or aryl iodide, 3.0 eq. of potassium carbonate and 0.1 eq. of [1,1-bis-(diphenylphosphino)ferrocene]palladium(II) chloride/monodichloromethane adduct or tetrakis(triphenylphosphine)palladium(0) were initially charged. The flask was then evacuated three times and in each case vented with argon. Dioxane (about 6 ml/mmol) was added, and the reaction mixture was stirred at 110° C.

for a number of hours until substantially complete conversion had been achieved. The reaction mixture was then filtered through Celite and the filtrate was concentrated under reduced pressure. Water was added to the residue. After addition of ethyl acetate and phase separation, the organic phase was washed once with water and once with saturated aqueous sodium chloride solution, dried (sodium sulphate or magnesium sulphate), filtered and concentrated under reduced pressure. The crude product was then purified either by normal phase chromatography (mobile phase: cyclohexane/ethyl acetate mixtures or dichloromethane/methanol mixtures) or by preparative RP-HPLC (water/acetonitrile gradient or water/methanol gradient).

General Method 3A: Methoxypyridine Cleavage 20 eq. of pyridinium hydrochloride or pyridinium hydrobromide were added to a solution of the appropriate methoxypyridine in dimethylformamide (10-12.5 ml/mmol) and the mixture was stirred at 100° C. for a number of hours to days, with further pyridinium hydrochloride or pyridinium hydrobromide possibly being added, until substantially complete conversion had been achieved. Subsequently, the reaction solution was concentrated under reduced pressure and the residue was triturated with water. The precipitate formed was filtered off, washed with water and dried under reduced pressure.

General Method 4A: N-Alkylation of 2-pyridinone Derivatives with the Appropriate 2-bromo- or 2-chloropropanoic Acid Derivatives Under argon, a suspension of 1.0 eq. of the appropriate 2-pyridinone derivative, 2.0 eq. of magnesium di-tert-butoxide and 1.05 eq. of potassium tert-butoxide in tetrahydrofuran (5-10 ml/mmol) was stirred at RT for 10-20 min. The reaction mixture was cooled in an ice bath, and 1.5 eq. of the appropriate 2-bromo- or 2-chloropropanoic acid derivative were added. The reaction mixture was then stirred initially at RT for 2.5 h and then further at 35–90° C. overnight, and aqueous hydrochloric acid (6 N) was added. After addition of ethyl acetate and phase separation, the organic phase was washed once with water and once with saturated aqueous sodium chloride solution, dried (sodium sulphate or magnesium sulphate), filtered and concentrated under reduced pressure. The crude product was then purified either by normal phase chromatography (mobile phase: cyclohexane/ethyl acetate mixtures or dichloromethane/methanol mixtures) or by preparative RP-HPLC (water/acetonitrile gradient or water/methanol gradient).

General Method 4B: N-Alkylation of 2-pyridinone Derivatives with the Appropriate 2-bromo- or 2-chloropropanoic Ester Derivatives in the Presence of Potassium Carbonate Under argon and at RT, 1.2 eq. of the appropriate 2-bromo- or 2-chloropropanoic ester derivative and 1.5 eq. of potassium carbonate were added to a solution of 1.0 eq. of the appropriate 2-pyridinone derivative in dimethylformamide (5-10 ml/mmol), and the mixture was stirred at 100° C. After removal of the dimethylformamide and addition of water/ethyl acetate and phase separation, the organic phase was washed with water and with saturated aqueous sodium chloride solution, dried (sodium sulphate or magnesium sulphate), filtered and concentrated under reduced pressure. The crude product was then purified either by normal phase chromatography (mobile phase: cyclohexane/ethyl acetate mixtures or dichloromethane/methanol mixtures) or by preparative RP-HPLC (water/acetonitrile gradient or water/methanol gradient).

General Method 4C: N-Alkylation of 2-pyridinone Derivatives with the Appropriate Triflates in the Presence of Sodium Hydride Under argon and at RT, sodium hydride (1.1-1.5 eq.) was added to a solution of the appropriate 2-pyridinone derivative (1 eq.) in tetrahydrofuran (0.05-0.2M), and the mixture was stirred for 30-90 min. The appropriate triflate (1.0-2.0 eq.) was then added neat or as a solution in tetrahydrofuran. The resulting reaction mixture was stirred at RT for another 1-5 h. Saturated aqueous ammonium chloride solution was added to the reaction mixture. After phase separation, the aqueous phase was extracted with ethyl acetate. The combined organic phases were dried (sodium sulphate or magnesium sulphate), filtered and concentrated under reduced pressure. The crude product was then purified either by normal phase chromatography (mobile phase: cyclohexane/ethyl acetate mixtures or dichloromethane/methanol mixtures) or by preparative RP-HPLC (water/acetonitrile gradient or water/methanol gradient).

General Method 5A: Amide Coupling with HATU/DIEA

Under argon and at RT, the amine (1.1 eq.), N,N-diisopropylethylamine (2.2 eq.) and a solution of HATU (1.2 eq.) in a little dimethylformamide were added to a solution of the appropriate carboxylic acid (1.0 eq.) in dimethylformamide (7-15 ml/mmol). The reaction mixture was stirred at RT. After addition of water/ethyl acetate and phase separation, the organic phase was washed with water and with saturated aqueous sodium chloride solution, dried (sodium sulphate or magnesium sulphate), filtered and concentrated under reduced pressure. The crude product was then purified either by normal phase chromatography (mobile phase: cyclohexane/ethyl acetate mixtures or dichloromethane/methanol mixtures) or by preparative RP-HPLC (water/acetonitrile gradient or water/methanol gradient).

General Method 5B: Amide Coupling with OXIMA/DIC

N,N'-Diisopropylcarbodiimide (DIC) (1 eq.) was added dropwise to a degassed solution of the appropriate carboxylic acid (1 eq.), aniline (1 eq.) and ethyl hydroxyiminocyanoacetate (Oxima) (1 eq.) in dimethylformamide (0.1M), and the resulting reaction solution was stirred at RT to 40° C. for 8-24 h. The solvent was removed under reduced pressure. The residue was either admixed with water and the desired product was filtered off or purified by normal phase chromatography (cyclohexane/ethyl acetate gradient) or preparative RP-HPLC (water/acetonitrile gradient or water/methanol gradient).

General Method 5C: Amide Coupling Using T3P/DIEA

Under argon and at 0° C., N,N-diisopropylethylamine (3 eq.) and propylphosphonic anhydride (T3P, 50% in dimethylformamide, 3 eq.) were added dropwise to a solution of the carboxylic acid and the appropriate amine (1.1-1.5 eq.) in dimethylformamide (0.15-0.05 mmol). The reaction mixture was stirred at RT and then concentrated under reduced pressure. After addition of water/ethyl acetate and phase separation, the aqueous phase was extracted twice with ethyl acetate. The combined organic phases were dried (sodium sulphate or magnesium sulphate), filtered and concentrated under reduced pressure. The crude product was then purified either by flash chromatography (silica gel 60, mobile phase: cyclohexane/ethyl acetate mixtures or dichloromethane/methanol mixtures) or by preparative HPLC (Reprosil C18, water/acetonitrile gradient or water/methanol gradient).

General Method 5D: Amide Coupling Using T3P/Pyridine

A solution of the appropriate carboxylic acid (1 eq.) and the appropriate amine (1.1-1.5 eq.) in pyridine (about 0.1M) was heated to 60° C., and T3P (50% in ethyl acetate, 15 eq.) was added dropwise. Alternatively, T3P was added at RT and the mixture was then stirred at RT or heated to 60 to 90° C. After 1-20 h, the reaction mixture was cooled to RT, and water and ethyl acetate were added. The aqueous phase was extracted with ethyl acetate. The combined organic phases were washed with aqueous buffer solution (pH=5), with saturated aqueous sodium bicarbonate solution and with saturated aqueous sodium chloride solution, dried over sodium sulphate and concentrated under reduced pressure. The crude product was then optionally purified either by normal phase chromatography (mobile phase: cyclohexane/ethyl acetate mixtures or dichloromethane/methanol mixtures) or by preparative RP-HPLC (water/acetonitrile gradient or water/methanol gradient).

General Method 6A: Hydrolysis of a Tert-butyl Ester or a Boc-protected Amine Using TFA At RT, 20 eq. of TFA were added to a solution of 1.0 eq. of the appropriate tert-butyl ester derivative in dichloromethane (about 5-10 ml/mmol), and the mixture was stirred at RT for 1-8 h. The reaction mixture was then concentrated under reduced pressure and the residue was co-evaporated repeatedly with dichloromethane and toluene and dried under reduced pressure. The crude product was then optionally purified either by normal phase chromatography (mobile phase: cyclohexane/ethyl acetate mixtures or dichloromethane/methanol mixtures) or by preparative RP-HPLC (water/acetonitrile gradient or water/methanol gradient).

General Method 6B: Hydrolysis of a Methyl/Ethyl or Benzyl Ester with Lithium Hydroxide At RT, lithium hydroxide (2-4 eq.) was added to a solution of 1.0 eq. of the appropriate methyl or ethyl ester in tetrahydrofuran/water (3:1, ca. 7-15 ml/mmol). The reaction mixture was stirred at RT to 60° C. and then adjusted to pH 1 using aqueous hydrochloric acid (1N). After addition of water/ethyl acetate and phase separation, the aqueous phase was extracted three times with ethyl acetate. The combined organic phases were dried (sodium sulphate or magnesium sulphate), filtered and concentrated under reduced pressure. The crude product was then purified either by normal phase chromatography (mobile phase: cyclohexane/ethyl acetate mixtures or dichloromethane/methanol mixtures) or by preparative RP-HPLC (water/acetonitrile gradient or water/methanol gradient).

General Method 7A: Preparation of Triflates

A solution of the appropriate alcohol (1 eq.) was initially charged in dichloromethane (0.1M), and at −20° C. lutidine (1.1-1.5 eq.) or triethylamine (1.1-1.5 eq.) and trifluoromethanesulphonic anhydride (1.05-1.5 eq.) were added in succession. The reaction mixture was stirred at −20° C. for another 1 h and then diluted with triple the amount (based on the reaction volume) of methyl tert-butyl ether. The organic phase was washed three times with a 3:1 mixture of saturated aqueous sodium chloride solution/1N hydrochloric acid and finally with saturated aqueous sodium bicarbonate solution, dried (sodium sulphate or magnesium sulphate) and filtered, and the solvent was removed under reduced pressure. The crude product was used in the next step without further purification.

General Method 8A: Alkylation of Acetic Esters with Triflates

Under argon and at −78° C., bis(trimethylsilyl)lithium amide (1.0M in THF, 1.1-1.3 eq.) was added dropwise to a solution of the appropriate acetic ester (1 eq.) in tetrahydrofuran (0.1-0.2M), and the mixture was stirred for 15 min. The appropriate alkyl triflate (1.5-2.0 eq.) was then added neat or as a solution in THF. The resulting reaction mixture was stirred at −78° C. for another 15 min and at RT for another 1 h. Saturated aqueous ammonium chloride solution was added to the reaction mixture. After phase separation, the aqueous phase was extracted with ethyl acetate. The combined organic phases were dried (sodium sulphate or magnesium sulphate), filtered and concentrated under reduced pressure. The crude product was then purified either by normal phase chromatography (mobile phase: cyclohexane/ethyl acetate mixtures or dichloromethane/methanol mixtures) or by preparative RP-HPLC (water/acetonitrile gradient or water/methanol gradient).

General Method 8B: Alkylation of Acetic Esters with Halides

Under argon and at −78° C., 1.1 eq. of bis(trimethylsilyl) lithium amide (1.0M in THF) were added to a solution of the appropriate acetic ester in THF (about 10 ml/mmol), and the mixture was stirred at −78° C. for 10 min A solution of the appropriate iodide/bromide/chloride in THF was then added, and the reaction mixture was stirred at −78° C. for 10 min and further in an ice bath and then quenched with water. After addition of ethyl acetate and phase separation, the aqueous phase was extracted twice with ethyl acetate. The combined organic phases were dried (sodium sulphate), filtered and concentrated under reduced pressure. The crude product was then purified either by flash chromatography (silica gel 60, mobile phase: cyclohexane/ethyl acetate mixtures or dichloromethane/methanol mixtures) or by preparative HPLC (Reprosil C18, water/acetonitrile gradient or water/methanol gradient).

Example 1.1A

Ethyl 6-aminoimidazo[1,2-a]pyridine-2-carboxylate

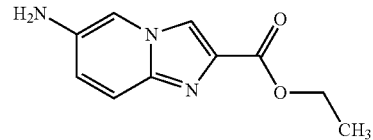

A solution of 250 mg (1.01 mmol) of ethyl 6-nitroimidazo[1,2-a]pyridine-2-carboxylate in 20 ml of ethanol was hydrogenated in the presence of 30 mg of palladium (10% on activated carbon) at RT and standard pressure for 5 h. The reaction mixture was then filtered through Celite and the residue was washed with ethanol. The combined filtrates were concentrated under reduced pressure and dried. Yield: 215 mg (quant.)

LC/MS [Method 5]: $R_t$=1.40 min; MS (ESIpos): m/z=206 (M+H)$^+$, $^1$H-NMR (400 MHz, DMSO-d$_6$): δ [ppm]=8.33 (s, 1H), 7.66 (s, 1H), 7.37 (d, 1H), 6.94 (dd, 1H), 5.11 (s, 2H), 4.26 (q, 2H), 1.29 (t, 3H).

Example 1.2A

Ethyl 7-nitroimidazo[1,2-a]pyridine-2-carboxylate

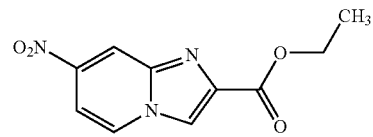

Under argon and at RT, 434 mg (3.14 mmol, 1.1 eq.) of potassium carbonate, 212 μl (2.66 mmol, 1.1 eq.) of iodoethane and 5 ml of tetrahydrofuran (to improve stirrability) were added to a suspension of 500 mg (2.41 mmol) of 7-nitroimidazo[1,2-a]pyridine-2-carboxylic acid in 20 ml of dimethylformamide, and the mixture was stirred at RT overnight. After addition of a further 35 μl (0.48 mmol, 0.2 eq.) of iodoethane and stirring at RT for a further 2 d, the reaction mixture was concentrated under reduced pressure. Water was added to the residue, the mixture was filtered and the product was dried under reduced pressure. Yield: 273 mg (48% of theory)

LC/MS [Method 1]: $R_t$=0.71 min; MS (ESIpos): m/z=236 (M+H)$^+$.

Example 1.2B

Ethyl 7-aminoimidazo[1,2-a]pyridine-2-carboxylate

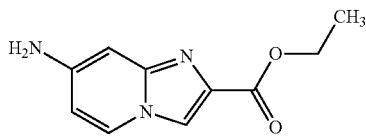 [SMILES: CCOC(=O)c1cn2ccc([N+](=O)[O-])cc2n1]

A solution of 273 mg (1.16 mmol) of ethyl 7-nitroimidazo[1,2-a]pyridine-2-carboxylate in 10 ml of ethanol was hydrogenated in the presence of 30 mg of palladium (10% on activated carbon) at RT and standard pressure overnight. The reaction mixture was then filtered through Celite and the residue was washed with ethanol. The combined filtrates were concentrated under reduced pressure and dried. Yield: 214 mg (90% of theory)

LC/MS [Method 5]: $R_t$=1.45 min; MS (ESIpos): m/z=206 (M+H)$^+$, $^1$H-NMR (400 MHz, DMSO-d$_6$): δ [ppm]=8.16 (d, 1H), 8.14 (s, 1H), 6.46 (dd, 1H), 6.32 (d, 1H), 5.84 (s, 2H), 4.24 (q, 2H), 1.28 (t, 3H).

Example 1.3A

Imidazo[1,2-a]pyridine-6-amine

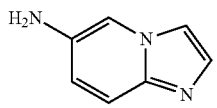

A solution of 600 mg (3.68 mmol) of 6-nitroimidazo[1,2-a]pyridine in 30 ml of ethanol was hydrogenated in the presence of 60 mg of palladium (10% on activated carbon) at RT and standard pressure overnight. The reaction mixture was then filtered through Celite and the residue was washed with ethanol. The combined filtrates were concentrated under reduced pressure and dried. The crude product was used without further purification in the next step. Yield: 512 mg (quant.)

LC/MS [Method 5]: $R_t$=0.89 min; MS (ESIpos): m/z=134 (M+H)$^+$, $^1$H-NMR (400 MHz, DMSO-d$_6$): δ [ppm]=7.72-7.62 (m, 2H), 7.33 (d, 1H), 7.30 (d, 1H), 6.80 (dd, 1H), 4.83 (s, 2H).

Example 1.4A

Ethyl 6-nitroimidazo[1,2-a]pyridine-3-carboxylate

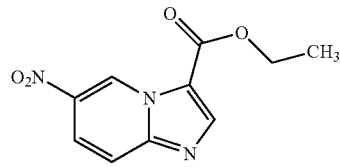 [SMILES: CCOC(=O)c1cnc2ccc([N+](=O)[O-])cn12]

3.00 g (21.6 mmol) of 2-amino-5-nitropyridine and 13.4 g (71.2 mmol, 3.3 eq.) of potassium (1E)-2-chloro-3-ethoxy-3-oxoprop-1-en-1-olate (T. Ikemoto et al., *Tetrahedron* 2000, 56, 7915-7921) were dissolved in 136 ml of ethanol, and 1.91 ml of sulphuric acid were added carefully. The mixture was heated at reflux for 12 h and the precipitate was filtered off and washed with ethanol. The filtrate was concentrated under reduced pressure. The residue was taken up in ethyl acetate and water and acidified slightly with 1M hydrochloric acid. The aqueous phase was then extracted three times with ethyl acetate. The combined organic phases were dried over magnesium sulphate and the solvent was removed under reduced pressure. 3 g of the crude product were purified by flash chromatography (silica gel 50, mobile phase: cyclohexane/ethyl acetate mixtures), giving 720 mg of product (93% pure). The remainder was purified by preparative HPLC (XBridge C18, 5 μM, 100 mm×30 mm, mobile phase: acetonitrile/water 2:3), giving a further 690 mg of product. Yield: 720 mg (93% pure, 13% of theory) and 690 mg (14% of theory)

LC/MS [Method 5]: $R_t$=2.12 min; MS (ESIpos): m/z=236 (M+H)$^+$, $^1$H-NMR (400 MHz, DMSO-d$_6$): δ [ppm]=10.14 (dd, 1H), 8.51 (s, 1H), 8.25 (dd, 1H), 7.98 (dd, 1H), 4.43 (q, 2H), 1.38 (t, 3H).

Example 1.4B

Ethyl 6-aminoimidazo[1,2-a]pyridine-3-carboxylate

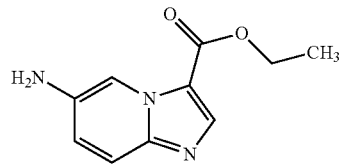

250 mg (1.06 mmol) of ethyl 6-nitroimidazo[1,2-a]pyridine-3-carboxylate were initially charged in 10 ml of ethanol 68 mg (64 μmol, 0.06 eq.) of 10% palladium on activated carbon was added, and the mixture was hydrogenated under standard pressure overnight. The reaction solution was filtered off through kieselguhr and concentrated under reduced pressure. Yield: 217 mg (99% of theory)

LC/MS [Method 1]: $R_t$=0.33 min; MS (ESIpos): m/z=206 (M+H)$^+$, $^1$H-NMR (400 MHz, DMSO-d$_6$): δ [ppm]=8.62 (d, 1H), 8.04 (s, 1H), 7.53 (d, 1H), 7.11 (dd, 1H), 5.35 (s, 2H), 4.32 (q, 2H), 1.33 (t, 3H).

Example 1.5A

7-Nitroimidazo[1,2-a]pyridine-2-carboxamide

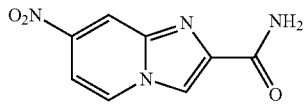 [SMILES: NC(=O)c1cn2ccc([N+](=O)[O-])cc2n1]

16 ml of a methanolic ammonia solution (7N) and 30 ml of ammonia solution (35% in water) were added to 670 mg (2.85 mmol) of ethyl 7-nitroimidazo[1,2-a]pyridine-2-carboxylate. The reaction was divided into 4 aliquots and these were heated in closed vessels in the microwave at 80° C. for 1.5 h. Subsequently, the reaction solutions were combined and taken up in ethyl acetate/water, and the aqueous phase was neutralized with hydrochloric acid (1N). The mixture was extracted twice with ethyl acetate and the combined organic phases were washed with saturated aqueous sodium chloride solution and dried over magnesium sulphate. The solvent was removed under reduced pressure and the crude product was purified by flash chromatography (silica gel 50, dichloromethane/methanol mixtures). Yield 81 mg (91% pure, 12% of theory)

LC/MS [Method 5]: $R_t$=1.40 min; MS (ESIpos): m/z=207 $(M+H)^+$, $^1$H-NMR (400 MHz, DMSO-$d_6$): δ [ppm]=9.92 (dd, 1H), 8.57 (d, 1H), 8.01 (dd, 1H), 7.87 (br. s, 1H), 7.75 (dt, 1H), 7.59 (br. s, 1H).

Example 1.5B

7-Aminoimidazo[1,2-a]pyridine-2-carboxamide

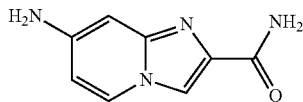

80 mg (91% pure, 0.35 mmol) of 7-nitroimidazo[1,2-a]pyridine-2-carboxamide were initially charged in 15 ml of ethanol 19 mg of palladium (10% on activated carbon) were added and the mixture was hydrogenated at RT and standard pressure for 3 h. The reaction solution was filtered through kieselguhr and the solvent was removed under reduced pressure. Yield 50 mg (90% pure, 73% of theory)

LC/MS [Method 5]: $R_t$=0.95 min; MS (ESIpos): m/z=177 $(M+H)^+$, $^1$H-NMR (400 MHz, DMSO-$d_6$): δ [ppm]=8.10 (d, 1H), 7.68 (dd, 1H), 7.48 (br. s, 1H), 7.33 (d, 1H), 7.18 (br. s, 1H), 6.92 (dd, 1H), 5.02 (s, 2H).

Example 1.6A 2-(4-Fluorophenyl)-6-nitroimidazo[1,2-a]pyridine

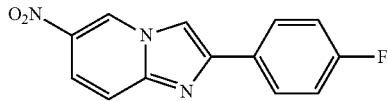

80.6 mg (0.72 mmol, 0.1 eq.) of DABCO and 36 ml of water were added to 1.00 g (7.19 mmol) of 2-amino-5-nitropyridine and 1.56 g (7.19 mmol) of 2-bromo-1-(4-fluorophenyl)ethanone. The mixture was stirred at 65° C. for 2 h and, after stirring overnight at RT, for a further 6 h at 65° C. After 48 h at RT, the resulting precipitate was filtered off with suction, stirred with methyl tert.-butyl ether and filtered off with suction. Yield: 576 mg (purity 92%, 29% of theory)

LC/MS [Method 1]: $R_t$=0.93 min; MS (ESIpos): m/z=258 $(M+H)^+$ $^1$H-NMR (400 MHz, DMSO-$d_6$): δ [ppm]=9.84 (d, 1H), 8.60 (s, 1H), 8.07-8.01 (m, 2H), 7.96 (dd, 1H), 7.74 (d, 1H), 7.36-7.29 (m, 2H).

Example 1.6B 2-(4-Fluorophenyl)imidazo[1,2-a]pyridine-6-amine

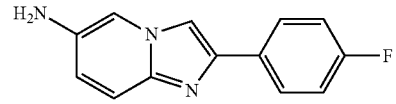

450 mg (92% pure, 1.61 mmol) of 2-(4-fluorophenyl)-6-nitroimidazo[1,2-a]pyridine were initially charged in 20 ml of ethanol. 171 mg (161 μmol, 0.1 eq.) of 10% palladium on activated carbon were added, and the mixture was hydrogenated under standard pressure overnight. The reaction solution was filtered off through kieselguhr and concentrated under reduced pressure. An analogous reaction was carried out using 100 mg of starting material. The products were combined, stirred with methyl tert-butyl ether and filtered off with suction. Yield: 395 mg (purity 80%, 71% of theory)

LC/MS [Method 1]: $R_t$=0.46 min; MS (ESIpos): m/z=228 $(M+H)^+$, $^1$H-NMR (400 MHz, DMSO-$d_6$): δ [ppm]=8.16 (s, 1H), 7.91 (dd, 2H), 7.67 (d, 1H), 7.33 (d, 1H), 7.22 (t, 2H), 6.85 (dd, 1H), 4.95 (br. s, 2H).

Example 1.7A

6-Nitro[1,2,4]triazolo[4,3-a]pyridine

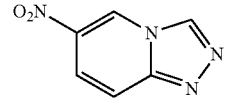

2.00 g (13.0 mmol) of 2-hydrazino-5-nitropyridine were initially charged in 80 ml of dichloromethane, and 5.51 g (51.9 mmol) of trimethyl orthoformate were added. The mixture was left stirring at RT for 15 min 1.00 ml (13.0 mmol) of trifluoroacetic acid was then added, and stirring was continued for 30 min Volatile constituents were then removed under reduced pressure, and the product was purified by flash chromatography (silica gel 50, cyclohexane/ethyl acetate mixtures). Yield: 896 mg (42% of theory)

LC/MS [Method 1]: $R_t$=0.41 min; MS (ESIpos): m/z=165 $(M+H)^+$, $^1$H-NMR (400 MHz, DMSO-$d_6$): δ [ppm]=10.2 (dd, 1H), 8.82 (s, 1H), 8.39 (d, 1H), 8.37 (d, 1H), 8.04 (dd, 2H).

Example 1.7B

[1,2,4]Triazolo[4,3-a]pyridine-6-amine

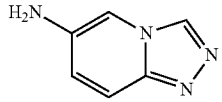

A solution of 890 mg (5.42 mmol) of 6-nitro[1,2,4]triazolo[4,3-a]pyridine in 60 ml of ethanol was hydrogenated in the presence of 577 mg of palladium (10% on activated carbon) at RT and standard pressure for 6 h. The reaction mixture was then filtered through Celite, the same amount of palladium catalyst was added again and the mixture was hydrogenated for a further 2 h. After filtration through Celite, the reaction mixture was concentrated, the residue was crystallized with pentane/methyl tert-butyl ether and the solid was filtered off with suction. Yield: 469 mg (65% of theory)

LC/MS [Method 5]: $R_t$=0.62 min; MS (ESIpos): m/z=135 (M+H)$^+$, $^1$H-NMR (400 MHz, DMSO-d$_6$): δ [ppm]=8.17 (s, 1H), 8.02 (dd, 1H), 7.56 (dd, 1H), 7.19 (dd, 1H), 5.24 (br. s, 2H).

Example 1.8A

3-Methyl-6-nitro[1,2,4]triazolo[4,3-a]pyridine

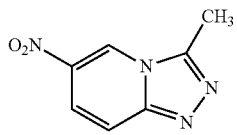

2.00 g (13.0 mmol) of 2-hydrazino-5-nitropyridine were initially charged in 50 ml of ethanol, and 25 ml (195 mmol, 15 eq.) of trimethyl orthoacetate were added. The mixture was heated at reflux for 1 h. The reaction mixture was then concentrated under reduced pressure. The crude product was purified by flash chromatography (silica gel 50, cyclohexane/ethyl acetate mixtures). Yield: 1.81 g (78% of theory)

LC/MS [Method 5]: $R_t$=1.30 min; MS (ESIpos): m/z=179 (M+H)$^+$, $^1$H-NMR (400 MHz, DMSO-d$_6$): δ [ppm]=9.57 (dd, 1H), 7.98 (dd, 1H), 7.87 (d, 1H), 2.81 (s, 3H).

Example 1.8B

3-Methyl[1,2,4]triazolo[4,3-a]pyridine-6-amine

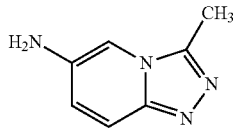

1.27 g (5.61 mmol, 5.0 eq.) of tin(II) chloride dihydrate were added to a suspension of 200 mg (1.12 mmol) of 3-methyl-6-nitro[1,2,4]triazolo[4,3-a]pyridine in 10 ml of ethanol, and the mixture was heated at reflux for 12 h. Saturated aqueous sodium bicarbonate solution was then added and the reaction solution was extracted three times with ethyl acetate. The combined organic phases were dried over magnesium sulphate and concentrated under reduced pressure. Yield: 83 mg (purity 74%, 37% of theory)

LC/MS [Method 5]: $R_t$=0.94 min; MS (ESIpos): m/z=149 (M+H)$^+$.

Example 1.9A

3-Ethyl-6-nitro[1,2,4]triazolo[4,3-a]pyridine

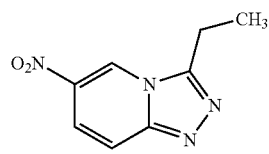

2.00 g (13.0 mmol) of 2-hydrazino-5-nitropyridine were initially charged in 50 ml of ethanol, and 27 ml (195 mmol, 15 eq.) of trimethyl orthopropionate were added. The mixture was heated at reflux for 1 h. The reaction mixture was then concentrated under reduced pressure. The crude product was purified by flash chromatography (silica gel 50, cyclohexane/ethyl acetate mixtures, then ethyl acetate/propanol mixtures). Yield: 2.37 g (95% of theory)

LC/MS [Method 5]: $R_t$=1.42 min; MS (ESIpos): m/z=193 (M+H)$^+$, $^1$H-NMR (400 MHz, DMSO-d$_6$): δ [ppm]=9.58 (dd, 1H), 7.98 (dd, 1H), 7.88 (dd, 1H), 3.22 (q, 3H), 1.40 (t, 4H).

Example 1.9B

3-Ethyl[1,2,4]triazolo[4,3-a]pyridine-6-amine

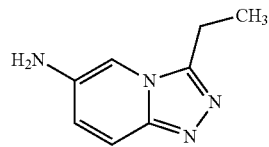

1.00 g (5.20 mmol) of 3-ethyl-6-nitro[1,2,4]triazolo[4,3-a]pyridine was initially charged in 60 ml of ethanol 554 mg (0.52 mmol) of 10% palladium on activated carbon were added, and the mixture was hydrogenated under standard pressure for 4 h. The reaction solution was filtered off through kieselguhr and concentrated under reduced pressure. The crude product was then purified by flash chromatography (silica gel 50, dichloromethane/methanol mixtures). Yield: 600 mg (69% of theory)

LC/MS [Method 5]: $R_t$=1.07 min; MS (ESIpos): m/z=163 (M+H)$^+$, $^1$H-NMR (400 MHz, DMSO-d$_6$): δ [ppm]=7.50 (dd, 1H), 7.35 (dd, 1H), 6.96 (dd, 1H), 5.11 (s, 2H), 2.92 (d, 2H), 1.32 (t, 3H).

Example 1.10A

3-Butyl-6-nitro[1,2,4]triazolo[4,3-a]pyridine

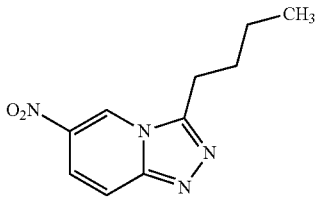 [SMILES: CCCCc1nnc2ccc([N+](=O)[O-])cn12]

1.00 g (6.49 mmol) of 2-hydrazino-5-nitropyridine were initially charged in 13 ml of ethanol, and 2.2 ml (13 mmol, 2 eq.) of trimethyl orthovalerate were added. The mixture was heated at reflux for 1 h. The reaction mixture was then concentrated under reduced pressure. The crude product was purified by flash chromatography (silica gel 50, cyclohexane/ethyl acetate mixtures, then ethyl acetate/2-propanol mixtures). Yield: 1.47 g (99% of theory)

LC/MS [Method 5]: $R_t$=1.86 min; MS (ESIpos): m/z=221 (M+H)$^+$, $^1$H-NMR (400 MHz, DMSO-d$_6$): δ [ppm]=9.62 (dd, 1H), 7.98 (dd, 1H), 7.87 (dd, 1H), 3.22 (t, 2H), 1.81 (quin, 2H), 1.44 (tq, 2H), 0.95 (t, 3H).

Example 1.10B

3-Butyl[1,2,4]triazolo[4,3-a]pyridine-6-amine

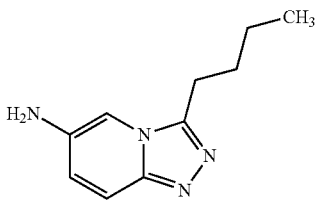

1.20 g (5.45 mmol) of 3-butyl-6-nitro[1,2,4]triazolo[4,3-a]pyridine were initially charged in 65 ml of ethanol. 580 mg (0.55 mmol) of 10% palladium on activated carbon were added, and the mixture was hydrogenated under standard pressure overnight. The reaction solution was filtered off through kieselguhr and concentrated under reduced pressure. The crude product was then purified by flash chromatography (silica gel 50, dichloromethane/methanol mixtures). Yield: 86 mg (purity 85%, 7% of theory)

LC/MS [Method 5]: $R_t$=1.64 min; MS (ESIpos): m/z=191 (M+H)$^+$, $^1$H-NMR (400 MHz, DMSO-d$_6$): δ [ppm]=7.93 (d, 1H), 7.42 (d, 1H), 7.12 (dd, 1H), 5.12 (s, 2H), 2.69 (t, 2H), 1.69 (quin, 2H), 1.34 (tq, 2H), 0.89 (t, 3H).

Example 1.11A 3-(Chloromethyl)-6-nitro[1,2,4]triazolo[4,3-a]pyridine

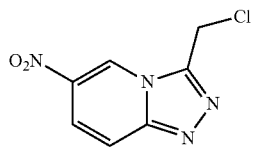 [SMILES: O=[N+]([O-])c1ccc2nnc(CCl)n2c1]

10.0 g (64.9 mmol) of 2-hydrazino-5-nitropyridine were initially charged in 125 ml of ethanol, and 17.5 ml (130 mmol, 2 eq.) of 2-chloro-1,1,1-trimethoxyethane were added. The mixture was heated at reflux for 1 h. The reaction mixture was then concentrated under reduced pressure. The crude product was purified by flash chromatography (silica gel 50, cyclohexane/ethyl acetate mixtures, then ethyl acetate/2-propanol mixtures). Yield: 13.1 g (95% of theory)

LC/MS [Method 1]: $R_t$=0.52 min; MS (ESIpos): m/z=213 (M+H)$^+$, $^1$H-NMR (400 MHz, DMSO-d$_6$): δ [ppm]=9.84 (dd, 1H), 8.12 (dd, 1H), 8.03 (dd, 1H), 5.57 (s, 2H).

Example 1.11B

N,N-Dimethyl-1-(6-nitro[1,2,4]triazolo[4,3-a]pyridin-3-yl)methanamine

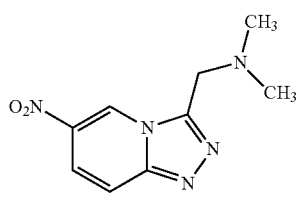 [SMILES: CN(C)Cc1nnc2ccc([N+](=O)[O-])cn12]

200 mg (0.94 mmol) of 3-(chloromethyl)-6-nitro[1,2,4]triazolo[4,3-a]pyridine were dissolved in 2.9 ml of 33% strength dimethylamine solution in ethanol, and the solution was stirred at RT for 4 h. The precipitated solid was then filtered off and dried under reduced pressure. Yield: 148 mg (61% of theory)

LC/MS [Method 5]: $R_t$=1.54 min; MS (ESIpos): m/z=222 (M+H)$^+$, $^1$H-NMR (400 MHz, DMSO-d$_6$): δ [ppm]=10.10 (dd, 1H), 8.35 (dd, 1H), 7.95 (dd, 1H), 3.74 (s, 3H), 2.27 (s, 6H).

Example 1.11C

3-[(Dimethylamino)methyl][1,2,4]triazolo[4,3-a]pyridine-6-amine

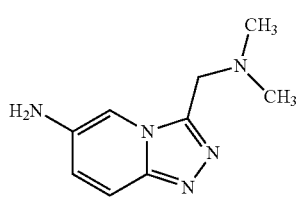

145 mg (0.66 mmol) of N,N-dimethyl-1-(6-nitro[1,2,4]triazolo[4,3-a]pyridin-3-yl)methanamine were initially charged in 10.7 ml of ethanol 15 mg (56 µmol, 0.1 eq., 83% pure) of platinum(IV) dioxide was added, and the mixture was hydrogenated under standard pressure for 4 h. The mixture was then filtered off through kieselguhr and the filtrate was carefully concentrated under reduced pressure. Yield: 115 mg (92% of theory)

LC/MS [Method 5]: $R_t$=1.19 min; MS (ESIpos): m/z=192 (M+H)$^+$, $^1$H-NMR (400 MHz, DMSO-d$_6$): δ [ppm]=7.96 (d, 1H), 7.48 (d, 1H), 7.15 (dd, 1H), 5.18 (s, 2H), 3.55 (s, 2H), 2.22 (s, 6H).

Example 1.12A 3-(Morpholin-4-ylmethyl)-6-nitro[1,2,4]triazolo[4,3-a]pyridine

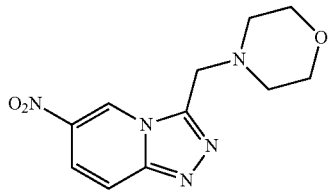 [SMILES: O=[N+]([O-])c1ccc2nnc(CN3CCOCC3)n2c1]

300 g (1.41 mmol) of 3-(chloromethyl)-6-nitro[1,2,4]triazolo[4,3-a]pyridine were dissolved in 2.0 ml of ethanol, and 0.37 ml (4.23 mmol, 3.0 eq.) of morpholine were added. The mixture was left to stir at RT for 4 h and then heated at 50 C for a further 4 h, and ethyl acetate and saturated aqueous sodium bicarbonate solution were added. The aqueous phase was extracted twice with ethyl acetate. The combined organic phases were washed with saturated aqueous sodium chloride solution and concentrated under reduced pressure. Yield: 150 mg (40% of theory)

LC/MS [Method 5]: $R_t$=1.51 min; MS (ESIpos): m/z=264 (M+H)$^+$, $^1$H-NMR (400 MHz, DMSO-d$_6$): δ [ppm]=10.11 (dd, 1H), 8.35 (dd, 1H), 7.95 (dd, 1H), 3.80 (s, 2H), 3.60-3.55 (m, 4H).

Example 1.12B 3-(Morpholin-4-ylmethyl)[1,2,4]triazolo[4,3-a]pyridine-6-amine

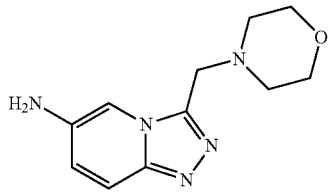

140 mg (0.53 mmol) of 3-(morpholin-4-ylmethyl)-6-nitro[1,2,4]triazolo[4,3-a]pyridine were initially charged in 9.3 ml of ethanol 12 mg (53 µmol, 0.1 eq., 83% pure) of platinum(IV) dioxide were added, and the mixture was hydrogenated under standard pressure for 4 h. The mixture was then filtered off through kieselguhr and the filtrate was carefully concentrated under reduced pressure. Yield: 93 mg (purity 77%, 58% of theory)

LC/MS [Method 5]: $R_t$=1.20 min; MS (ESIpos): m/z=234 (M+H)$^+$, $^1$H-NMR (400 MHz, DMSO-d$_6$): δ [ppm]=7.97 (d, 1H), 7.47 (d, 1H), 7.16 (dd, 1H), 5.20 (br. s, 2H), 3.60 (s, 2H), 3.59-3.51 (m, 8H).

Example 1.13A tert.-Butyl imidazo[1,5-a]pyridin-6-ylcarbamate

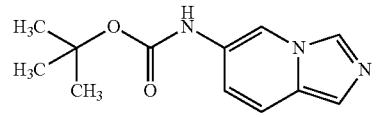 [SMILES: CC(C)(C)OC(=O)Nc1ccc2cncn2c1]

Under argon, a microwave vessel was charged with 200 mg (1.02 mmol) of 6-bromoimidazo[1,5-a]pyridine, 428 mg (3.63 mmol, 3.6 eq.) of tert-butyl carbamate, 16.6 mg (0.07 mmol) of palladium(II) acetate, 58.7 mg (0.10 mmol) of Xantphos, 496 mg (1.52 mmol, 1.5 eq.) of caesium carbonate and 10 ml of 1,4-dioxane. A stream of argon was passed through the suspension for 2 min. The reaction mixture was heated in the microwave at 140° C. for 4 h. After filtration through kieselguhr, the filtrate was concentrated under reduced pressure. The crude product was purified by normal phase chromatography (mobile phase: dichloromethane/methanol (2-5%) mixtures). Yield: 31.5 mg (13% of theory)

LC/MS [Method 1]: $R_t$=0.52 min; MS (ESIpos): m/z=234 (M+H)$^+$, $^1$H-NMR (400 MHz, DMSO-d$_6$): δ [ppm]=9.35 (br. s, 1H), 8.71 (br. s, 1H), 8.33 (s, 1H), 7.46 (d, 1H), 7.26 (s, 1H), 6.70 (dd, 1H), 1.49 (s, 9H).

Example 1.13B

Imidazo[1,5-a]pyridine-6-amine

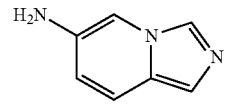

At RT, 1 ml (12.98 mmol) of TFA was added to a solution of 66 mg (0.28 mmol) of tert-butyl imidazo[1,5-a]pyridin-6-ylcarbamate in dichloromethane (2 ml), and the mixture was stirred at RT for 1 h. Subsequently, the reaction mixture was concentrated under reduced pressure. The residue was dissolved in ethyl acetate and washed with saturated aqueous sodium bicarbonate solution. After phase separation, the aqueous phase was dried over sodium sulphate and concentrated under reduced pressure. Yield: 38.9 mg (69% pure, 72% of theory).

LC/MS [Method 5]: $R_t$=1.08 min, MS (ESIpos): m/z=134 (M+H)$^+$.

Example 2.1A 2,5-Dimethoxypyridin-4-ylboronic acid

11.53 g (82.9 mmol) of 2,5-dimethoxypyridine were reacted according to General Method 1A. The desired product precipitated out after acidification of the aqueous phase. Yield: 9.53 g (61% of theory)

LC/MS [Method 1]: $R_t$=0.47 min; MS (ESIpos): m/z=184 (M+H)$^+$.

Example 2.1B

4-Chloro-2-(2,5-dimethoxypyridin-4-yl)benzonitrile

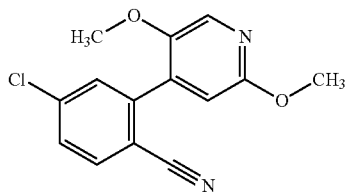 [SMILES: COc1cc(-c2cc(Cl)ccc2C#N)c(OC)cn1]

7.87 g (purity 95%, 40.86 mmol) of 2,5-dimethoxypyridin-4-ylboronic acid and 8.85 g (40.86 mmol) of 2-bromo-4-chlorobenzonitrile in the presence of [1,1-bis(diphenylphosphino)ferrocene]palladium(II) chloride/dichloromethane monoadduct were reacted according to General Method 2A. Yield: 6.23 g (92% pure, 51% of theory).

LC/MS [Method 1]: $R_t$=1.08 min; MS (ESIpos): m/z=275 (M+H)$^+$.

Example 2.1C

4-Chloro-2-(5-methoxy-2-oxo-1,2-dihydropyridin-4-yl)benzonitrile

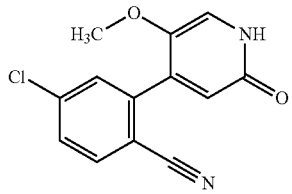 [SMILES: COc1c[nH]c(=O)cc1-c1cc(Cl)ccc1C#N]

7.23 g (purity 92%, 24.21 mmol) of 4-chloro-2-(2,5-dimethoxypyridin-4-yl)benzonitrile and pyridinium hydrochloride were reacted according to General Method 3A. Yield: 6.66 g (91% pure, 96% of theory).

LC/MS [Method 1]: $R_t$=0.76 min; MS (ESIpos): m/z=261 (M+H)$^+$, $^1$H-NMR (400 MHz, DMSO-d$_6$): δ [ppm]=11.45 (br. s, 1H), 7.98 (d, 1H), 7.75-7.67 (m, 2H), 7.29 (br. s, 1H), 6.43 (s, 1H), 3.64 (s, 3H).

Example 2.1D tert-Butyl 2-[4-(5-chloro-2-cyanophenyl)-5-methoxy-2-oxopyridin-1(2H)-yl]butanoate (racemate)

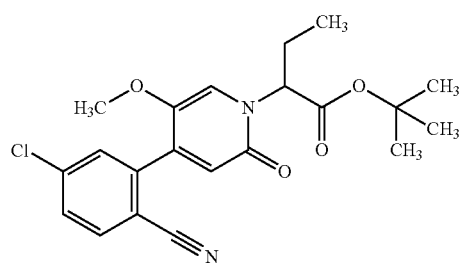 [SMILES: CCC(C(=O)OC(C)(C)C)n1cc(OC)c(-c2cc(Cl)ccc2C#N)cc1=O]

Under argon and at −78° C., 14.0 ml (1.0M in THF, 14.0 mmol, 1.05 eq.) of bis(trimethylsilyl)lithium amide were added dropwise to a solution of 5.0 g (13.3 mmol) of tert-butyl [4-(5-chloro-2-cyanophenyl)-5-methoxy-2-oxopyridin-1(2H)-yl]acetate in 100 ml of tetrahydrofuran, and the mixture was stirred at −78° C. for 15 min. 2.6 g (14.7 mmol, 1.1 eq.) of neat ethyl trifluoromethanesulphonate were then added dropwise. The cooling bath was removed and the reaction mixture was stirred at RT for another 1 h. The reaction mixture was cooled to 0° C., and saturated aqueous ammonium chloride solution was added. After phase separation, the aqueous phase was extracted twice with methyl-tert-butyl ether. The combined organic phases were dried (sodium sulphate), filtered and concentrated under reduced pressure. The crude product was then purified by flash chromatography (340 g of silica gel, mobile phase: cyclohexane/ethyl acetate mixtures 8:1, 4:1). The product-containing fractions were combined and concentrated under reduced pressure. The residue was dissolved in hot methyl tert-butyl ether and the solution was left to stand without any cover, and after 10 min the mixture had crystallized almost completely. The crystals were filtered off and washed twice with methyl tert-butyl ether. The combined filtrates were concentrated under reduced pressure and the residue was re-crystallized as described. The two crystal batches were combined and dried under reduced pressure. Yield: 4.2 g (78% of theory)

LC/MS [Method 1]: $R_t$=1.05 min; MS (ESIpos): m/z=403 (M+H)$^+$, $^1$H-NMR (400 MHz, DMSO-d$_6$): δ [ppm]=7.99 (d, 1H), 7.77-7.70 (m, 2H), 7.36 (s, 1H), 6.50 (s, 1H), 5.03 (dd, 1H), 3.64 (s, 3H), 2.19-2.06 (m, 2H), 1.40 (s, 9H), 0.85 (t, 3H).

Example 2.1E

2-[4-(5-Chloro-2-cyanophenyl)-5-methoxy-2-oxopyridin-1(2H)-yl]butanoic acid (racemate)

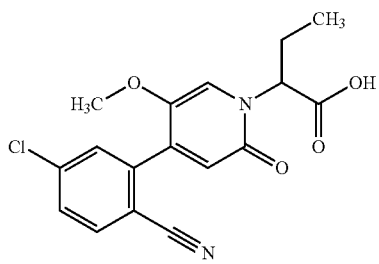 [SMILES: CCC(C(=O)O)n1cc(OC)c(-c2cc(Cl)ccc2C#N)cc1=O]

159 mg (purity 82%, 0.5 mmol) of 4-chloro-2-(5-methoxy-2-oxo-1,2-dihydropyridin-4-yl)benzonitrile and 1.5 eq. of 2-bromobutanoic acid (racemate) were reacted according to General Method 4A at 50° C. Yield: 55 mg (32% of theory)

LC/MS [Method 1]: $R_t$=0.85 min; MS (ESIpos): m/z=347 (M+H)$^+$.

Alternative Synthesis:

Under argon and at RT, 7.8 ml (101.8 mmol, 10 eq.) of trifluoroacetic acid were added to a solution of 4.1 g (10.2 mmol) of tert-butyl 2-[4-(5-chloro-2-cyanophenyl)-5-methoxy-2-oxopyridin-1(2H)-yl]butanoate (racemate) in 40 ml of dichloromethane, the mixture was stirred at RT for 1 h, a further 7.8 ml (101.8 mmol, 10 eq.) of trifluoroacetic acid were added, the mixture was stirred at RT for 1 h, a further 7.8 ml (101.8 mmol, 10 eq.) of trifluoroacetic acid were added and the mixture was stirred at RT for 1 h. Once the reaction had gone to completion, the reaction mixture was concentrated under reduced pressure and the residue was co-evaporated in each case three times with dichloromethane and once with toluene and dried under reduced pressure. The residue was taken up in 100 ml of ethyl acetate and washed repeatedly with a strongly diluted aqueous sodium bicarbonate solution (where the pH of the washing water should not exceed pH 3-4 since otherwise the product is well soluble in water). The organic phase was subsequently dried (sodium sulphate), filtered and concentrated under reduced pressure. The residue was triturated with methyl tert-butyl ether, filtered, washed twice with methyl tert-butyl ether and dried under reduced pressure. Yield: 2.9 g (83% of theory)

LC/MS [Method 1]: $R_t$=0.81 min; MS (ESIpos): m/z=347 (M+H)$^+$, $^1$H-NMR (400 MHz, DMSO-d$_6$): δ [ppm]=12.97 (s, 1H), 7.99 (d, 1H), 7.77-7.70 (m, 2H), 7.41 (s, 1H), 6.49 (s, 1H), 5.09 (dd, 1H), 3.64 (s, 3H), 2.21-2.09 (m, 2H), 0.84 (t, 3H).

Example 2.1F

Methyl 2-({2-[4-(5-chloro-2-cyanophenyl)-5-methoxy-2-oxopyridin-1(2H)-yl]butanoyl}amino)imidazo[1,2-a]pyridine-6-carboxylate (racemate)

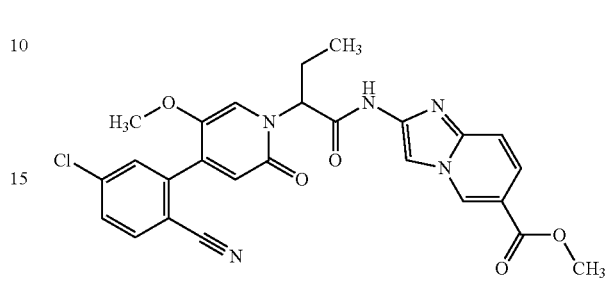

72 mg (0.20 mmol) of 2-[4-(5-chloro-2-cyanophenyl)-5-methoxy-2-oxopyridin-1(2H)-yl]butanoic acid (racemate) and 43 mg (0.22 mmol, 1.1 eq.) of methyl 2-aminoimidazo[1,2-a]pyridine-6-carboxylate were reacted according to General Method 5A. The crude product was purified by preparative HPLC (Reprosil C18, water/acetonitrile gradient). Yield: 59 mg (56% of theory)

LC/MS [Method 1]: $R_t$=1.01 min; MS (ESIpos): m/z=520 (M+H)$^+$.

Example 2.2A

Ethyl 6-({2-[4-(5-chloro-2-cyanophenyl)-5-methoxy-2-oxopyridin-1(2H)-yl]butanoyl}amino)imidazo[1,2-a]pyridine-2-carboxylate (racemate)

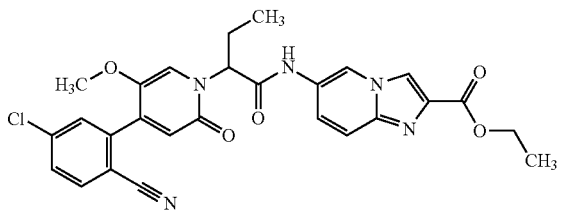 [SMILES: CCOC(=O)c1cn2cc(NC(=O)C(CC)n3cc(OC)c(-c4cc(Cl)ccc4C#N)cc3=O)ccc2n1]

87 mg (0.25 mmol) of 2-[4-(5-chloro-2-cyanophenyl)-5-methoxy-2-oxopyridin-1(2H)-yl]butanoic acid (racemate) and 59 mg (0.28 mmol, 1.1 eq.) of ethyl 6-aminoimidazo[1,2-a]pyridine-2-carboxylate were reacted according to General Method 5A. The crude product was purified by preparative HPLC (Reprosil C18, water/acetonitrile gradient). Yield: 86 mg (64% of theory)

LC/MS [Method 1]: $R_t$=0.96 min; MS (ESIpos): m/z=534 (M+H)$^+$, $^1$H-NMR (400 MHz, DMSO-d$_6$): δ [ppm]=10.76 (s, 1H), 9.32 (s, 1H), 8.61 (s, 1H), 8.00 (d, 1H), 7.78-7.71 (m, 2H), 7.64 (d, 1H), 7.51 (s, 1H), 7.34 (dd, 1H), 6.55 (s, 1H), 5.65 (dd, 1H), 4.30 (q, 2H), 3.70 (s, 3H), 2.28-2.10 (m, 2H), 1.30 (t, 3H), 0.92 (t, 3H).

Example 2.3A

Ethyl 7-({2-[4-(5-chloro-2-cyanophenyl)-5-methoxy-2-oxopyridin-1(2H)-yl]butanoyl}amino)imidazo[1,2-a]pyridine-2-carboxylate (racemate)

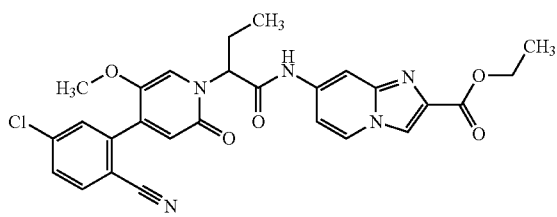 [SMILES: CCOC(=O)c1cn2ccc(NC(=O)C(CC)n3cc(OC)c(-c4cc(Cl)ccc4C#N)cc3=O)cc2n1]

87 mg (0.25 mmol) of 2-[4-(5-chloro-2-cyanophenyl)-5-methoxy-2-oxopyridin-1(2H)-yl]butanoic acid (racemate) and 56 mg (0.28 mmol, 1.1 eq.) of ethyl 7-aminoimidazo[1,2-a]pyridine-2-carboxylate were reacted according to General Method 5A. The crude product was purified by preparative HPLC (Reprosil C18, water/acetonitrile gradient). Yield: 18 mg (13% of theory)

LC/MS [Method 8]: $R_t$=1.11 min; MS (ESIpos): m/z=534 (M+H)$^+$.

Example 3.1A tert-Butyl [4-(5-chloro-2-cyanophenyl)-5-methoxy-2-oxopyridin-1(2H)-yl]acetate

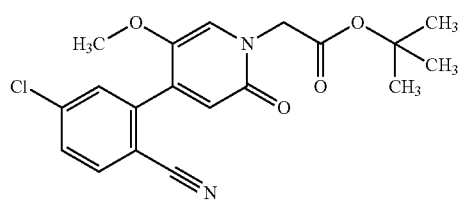 [SMILES: COc1cn(CC(=O)OC(C)(C)C)c(=O)cc1-c1cc(Cl)ccc1C#N]

516 mg (purity 91%, 1.8 mmol) of 4-chloro-2-(5-methoxy-2-oxo-1,2-dihydropyridin-4-yl)benzonitrile and 1.2 eq. of tert-butyl bromoacetate were reacted according to General Method 4B at 100° C. Yield: 464 mg (68% of theory)

LC/MS [Method 1]: $R_t$=1.00 min; MS (ESIpos): m/z=375 (M+H)$^+$.

Example 3.1B

[4-(5-Chloro-2-cyanophenyl)-5-methoxy-2-oxopyridin-1(2H)-yl]acetic acid

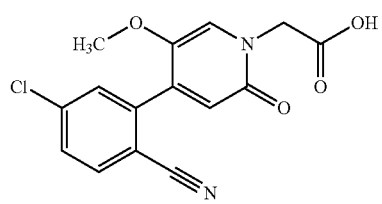 [SMILES: COc1cn(CC(=O)O)c(=O)cc1-c1cc(Cl)ccc1C#N]

187 mg (500 µmol) of tert-butyl [4-(5-chloro-2-cyanophenyl)-5-methoxy-2-oxopyridin-1(2H)-yl]acetate and 770 µl (10.0 mmol) of TFA were reacted according to General Method 6A. Yield: 159 mg (93% of theory)

LC/MS [Method 1]: $R_t$=0.72 min; MS (ESIneg): m/z=317 (M–H)$^-$, $^1$H-NMR (400 MHz, DMSO-d$_6$): δ [ppm]=13.1 (s, 1H), 8.00 (d, 1H), 7.74 (dd, 1H), 7.72 (s, 1H), 7.58 (s, 1H), 6.51 (s, 1H), 4.64 (s, 2H), 3.62 (s, 3H).

Example 3.1C

Ethyl 6-({[4-(5-chloro-2-cyanophenyl)-5-methoxy-2-oxopyridin-1(2H)-yl]acetyl}amino)imidazo[1,2-a]pyridine-2-carboxylate

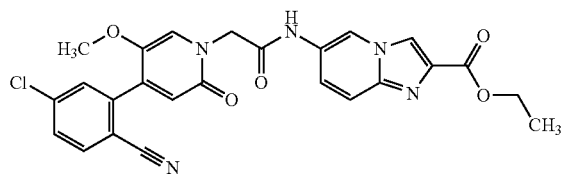 [SMILES: CCOC(=O)c1cn2cc(NC(=O)Cn3cc(OC)c(-c4cc(Cl)ccc4C#N)cc3=O)ccc2n1]

130 mg (0.25 mmol) of [4-(5-chloro-2-cyanophenyl)-5-methoxy-2-oxopyridin-1(2H)-yl]acetic acid and 56 mg (0.28 mmol, 1.1 eq.) of ethyl 6-aminoimidazo[1,2-a]pyridine-2-carboxylate were reacted according to General Method 5A. The crude product was purified by flash chromatography (silica gel (40-60 µm), dichloromethane/methanol 10:1). Yield: 99 mg (48% of theory)

LC/MS [Method 1]: $R_t$=0.83 min; MS (ESIpos): m/z=506 (M+H)$^+$, $^1$H-NMR (400 MHz, DMSO-d$_6$): δ [ppm]=10.65 (s, 1H), 9.30 (s, 1H), 8.62 (s, 1H), 8.01 (d, 1H), 7.70-7.71 (m, 2H), 7.65 (d, 1H), 7.61 (s, 1H), 7.33 (dd, 1H), 6.52 (s, 1H), 4.84 (s, 2H), 4.30 (q, 2H), 3.64 (s, 3H), 1.31 (t, 3H).

Example 4.1A

Ethyl 3-cyclobutyl-2-hydroxypropanoate (racemate)

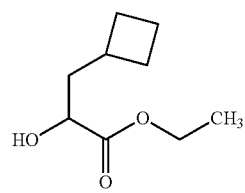

359 mg (14.8 mmol, 1.1 eq.) of magnesium turnings were covered with diethyl ether and etched by addition of a small piece of iodine for 3-4 min Under argon and at RT, 5 ml of a solution of 2.0 g (13.4 mmol) of (bromomethyl)cyclobutane in 30 ml of diethyl ether were added with stirring to this mixture, the mixture was stirred for 5 min (until the reaction is initiated) and the remainder of the (bromomethyl)cyclobutane/diethyl ether solution is added dropwise over a further 10 min. The reaction mixture was stirred under reflux for 1 h, cooled under a stream of argon and, with ice-water cooling, added dropwise to a solution of 2.4 ml (12.1 mmol, 0.9 eq.) of ethyl glyoxylate (50% in toluene). The reaction mixture was stirred at RT for 1 h, carefully quenched to pH 7 with 20 ml of a potassium citrate/citric acid solution (pH 5) and then adjusted to pH 4-5 with aqueous hydrochloric acid (1N). After phase separation, the aqueous phase was extracted with diethyl ether. The combined organic phases were dried (sodium sulphate), filtered and concentrated under reduced pressure. The residue was purified by flash chromatography (silica gel 50, mobile phase: cyclohexane/ethyl acetate 20%-33%). Yield: 110 mg (purity 94%, 5% of theory)

LC-MS [Method 8]: $R_t$=3.37 min; MS (ESIpos): m/z=172 (M)$^+$.

Example 4.1B

Ethyl 3-cyclobutyl-2-{[(trifluoromethyl)sulphonyl]oxy}propanoate (racemate)

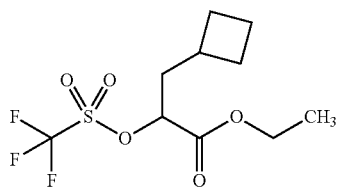 [SMILES: CCOC(=O)C(CC1CCC1)OS(=O)(=O)C(F)(F)F]

110 mg (purity 94%, 0.60 mmol) of ethyl 3-cyclobutyl-2-hydroxypropanoate (racemate) and 142 μl (0.84 mmol, 1.4 eq.) of trifluoromethanesulphonic anhydride in the presence of 105 μl (0.90 mmol, 1.5 eq.) of 2,6-dimethylpyridine were reacted according to General Method 7A. The crude product was reacted in the next step without further purification.

Example 4.1C

Ethyl 2-[4-(5-chloro-2-cyanophenyl)-5-methoxy-2-oxopyridin-1(2H)-yl]-3-cyclobutylpropanoate (racemate)

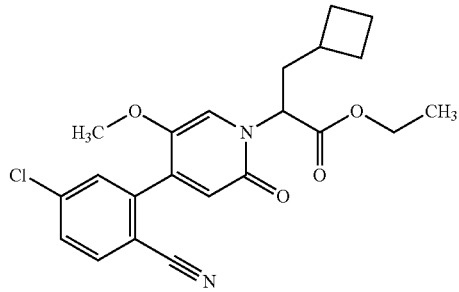 [SMILES: CCOC(=O)C(CC1CCC1)n1cc(OC)c(-c2cc(Cl)ccc2C#N)cc1=O]

122 mg (purity 87%, 0.41 mmol) of 4-chloro-2-(5-methoxy-2-oxo-1,2-dihydropyridin-4-yl)benzonitrile in the presence of 1.3 eq. of sodium hydride and 161 mg (0.53 mmol, 1.3 eq.) of ethyl 3-cyclobutyl-2-{[(trifluoromethyl)sulphonyl]oxy}propanoate (racemate) were reacted at RT according to General Method 4C. The crude product was purified by flash chromatography (KP-SIL, cyclohexane/ethyl acetate 15-33%). Yield: 140 mg (82% of theory)

LC/MS [Method 1]: $R_t$=1.15 min; MS (ESIpos): m/z=415 (M+H)$^+$, $^1$H-NMR (400 MHz, DMSO-d$_6$): δ [ppm]=7.99 (d, 1H), 7.78-7.69 (m, 2H), 7.42 (s, 1H), 6.48 (s, 1H), 5.12 (dd, 1H), 4.21-4.07 (m, 2H), 3.64 (s, 3H), 2.38-2.24 (m, 1H), 2.23-2.11 (m, 2H), 2.05-1.93 (m, 1H), 1.89-1.61 (m, 4H), 1.60-1.47 (m, 1H), 1.18 (t, 3H).

Example 4.1D

2-[4-(5-Chloro-2-cyanophenyl)-5-methoxy-2-oxopyridin-1(2H)-yl]-3-cyclobutylpropanoic acid (racemate)

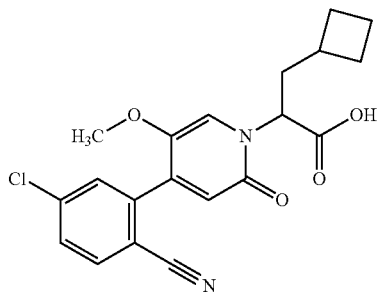 [SMILES: COc1cn(C(CC2CCC2)C(=O)O)c(=O)cc1-c1cc(Cl)ccc1C#N]

138 mg (0.33 mmol) of ethyl 2-[4-(5-chloro-2-cyanophenyl)-5-methoxy-2-oxopyridin-1(2H)-yl]-3-cyclobutylpropanoate (racemate) were hydrolysed with lithium hydroxide according to General Method 6B. Yield: 104 mg (82% of theory)

LC/MS [Method 1]: $R_t$=0.95 min; MS (ESIpos): m/z=387 (M+H)$^+$.

Example 4.1E

Ethyl 6-({2-[4-(5-chloro-2-cyanophenyl)-5-methoxy-2-oxopyridin-1(2H)-yl]-3-cyclobutylpropanoyl}amino)imidazo[1,2-a]pyridine-2-carboxylate (racemate)

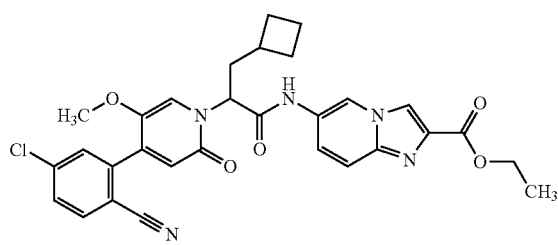 [SMILES: CCOC(=O)c1cn2cc(NC(=O)C(CC3CCC3)n3cc(OC)c(-c4cc(Cl)ccc4C#N)cc3=O)ccc2n1]

109 mg (0.28 mmol) of 2-[4-(5-chloro-2-cyanophenyl)-5-methoxy-2-oxopyridin-1(2H)-yl]cyclobutylpropanoic acid (racemate) and 64 mg (0.31 mmol, 1.1 eq.) of ethyl 6-aminoimidazo[1,2-a]pyridine-2-carboxylate were reacted according to General Method 5A. The crude product was purified by preparative HPLC (Reprosil C18, water/acetonitrile gradient). Yield: 69 mg (43% of theory)

LC/MS [Method 1]: $R_t$=1.08 min; MS (ESIpos): m/z=574 (M+H)$^+$.

Example 5.1A

2-Bromo-4-chlorophenyl difluormethyl ether

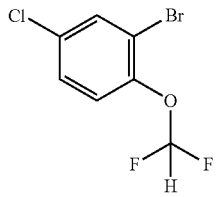 [SMILES: FC(F)Oc1ccc(Cl)cc1Br]

36 ml of aqueous potassium hydroxide solution (6M) were added to a solution of 3.5 g (16.9 mmol) of 2-bromo-4-chlorophenol in 36 ml of acetonitrile, the mixture was cooled in an ice bath and 6.5 ml (26.9 mmol, 1.6 eq.) of difluoromethyl trifluormethanesulphonate [*Angew. Chem. Int. Ed.* 2013, 52, 1-5; *Journal of Fluorine Chemistry* 2009, 130, 667-670] were added dropwise with vigorous stirring. The reaction mixture was stirred for 5 min and diluted with 200 ml of water. The aqueous phase was extracted twice with in each case 150 ml of diethyl ether. The combined organic phases were dried (sodium sulphate), filtered, concentrated under reduced pressure and dried. The aqueous phase was once more extracted with diethyl ether. The organic phase was dried (sodium sulphate), filtered, concentrated under reduced pressure and dried. Yield of the two combined residues: 3.4 g (80% of theory)

LC/MS [Method 9]: $R_t$=3.51 min; MS (ESIpos): m/z=256 (M+H)$^+$, $^1$H-NMR (400 MHz, DMSO-d$_6$): δ [ppm]=7.91 (d, 1H), 7.55 (dd, 1H), 7.37 (d, 1H), 7.30 (t, 1H).

Example 5.1B

4-[5-Chloro-2-(difluoromethoxy)phenyl]-2,5-dimethoxypyridine

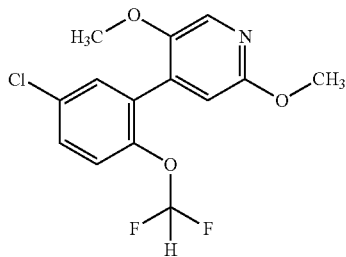 [SMILES: COc1cc(-c2cc(Cl)ccc2OC(F)F)c(OC)cn1]

417 mg (2.19 mmol, 1.2 eq.) of 2,5-dimethoxypyridin-4-ylboronic acid and 494 mg (1.82 mmol) of 2-bromo-4-chlorophenyl difluormethyl ether in the presence of [1,1-bis(diphenylphosphino)ferrocene]palladium(II) chloride/dichloromethane monoadduct were reacted according to General Method 2A. The crude product was purified by flash chromatography (KP-SIL, petroleum ether/ethyl acetate 15-20%). Yield: 170 mg (90% pure, 27% of theory)

LC/MS [Method 1]: $R_t$=1.16 min; MS (ESIpos): m/z=316 (M+H)$^+$, $^1$H-NMR (400 MHz, DMSO-d$_6$): δ [ppm]=7.96 (s, 1H), 7.57 (dd, 1H), 7.45 (d, 1H), 7.30 (d, 1H), 7.11 (t, 1H), 6.74 (s, 1H), 3.83 (s, 3H), 3.75 (s, 3H).

Example 5.1C

4-[5-Chloro-2-(difluoromethoxy)phenyl]-5-methoxypyridin-2(1H)-one

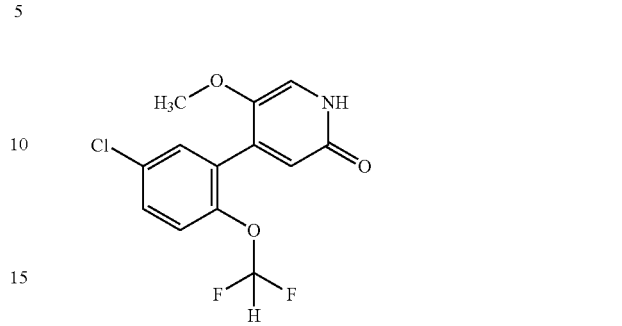

170 mg (purity 90%, 0.49 mmol) of 4-[5-chloro-2-(difluoromethoxy)phenyl]-2,5-dimethoxypyridine and pyridinium hydrobromide were reacted according to General Method 3A. Yield: 127 mg (87% of theory)

LC/MS [Method 1]: $R_t$=0.84 min; MS (ESIpos): m/z=302 (M+H)$^+$.

Example 5.1D

Ethyl 2-{4-[5-chloro-2-(difluoromethoxy)phenyl]-5-methoxy-2-oxopyridine-1(2H)-yl}butanoate (racemate)

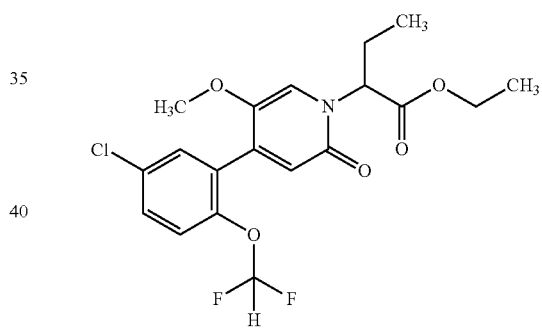

Under argon and at RT, 105 mg (2.64 mmol, 1.3 eq.) of sodium hydride (60% in mineral oil) were added to a solution of 618 mg (2.03 mmol) of 4-[5-chloro-2-(difluoromethoxy)phenyl]-5-methoxypyridin-2(1H)-one in 25 ml of tetrahydrofuran, the mixture was stirred at RT for 60 min, 871 mg (2.64 mmol, 1.3 eq.) of ethyl 2-{[(trifluoromethyl)sulphonyl]oxy}butanoate (racemate) [J. Castells et al. *Tetrahedron*, 1994, 50, 13765-13774] were then added dropwise and the mixture was stirred at RT for 1 h. A further 38 mg (0.96 mmol) of sodium hydride (60% in mineral oil) were added, the mixture was stirred at RT for 5 min, a further 871 mg (2.64 mmol, 1.3 eq.) of ethyl 2-{[(trifluoromethyl)sulphonyl]oxy}butanoate (racemate) were added dropwise, and the reaction mixture was stirred at RT for 15 min and then quenched with water. After phase separation, the aqueous phase was extracted twice with ethyl acetate. The combined organic phases were washed with saturated aqueous sodium chloride solution, dried (sodium sulphate), filtered and concentrated under reduced pressure. The residue was purified by flash chromatography (silica gel 50, cyclohexane/ethyl acetate gradient). Yield: 415 mg (48% of theory)

LC/MS [Method 1]: $R_t$=1.08 min; MS (ESIpos): m/z=416 (M+H)$^+$.

Example 5.1E

2-{4-[5-Chloro-2-(difluoromethoxy)phenyl]-5-methoxy-2-oxopyridine-1(2H)-yl}butanoic acid (racemate)

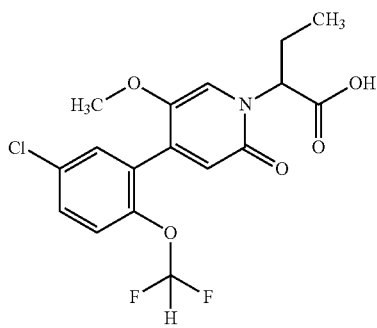 [SMILES: CCC(C(=O)O)n1cc(OC)c(-c2cc(Cl)ccc2OC(F)F)cc1=O]

415 mg (0.97 mmol) of ethyl 2-{4-[5-Chloro-2-(difluormethoxy)phenyl]-5-methoxy-2-oxopyridin-1(2H)-yl}butanoate (racemate) were hydrolysed with lithium hydroxide according to General Method 6B. Yield: 348 mg (93% of theory)

LC/MS [Method 1]: $R_t$=0.91 min; MS (ESIpos): m/z=388 (M+H)$^+$, $^1$H-NMR (400 MHz, DMSO-d$_6$): δ [ppm]=12.96 (br. s, 1H), 7.57 (dd, 1H), 7.50 (d, 1H), 7.34-7.25 (m, 2H), 7.12 (t, 1H), 6.35 (s, 1H), 5.06 (dd, 1H), 3.58 (s, 3H), 2.20-2.06 (m, 2H), 0.82 (t, 3H).

Example 5.1F

Ethyl 6-[(2-{4-[5-chloro-2-(difluoromethoxy)phenyl]-5-methoxy-2-oxopyridin-1(2H)-yl}butanoyl)amino]-imidazo[1,2-a]pyridine-2-carboxylate (racemate)

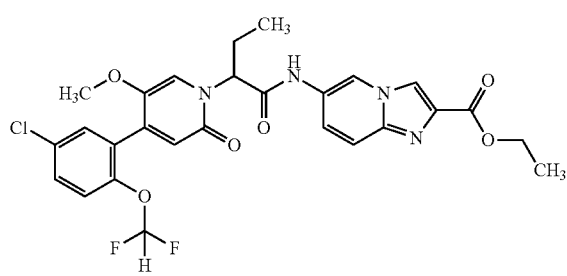 [SMILES: CCOC(=O)c1cn2cc(NC(=O)C(CC)n3cc(OC)c(-c4cc(Cl)ccc4OC(F)F)cc3=O)ccc2n1]

116 mg (0.30 mmol) of 2-{4-[5-chloro-2-(difluoromethoxy)phenyl]-5-methoxy-2-oxopyridin-1(2H)-yl}butanoic acid (racemate) and 69 mg (0.33 mmol, 1.1 eq.) of ethyl 6-aminoimidazo[1,2-a]pyridine-2-carboxylate were reacted according to General Method 5A. Yield: 198 mg (quant.)

LC/MS [Method 1]: $R_t$=1.03 min; MS (ESIpos): m/z=575 (M+H)$^+$.

Example 6.1A (5-Chloro-2-methoxypyridin-4-yl)boronic acid

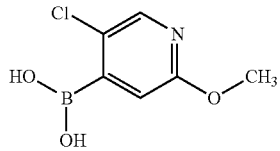

10.0 g of 5-chloro-2-methoxypyridine were initially charged in 225 ml of THF, and 41.8 ml (83.6 mmol) of lithium diisopropylamide (2M in THF/heptane/ethylbenzene) were added at −78° C. The mixture was stirred at −78° C. for 4 h, and 32.6 ml (141 mmol) of triisopropyl borate were then added rapidly. The reaction mixture was stirred at −78° C. for 3 h and then warmed to room temperature overnight. The procedure was then repeated, and a further 20.9 ml (41.8 mmol) of lithium diisopropylamide (2M in THF/heptane/ethylbenzene) and 16.1 ml (69.7 mmol) of triisopropyl borate were added. The reaction mixture was poured into 500 ml of water and THF was removed under reduced pressure. The aqueous phase was extracted three times with ethyl acetate. The aqueous phase was acidified with hydrochloric acid (2N) and the precipitate was filtered off. The filtrate was extracted twice with ethyl acetate, the organic phase was dried and filtered, the solvent was removed under reduced pressure and the residue, together with the precipitate, was dried under high vacuum. Yield: 10.4 g (91% pure, 73% of theory).

LC/MS [Method 1]: $R_t$=0.50 min; MS (ESIpos): m/z=188 (M+H)$^+$, $^1$H-NMR (400 MHz, DMSO-d$_6$): δ [ppm]=8.64 (br. s, 2H), 8.12 (s, 1H), 6.81 (s, 1H), 3.82 (s, 3H).

Example 6.1B

5-Chloro-4-[5-chloro-2-(difluoromethoxy)phenyl]-2-methoxypyridine

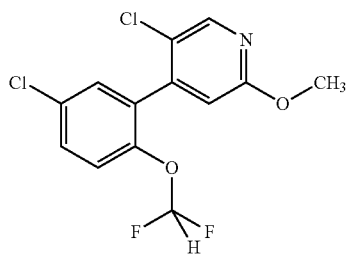 [SMILES: COc1cc(-c2cc(Cl)ccc2OC(F)F)c(Cl)cn1]

At 60° C., 4.17 g (16.2 mmol) of 2-bromo-4-chloro-1-(difluoromethoxy)benzene, 3.04 g (16.2 mmol) of (5-chloro-2-methoxypyridin-4-yl)boronic acid, 561 mg (486 µmol) of CATAXCium A precatalyst and 133 ml of aqueous potassium phosphate solution (0.5N) were stirred in 73 ml of THF for 1 h. The reaction mixture was then diluted with 125 ml of water and 125 ml of ethyl acetate. The phases were separated and the aqueous phase was extracted with 125 ml of ethyl acetate. The combined organic phases were washed with saturated aqueous sodium chloride solution, dried over sodium sulphate and filtered, and the solvent was removed under reduced pressure. Purification by column chromatography of the crude product (100 g silica cartridge, flow rate: 50 ml/min, cyclohexane/ethyl acetate gradient) gave the title compound. Yield: 2.80 g (86% pure, 46% of theory).

LC/MS [Method 1]: $R_t$=1.20 min; MS (ESIpos): m/z=320 (M+H)$^+$.

Example 6.1C

5-Chloro-4-[5-chloro-2-(difluoromethoxy)phenyl]pyridin-2(1H)-one

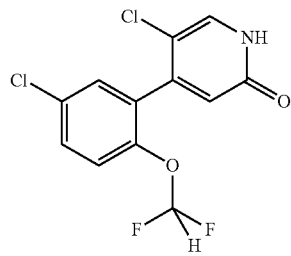 [SMILES: O=c1cc(-c2cc(Cl)ccc2OC(F)F)c(Cl)c[nH]1]

2.80 g (8.75 mmol) of 5-chloro-4-[5-chloro-2-(difluoromethoxy)phenyl]-2-methoxypyridine and 28.0 g (175 mmol) of pyridinium hydrobromide were dissolved in 93.5 ml of dimethylformamide, and the mixture was stirred at 100° C. for 6 h. The solvent was removed under reduced pressure and the residue stirred with 253 ml of water. The precipitate was filtered off with suction, washed with water and then dried. Yield: 2.60 g (81% pure, 79% of theory).

LC/MS [Method 1]: $R_t$=0.85 min; MS (ESIpos): m/z=306 (M+H)$^+$, $^1$H-NMR (400 MHz, DMSO-d$_6$): δ [ppm]=11.99 (br. s, 1H), 7.81 (s, 1H), 7.61 (dd, 1H), 7.49 (d, 1H), 7.34 (d, 1H), 7.20 (t, 1H), 6.44 (s, 1H).

Example 6.1D tert-Butyl {5-chloro-4-[5-chloro-2-(difluoromethoxy)phenyl]-2-oxopyridin-1(2H)-yl}acetate

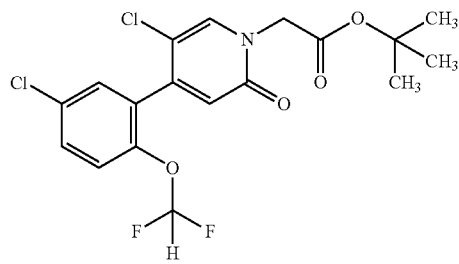 [SMILES: CC(C)(C)OC(=O)Cn1cc(Cl)c(-c2cc(Cl)ccc2OC(F)F)cc1=O]

2.60 g (81% pure, 6.88 mmol) of 5-chlor-4-[5-chloro-2-(difluormethoxy)phenyl]pyridin-2(1H)-one and 1.2 eq. of tert-butyl bromoacetate in the presence of 1.5 eq. of potassium carbonate were reacted according to General Method 4B at 100° C. Yield: 2.44 g (84% of theory)

LC/MS [Method 8]: $R_t$=1.41 min; MS (ESIneg): m/z=418 (M−H)$^-$, $^1$H-NMR (400 MHz, DMSO-d$_6$): δ [ppm]=8.09 (s, 1H), 7.63 (dd, 1H), 7.51 (d, 1H), 7.35 (d, 1H), 7.23 (t, 1H), 6.50 (s, 1H), 4.62 (s, 2H), 1.44 (s, 9H).

Example 6.1E

{5-Chloro-4-[5-chloro-2-(difluoromethoxy)phenyl]-2-oxopyridin-1(2H)-yl}acetic acid

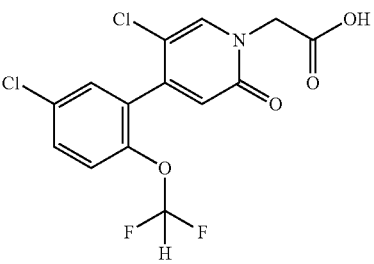 [SMILES: O=C(O)Cn1cc(Cl)c(-c2cc(Cl)ccc2OC(F)F)cc1=O]

126 mg (0.30 mmol) of tert-butyl {5-chloro-4-[5-chloro-2-(difluoromethoxy)phenyl]-2-oxopyridin-1(2H)-yl}acetate and 0.46 ml (6.0 mmol) of TFA were reacted according to General Method 6A. Yield: 101 mg (92% of theory)

LC/MS [Method 1]: $R_t$=0.85 min; MS (ESIpos): m/z=364 (M+H)$^+$.

Example 6.1F

Ethyl 6-[({5-chloro-4-[5-chloro-2-(difluoromethoxy)phenyl]-2-oxopyridin-1(2H)-yl}acetyl)amino]imidazo[1,2-a]pyridine-2-carboxylate

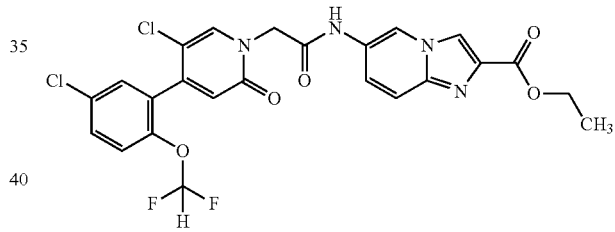

101 mg (0.28 mmol) of {5-chloro-4-[5-chloro-2-(difluoromethoxy)phenyl]-2-oxopyridin-1(2H)-yl}acetic acid and 63 mg (0.31 mmol, 1.1 eq.) of ethyl 6-aminoimidazo[1,2-a]pyridine-2-carboxylate were reacted according to General Method 5A. Yield: 99 mg (65% of theory)

LC/MS [Method 1]: $R_t$=0.93 min; MS (ESIpos): m/z=551 (M+H)$^+$.

Example 7.1A

2-[(Benzyloxy)methyl]tetrahydro-2H-pyran (racemate)

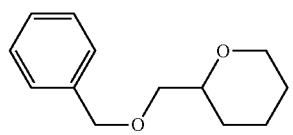

At 0° C., a solution of 25.0 g (215 mmol) of tetrahydro-2H-pyran-2-ylmethanol (racemate) in 500 ml of THF was slowly added dropwise to a suspension of 9.47 g (237 mmol, 60% in mineral oil) of sodium hydride in 500 ml of THF, and after the addition had ended, the mixture was stirred at 0° C. for another 30 min 25.7 ml (215 mmol) of benzyl bromide were then added, and the mixture was stirred at 0° C. for another 30 min and at room temperature for another 1 h. The reaction was terminated by addition of 200 ml of saturated aqueous ammonium chloride solution, and the phases were separated. The aqueous phase was extracted twice with 200 ml of methyl tert-butyl ether. The combined organic phases were dried over magnesium sulphate and filtered, and the solvent was removed under reduced pressure. The crude product was purified by column chromatography (ethyl acetate/cyclohexane gradient, 340 g silica cartridge, flow rate: 100 ml/min), giving the title compound. Yield: 41.9 g (94% of theory)

LC/MS [Method 3]: $R_t$=2.18 min; MS (ESIpos): m/z=207 (M+H)$^+$, $^1$H-NMR (400 MHz, DMSO-d$_6$): δ [ppm]=7.37-7.25 (m, 5H), 4.47 (s, 2H), 3.87-3.81 (m, 1H), 3.47-3.28 (m, 4H), 1.80-1.72 (m, 1H), 1.58-1.37 (m, 4H), 1.25-1.13 (m, 1H).

Example 7.1B (R)-2-[(Benzyloxy)methyl]tetrahydro-2H-pyran

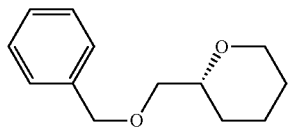 [SMILES: c1ccc(COC[C@H]2CCCCO2)cc1]

Enantiomer separation of 41.9 g of the racemate from Example 7.1A gave 16.7 g of the title compound Example 7.1B (enantiomer 1): Chiral HPLC: $R_t$=5.28 min; 99% ee, purity 93%.

optical rotation: $[α]_{589}^{20.0}$=+14.9° (c 0.43 g/100 cm$^3$, chloroform)

Separating method: Column: OD-H 5 μm 250 mm×20 mm; mobile phase: 95% isohexane, 5% 2-propanol; temperature: 25° C.; flow rate: 25 ml/min; UV detection: 210 nm.

Analysis: Column: OD-H 5 μm 250 mm×4.6 mm; mobile phase: 95% isohexane, 5% 2-propanol; flow rate: 1 ml/min; UV detection: 220 nm.

Example 7.2B (S)-2-[(Benzyloxy)methyl]tetrahydro-2H-pyran

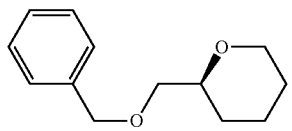 [SMILES: c1ccc(COC[C@@H]2CCCCO2)cc1]

Enantiomer separation of 41.9 g of the racemate from Example 7.1A gave 17.0 g of the title compound Example 7.2B (enantiomer 2): Chiral HPLC: $R_t$=7.36 min; 96% ee, purity 96%.

optical rotation: $[α]_{589}^{20.0}$=−13.9° (c 0.61 g/100 cm$^3$, chloroform)

Separating method: Column: OD-H 5 μm 250 mm×20 mm; mobile phase: 95% isohexane, 5% 2-propanol; temperature: 25° C.; flow rate: 25 ml/min; UV detection: 210 nm.

Analysis: Column: OD-H 5 μm 250 mm×4.6 mm; mobile phase: 95% isohexane, 5% 2-propanol; flow rate: 1 ml/min; UV detection: 220 nm.

Example 7.1C (2S)-Tetrahydro-2H-pyran-2-ylmethanol

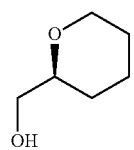

3.51 g (3.30 mmol) of palladium on carbon (10%) were added to a solution of 17.0 g (82.4 mmol) of (S)-2-[(benzyloxy)methyl]tetrahydro-2H-pyran (96% ee, purity 96%) in 120 ml of ethanol, and the mixture was hydrogenated at room temperature and under standard pressure overnight. Another 1.75 g (1.65 mmol) of palladium on carbon (10%) were then added, and the mixture was hydrogenated at room temperature for a further 72 h. Subsequently, the reaction mixture was filtered through Celite and the filtrate was concentrated. The residue was purified chromatographically (silica, dichloromethane/methanol gradient) and the product fractions were freed from the solvent at <25° C. and >50 mbar. Yield: 8.23 g (86% of theory)

optical rotation: $[α]_{589}^{20.0}$=+9.1° (c 0.36 g/100 cm$^3$, chloroform), cf. A. Aponick, B. Biannic, *Org. Lett.* 2011, 13, 1330-1333.

GC/MS [Method 7]: $R_t$=1.82 min; MS: m/z=116 (M)$^+$, $^1$H-NMR (400 MHz, DMSO-d$_6$): δ [ppm]=4.51 (t, 1H), 3.87-3.81 (m, 1H), 3.37-3.18 (m, 4H), 1.80-1.71 (m, 1H), 1.59-1.50 (m, 1H), 1.49-1.36 (m, 3H), 1.19-1.05 (m, 1H).

Example 7.1D (2S)-Tetrahydro-2H-pyran-2-ylmethyl trifluoromethanesulphonate

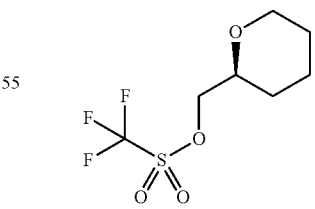

330 mg (2.84 mmol) of (2S)-tetrahydro-2H-pyran-2-yl-methanol and 0.57 ml (3.41 mmol, 1.2 eq.) of trifluoromethanesulphonic anhydride in the presence of 0.48 ml (3.41 mmol, 1.2 eq.) of triethylamine were reacted according to General Method 7A. The crude product was reacted in the next step without further purification.

¹H-NMR (400 MHz, DMSO-d₆): δ [ppm]=4.32 (dd, 1H), 4.18 (dd, 1H), 4.00-3.92 (m, 1H), 3.60-3.52 (m, 1H), 3.48-3.39 (m, 1H), 1.85-1.74 (m, 1H), 1.56-1.41 (m, 4H), 1.28-1.14 (m, 1H).

Example 7.1E tert-Butyl 2-[4-(5-chloro-2-cyanophenyl)-5-methoxy-2-oxopyridin-1(2H)-yl]-3-[(2S)-tetrahydro-2H-pyran-2-yl]propanoate (mixture of enantiomerically pure diastereomers)

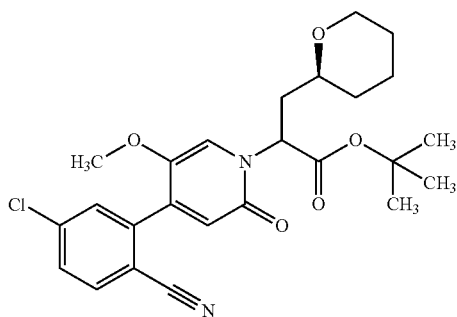 [SMILES: COc1cn(C(C[C@@H]2CCCCO2)C(=O)OC(C)(C)C)c(=O)cc1-c1cc(Cl)ccc1C#N]

4.10 g (10.9 mmol) of tert-butyl [4-(5-chloro-2-cyanophenyl)-5-methoxy-2-oxopyridin-1(2H)-yl]acetate, 4.07 g (16.4 mmol) of (2S)-tetrahydro-2H-pyran-2-ylmethyl trifluoromethanesulphonate and 12.0 ml (12.0 mmol) of bis(trimethylsilyl)lithium amide (1M in THF) in 90 ml of THF were reacted according to General Method 8A. After aqueous work-up, the crude product was purified by flash chromatography (340 g silica cartridge, flow rate: 100 ml/min, cyclohexane/ethyl acetate gradient). Yield: 4.2 g (81% of theory)

LC/MS [Method 1]: $R_t$=1.15 min; MS (ESIpos): m/z=473 (M+H)⁺.

Example 7.1F

2-[4-(5-Chloro-2-cyanophenyl)-5-methoxy-2-oxopyridin-1(2H)-yl]-3-[(2S)-tetrahydro-2H-pyran-2-yl]propanoic acid (mixture of enantiomerically pure diastereomers)

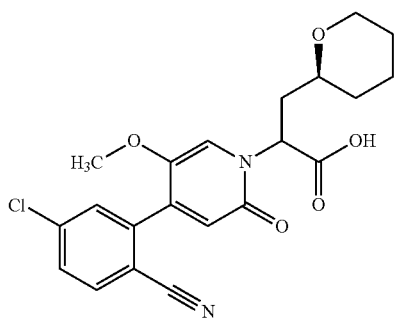 [SMILES: COc1cn(C(C[C@@H]2CCCCO2)C(=O)O)c(=O)cc1-c1cc(Cl)ccc1C#N]

9.8 g (20.7 mmol) of tert-butyl 2-[4-(5-chloro-2-cyanophenyl)-5-methoxy-2-oxopyridin-1(2H)-yl]-3-[(2S)-tetrahydro-2H-pyran-2-yl]propanoate (mixture of enantiomerically pure diastereomers) in 245 ml of dichloromethane and 59.9 ml (777 mmol) of TFA were reacted according to General Method 6A. Yield: 8.7 g (73% pure, 74% of theory).

LC/MS [Method 1]: $R_t$=0.92 min; MS (ESIpos): m/z=417 (M+H)⁺.

Example 7.1G

Ethyl 6-({2-[4-(5-chloro-2-cyanophenyl)-5-methoxy-2-oxopyridin-1(2H)-yl]-3-[(2S)-tetrahydro-2H-pyran-2-yl]propanoyl}amino)imidazo[1,2-a]pyridine-2-carboxylate (mixture of enantiomerically pure diastereomers)

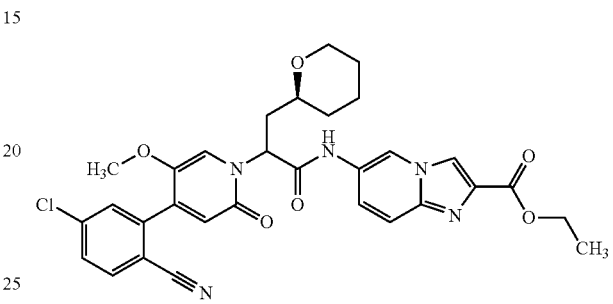

126 mg (0.30 mmol) of 2-[4-(5-chloro-2-cyanophenyl)-5-methoxy-2-oxopyridin-1(2H)-yl]-3-[(2S)-tetrahydro-2H-pyran-2-yl]propanoic acid (mixture of enantiomerically pure diastereomers) and 68 mg (0.33 mmol, 1.1 eq.) of ethyl 6-aminoimidazo[1,2-a]pyridine-2-carboxylate were reacted according to General Method 5A. After removal of the dimethylformamide under reduced pressure, it was possible to crystallize the title compound from the residue using water. The precipitate was filtered off, washed with water and dried under reduced pressure. Yield: 162 mg (89% of theory) LC/MS [Method 1]: $R_t$=0.99 min; MS (ESIpos): m/z=604 (M+H)⁺.

Example 8.1A

2-Methoxyethyl trifluoromethanesulphonate

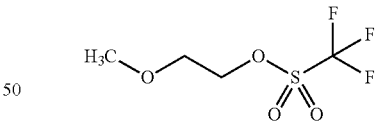

At −78° C., 16.3 g (57.8 mmol) of trifluoromethanesulphonic anhydride were initially charged in 20 ml of dichloromethane, and a solution of 4.00 g (52.6 mmol) of 2-methoxyethanol and 5.85 g (57.8 mmol) of triethylamine in 20 ml of dichloromethane was slowly added dropwise such that the internal temperature did not exceed −50° C. The mixture was left to stir at −78° C. for 15 min and then warmed to RT. The mixture was diluted with 100 ml of methyl tert-butyl ether and washed three times with in each case 50 ml of a 3:1 mixture of saturated aqueous sodium chloride solution and 1N hydrochloric acid. The organic phase was dried over sodium sulphate and concentrated under reduced pressure at RT. This gave 13 g of the crude product which was directly reacted further.

Example 8.1B tert-Butyl 2-[4-(5-chloro-2-cyanophenyl)-5-methoxy-2-oxopyridin-1(2H)-yl]-4-methoxybutanoate (racemate)

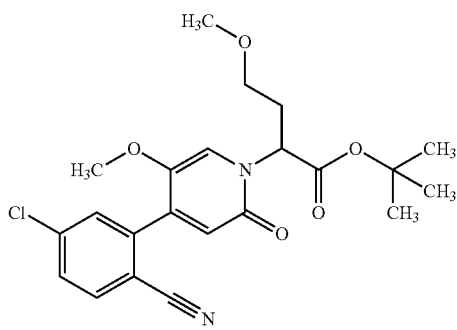 [SMILES: COCCC(C(=O)OC(C)(C)C)n1cc(OC)c(-c2cc(Cl)ccc2C#N)cc1=O]

8.09 g (21.6 mmol) of tert-butyl [4-(5-chloro-2-cyanophenyl)-5-methoxy-2-oxopyridin-1(2H)-yl]acetate were initially charged in 180 ml of THF, and the mixture was cooled to −78° C. 23.7 ml of bis(trimethylsilyl)lithiumamide (1M in THF) were added dropwise, and the mixture was left to stir for a further 15 min. 8.99 g (43.2 mmol) of 2-methoxyethyl trifluoromethanesulphonate were then added dropwise, and the mixture was left to stir at −78° C. for 15 min and at RT for a further 45 min Saturated aqueous ammonium chloride solution was then added, and the mixture was extracted repeatedly with ethyl acetate. The combined organic phases were dried over sodium sulphate and concentrated under reduced pressure. The residue was purified by flash chromatography (silica gel 50, cyclohexane/ethyl acetate gradient). Yield: 7.87 g (95% pure, 80% of theory).

LC/MS [Method 1]: $R_t$=1.02 min; MS (ESIpos): m/z=433 (M+H)$^+$,

1H-NMR (400 MHz, DMSO-d$_6$): δ [ppm]=8.01-7.96 (m, 1H), 7.76-7.69 (m, 2H), 7.37 (s, 1H), 6.48 (s, 1H), 5.11 (dd, 1H), 3.64 (s, 3H), 3.43-3.35 (m, 1H), 3.20 (s, 3H), 3.19-3.13 (m, 1H), 2.39-2.28 (m, 2H), 1.40 (s, 9H).

Example 8.1C

2-[4-(5-Chloro-2-cyanophenyl)-5-methoxy-2-oxopyridin-1(2H)-yl]-4-methoxybutanoic acid (racemate)

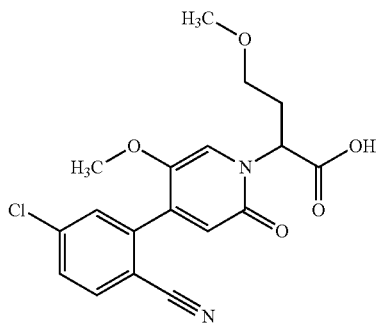 [SMILES: COCCC(C(=O)O)n1cc(OC)c(-c2cc(Cl)ccc2C#N)cc1=O]

7.87 g (95% pure, 17.3 mmol) of tert-butyl 2-[4-(5-chloro-2-cyanophenyl)-5-methoxy-2-oxopyridin-1(2H)-yl]-4-methoxybutanoate-(racemate) were initially charged in 175 ml of dichloromethane 42 ml (545 mmol) of trifluoroacetic acid were added, and the mixture was left to stir at RT for 3 h. The reaction mixture was concentrated under reduced pressure and repeatedly the residue was taken up in dichloromethane and concentrated again. Then, twice, toluene was added and the mixture was concentrated again. The residue was stirred with acetonitrile and filtered off with suction. Yield 5.81 g (95% pure, 84% of theory)

LC/MS [Method 1]: $R_t$=0.78 min; MS (ESIpos): m/z=377 (M+H)$^+$, $^1$H-NMR (500 MHz, DMSO-d$_6$): δ [ppm]=13.40-12.67 (m, 1H), 7.99 (d, 1H), 7.75 (d, 1H), 7.73 (dd, 1H), 7.43 (s, 1H), 6.48 (s, 1H), 5.14 (t, 1H), 3.64 (s, 3H), 3.41-3.36 (m, 1H), 3.19 (s, 3H), 3.13 (dt, 1H), 2.40-2.31 (m, 2H).

Example 9.1A

Ethyl trans-4-hydroxycyclohexanecarboxylate

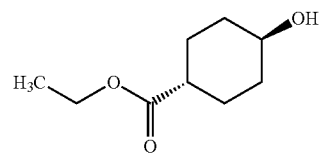

4.00 g (27.7 mmol) of trans-4-hydroxycyclohexanecarboxylic acid were initially charged in 50.2 ml of ethanol, and 2 ml of concentrated sulphuric acid were added at room temperature. The reaction solution was subsequently stirred at 80° C. for 10 h. The reaction solution was cooled to room temperature, and saturated aqueous sodium bicarbonate solution was added. The mixture was extracted with 200 ml of ethyl acetate, the organic phase was dried and filtered and the solvent was removed under reduced pressure. Yield: 4.3 g (90% of theory)

GC/MS [Method 9]: $R_t$=4.17 min; MS: m/z=172 (M)$^+$, $^1$H-NMR (400 MHz, DMSO-d$_6$): δ [ppm]=4.56 (d, 1H), 4.03 (q, 2H), 3.39-3.29 (m, 1H), 2.22-2.13 (m, 1H), 1.88-1.78 (m, 4H), 1.40-1.27 (m, 2H), 1.21-1.09 (m, 2H), 1.16 (t, 3H).

Example 9.1B

Ethyl trans-4-{[tert-butyl(dimethyl)silyl]oxy}cyclohexanecarboxylate

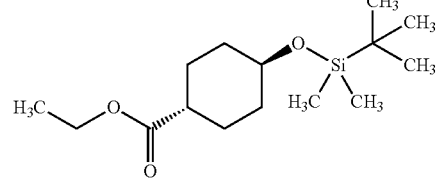

4.3 g (25 mmol) of ethyl trans-4-hydroxycyclohexanecarboxylate were initially charged in 20 ml of dimethylformamide. 4.5 g (30 mmol) of tert-butyldimethylsilyl chloride and 4.2 g (62 mmol) of imidazole were then added, and the mixture was stirred at 35° C. for another 12 h. 200 ml of ethyl acetate were added and the reaction solution was extracted three times with 100 ml of water. The organic phase was dried and filtered and the solvent was removed under reduced pressure. Yield: 7.8 g (quantitative)

GC/MS [Method 9]: $R_t$=5.04 min; MS: m/z=286 (M)+, $^1$H-NMR (400 MHz, DMSO-d$_6$): δ [ppm]=4.00 (q, 2H), 3.59-3.50 (m, 1H), 2.24-2.14 (m, 1H), 1.86-1.71 (m, 4H), 1.41-1.29 (m, 2H), 1.27-1.16 (m, 2H), 1.13 (t, 3H), 0.82 (s, 9H), 0.00 (s, 6H).

Example 9.1C (trans-4-{[tert-Butyl(dimethyl)silyl]oxy}cyclohexyl)methanol

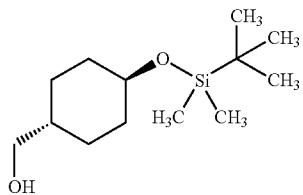 [SMILES: CC(C)(C)[Si](C)(C)O[C@H]1CC[C@H](CO)CC1]

12.5 ml (29.9 mmol) of lithium aluminium hydride (2.4M in THF) were initially charged in 90 ml of methyl tert-butyl ether, and a solution of 7.8 g (27.2 mmol) of ethyl trans-4-{[tert-butyl(dimethyl)silyl]oxy}cyclohexanecarboxylate in 90 ml of methyl tert-butyl ether was added at room temperature. The mixture was then stirred at 40° C. for 4 h. The reaction was terminated by addition of 7 ml of water and 7 ml of 15% strength aqueous potassium hydroxide solution. The organic phase was decanted, dried over magnesium sulphate and filtered, and the solvent was removed under reduced pressure. Yield: 6.3 g (95% of theory)

GC/MS [Method 9]: $R_t$=4.74 min; MS: m/z=244 (M)+, $^1$H-NMR (400 MHz, DMSO-d$_6$): δ [ppm]=4.35 (t, 1H), 3.52-3.44 (m, 1H), 3.15 (t, 2H), 1.80-1.72 (m, 2H), 1.71-1.62 (m, 2H), 1.29-1.09 (m, 3H), 0.92-0.80 (m, 2H), 0.82 (s, 9H), 0.00 (s, 6H).

Example 9.1D (trans-4-{[tert-Butyl(dimethyl)silyl]oxy}cyclohexyl)methyl trifluoromethanesulphonate

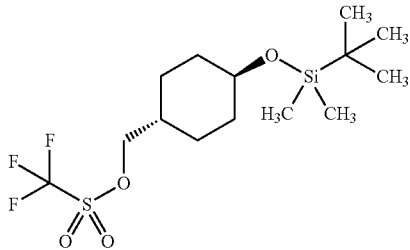 [SMILES: CC(C)(C)[Si](C)(C)O[C@H]1CC[C@H](COS(=O)(=O)C(F)(F)F)CC1]

6.30 g (25.8 mmol) of (trans-4-{[tert-butyl(dimethyl)silyl]oxy}cyclohexyl)methanol were initially charged in 90 ml of dichloromethane and, at 0° C., reacted with 4.50 ml (38.7 mmol) of lutidine and 6.54 ml (38.7 mmol) of trifluoromethanesulphonic anhydride, where the internal temperature should not exceed 5° C. The mixture was stirred for 1 h. The reaction solution was then diluted with 630 ml of methyl tert-butyl ether and successively washed three times with a mixture of aqueous hydrochloric acid (1N)/saturated aqueous sodium chloride solution (1:3) and saturated aqueous sodium bicarbonate solution. The organic phase was dried and filtered and the solvent was removed under reduced pressure. The crude product was used in the next step without further purification. Yield: 9.7 g (quantitative)

Example 9.1E tert-Butyl 3-(trans-4-{[tert-butyl(dimethyl)silyl]oxy}cyclohexyl)-2-[4-(5-chloro-2-cyanophenyl)-5-methoxy-2-oxopyridin-1(2H)-yl]propanoate (racemate)

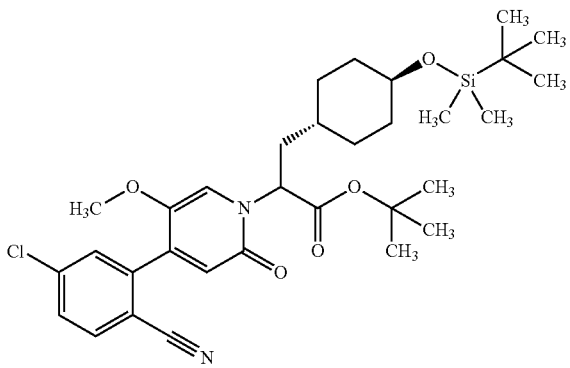 [SMILES: COc1cn(C(C[C@H]2CC[C@H](O[Si](C)(C)C(C)(C)C)CC2)C(=O)OC(C)(C)C)c(=O)cc1-c1cc(Cl)ccc1C#N]

4.90 g (12.3 mmol) of tert.-butyl [4-(5-chloro-2-cyanophenyl)-5-methoxy-2-oxopyridin-1(2H)-yl]acetate were initially charged in 98 ml of THF, and 13.6 ml (13.6 mmol) of bis(trimethylsilyl)lithiumamide (1M in THF) were added at −78° C. The mixture was stirred at −78° C. for 15 min, and 6.97 g (18.5 mmol) of (trans-4-{[tert-butyl(dimethyl)silyl]oxy}cyclohexyl)methyl trifluoromethanesulphonate were then added. The mixture was stirred at −78° C. for 15 min and at room temperature for 2 h. The reaction was terminated by addition of saturated aqueous ammonium chloride solution, and the phases were separated. The aqueous phase was extracted three times with 174 ml of methyl tert-butyl ether. The combined organic phases were dried and filtered, and the solvent was removed under reduced pressure. Purification by column chromatography of the crude product (100 g silica cartridge, flow rate: 50 ml/min, cyclohexane/ethyl acetate gradient) gave the title compound. Yield: 3.10 g (42% of theory)

LC/MS [Method 1]: $R_t$=1.59 min; MS (ESIpos): m/z=601 (M+H)+.

Example 9.1F 3-(trans-4-{[tert-Butyl(dimethyl)silyl]
oxy}cyclohexyl)-2-[4-(5-chloro-2-cyanophenyl)-5-
methoxy-2-oxopyridin-1(2H)-yl]propanoic acid
(racemate)

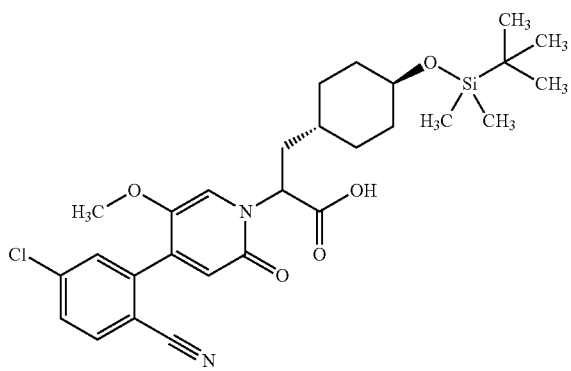 [SMILES: COc1cn(C(C[C@H]2CC[C@H](O[Si](C)(C)C(C)(C)C)CC2)C(=O)O)c(=O)cc1-c1cc(Cl)ccc1C#N]

3.10 g (5.16 mmol) of tert-butyl 3-(trans-4-{[tert-butyl (dimethyl)silyl]oxy}cyclohexyl)-2-[4-(5-chloro-2-cyanophenyl)-5-methoxy-2-oxopyridin-1(2H)-yl]propanoate (racemate) were initially charged in 32.4 ml of THF, 16.2 ml of ethanol and 16.2 ml of water, and 1.08 g (25.8 mmol) of lithium hydroxide monohydrate were added. The mixture was stirred at room temperature for 6 h and then acidified with aqueous hydrochloric acid (1N) (pH=4-5). The mixture was extracted three times with 129 ml of ethyl acetate. The combined organic phases were dried and filtered, and the solvent was removed under reduced pressure. The crude product was used in the next step without further purification. Yield: 2.8 g (75% pure, quantitative)

LC/MS [Method 1]: $R_t$=1.37 min; MS (ESIpos): m/z=545 (M+H)$^+$.

Example 9.1G 3-(trans-4-{[tert-Butyl(dimethyl)silyl]
oxy}cyclohexyl)-2-[4-(5-chloro-2-cyanophenyl)-5-
methoxy-2-oxopyridin-1(2H)-yl]-N-(imidazo[1,2-a]
pyridin-6-yl)propanamide (racemate)

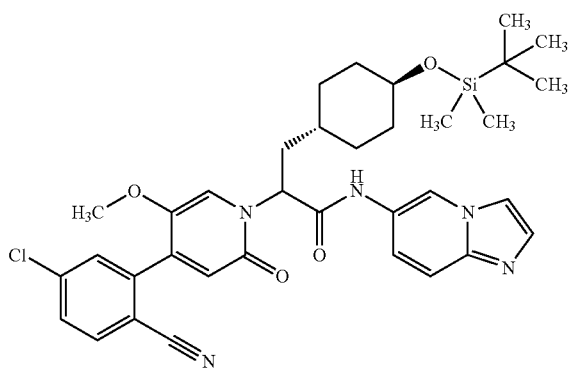 [SMILES: COc1cn(C(C[C@H]2CC[C@H](O[Si](C)(C)C(C)(C)C)CC2)C(=O)Nc2ccc3nccn3c2)c(=O)cc1-c1cc(Cl)ccc1C#N]

100 mg (183 µmol, 75% pure) of 3-(trans-4-{[tert-butyl (dimethyl)silyl]oxy}cyclohexyl)-2-[4-(5-chloro-2-cyano-phenyl)-5-methoxy-2-oxopyridin-1(2H)-yl]propanoic acid (racemate), 24.4 mg (183 µmol) of imidazo[1,2-a]pyridine-6-amine and 26.1 mg (183 mmol) of ethyl cyano(hydroxy-imino)ethanoate were initially charged in 1.84 ml of dim-ethylformamide, and the solution was degassed for 10 min 29.0 µl (183 µmol) of N,N'-diisopropylcarbodiimide were then added dropwise, and the resulting reaction solution was shaken at 40° C. overnight. The solvent was removed under reduced pressure and the residue was taken up in a little dichloromethane, giving, after purification by column chromatography (24 g silica cartridge, flow rate: 35 ml/min, dichloromethane/methanol gradient), the title compound. Yield: 63.1 mg (purity 57%, 52% of theory)

LC/MS [Method 1]: $R_t$=1.11 min; MS (ESIpos): m/z=660 (M+H)$^+$.

Example 10.1A

4-Chloro-2-(5-chloro-2-methoxypyridin-4-yl)benzo-nitrile

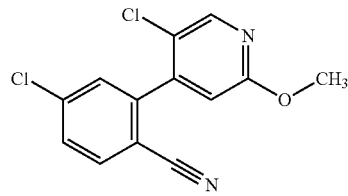 [SMILES: COc1cc(-c2cc(Cl)ccc2C#N)c(Cl)cn1]

5.36 g (purity 91%, 26.03 mmol) of 5-chloro-2-methoxy-pyridin-4-ylboronic acid and 5.12 g (23.66 mmol) of 2-bromo-4-chlorobenzonitrile in the presence of [1,1-bis (diphenylphosphino)ferrocene]palladium(II) chloride/di-chloromethane monoadduct were reacted according to General Method 2A. After work-up, the crude product was then purified by flash chromatography (silica gel 60, cyclo-hexane/dichloromethane mixtures). Yield: 4.11 g (91% pure, 52% of theory).

LC/MS [Method 1]: $R_t$=1.17 min; MS (ESIpos): m/z=279 (M+H)$^+$.

Example 10.1B

4-Chloro-2-(5-chloro-2-oxo-1,2-dihydropyridin-4-yl)benzonitrile

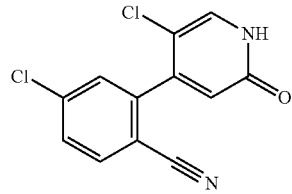 [SMILES: N#Cc1ccc(Cl)cc1-c1cc(=O)[nH]cc1Cl]

6.34 g (purity 93%, 21.12 mmol) of 4-chloro-2-(5-chloro-2-methoxypyridin-4-yl)benzonitrile and pyridinium hydro-chloride were reacted according to General Method 3A. Yield: 4.23 g (76% of theory)

LC/MS [Method 1]: $R_t$=0.82 min; MS (ESIpos): m/z=265 (M+H)$^+$.

Example 10.1C tert-Butyl [5-chloro-4-(5-chloro-2-cyanophenyl)-2-oxopyridin-1(2H)-yl]acetate

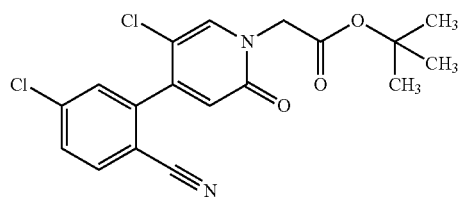 [SMILES: CC(C)(C)OC(=O)Cn1cc(Cl)c(-c2cc(Cl)ccc2C#N)cc1=O]

3.1 g (11.46 mmol) of 4-chloro-2-(5-chloro-2-oxo-1,2-dihydropyridin-4-yl)benzonitrile and 1.2 eq. of tert-butyl bromoacetate were reacted according to General Method 4B at 100° C. Yield: 3.65 g (84% of theory)

LC/MS [Method 8]: $R_t$=1.34 min, MS (ESIneg): m/z=377 (M−H)⁻,

¹H-NMR (400 MHz, DMSO-d₆): δ [ppm]=8.20 (s, 1H), 8.09-8.20 (m, 1H), 7.85-7.72 (m, 2H), 6.67 (s, 1H), 4.65 (s, 2H), 1.44 (s, 9H).

Example 10.1D tert-Butyl 2-[5-chloro-4-(5-chloro-2-cyanophenyl)-2-oxopyridin-1(2H)-yl]-4-methoxybutanoate (racemate)

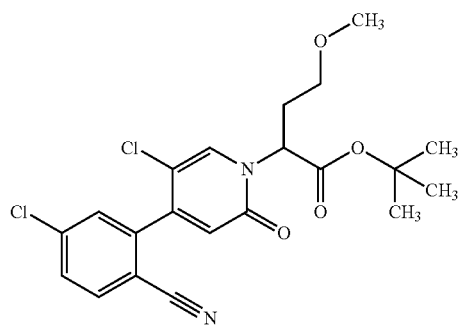 [SMILES: COCCC(C(=O)OC(C)(C)C)n1cc(Cl)c(-c2cc(Cl)ccc2C#N)cc1=O]

2.0 g (5.27 mmol) of tert-butyl [5-chloro-4-(5-chloro-2-cyanophenyl)-2-oxopyridin-1(2H)-yl]acetate in the presence of 7.12 ml (7.12 mmol, 1.35 eq.) of bis(trimethylsilyl) lithium amide (1M in THF) and 1.33 g (95% pure, 6.06 mmol, 1.15 eq.) of 2-methoxyethyl trifluoromethanesulphonate were reacted according to General Method 8A. Yield: 2.10 g (94% pure, 86% of theory).

LC/MS [Method 1]: $R_t$=1.14 min; MS (ESIpos): m/z=437 (M+H)⁺,

¹H-NMR (400 MHz, DMSO-d₆): δ [ppm]=8.16-8.10 (m, 1H), 8.09-8.02 (m, 1H), 7.73-7.84 (m, 2H), 6.64 (s, 1H), 5.25-5.07 (m, 1H), 3.44-3.36 (m, 1H), 3.22-3.12 (m, 4H), 2.41-2.27 (m, 2H).

Example 10.1E

2-[5-Chloro-4-(5-chloro-2-cyanophenyl)-2-oxopyridin-1(2H)-yl]-4-methoxybutanoate (racemate)

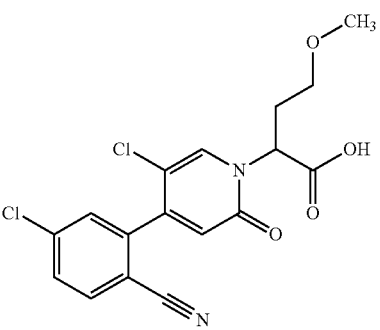 [SMILES: COCCC(C(=O)O)n1cc(Cl)c(-c2cc(Cl)ccc2C#N)cc1=O]

2.1 g (94% pure, 4.51 mmol) of tert-butyl 2-[5-chloro-4-(5-chloro-2-cyanophenyl)-2-oxopyridin-1(2H)-yl]-4-methoxybutanoate (racemate) were reacted according to General Method 6A. Yield: 1.89 g (quant.)

LC/MS [Method 1]: $R_t$=0.85 min; MS (ESIpos): m/z=381 (M+H)⁺,

¹H-NMR (400 MHz, DMSO-d₆): δ [ppm]=13.19 (br. s, 1H), 8.15 (s, 1H), 8.05 (d, 1H), 7.82 (d, 1H), 7.81-7.76 (m, 1H), 6.63 (s, 1H), 5.31-5.13 (m, 1H), 3.46-3.35 (m, 1H), 3.22-3.08 (m, 4H), 2.43-2.27 (m, 2H).

Example 11.1A

Pyridin-2-ylmethyl methanesulphonate

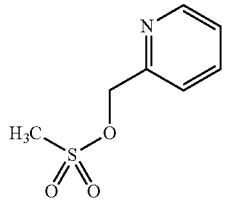

Under argon and at 0° C., a solution of 2.84 ml (36.65 mmol, 1 eq.) of methanesulphonyl chloride in 24 ml of tetrahydrofuran was added to a solution of 4.00 g (36.65 mmol, 2.2 eq.) of pyridin-2-ylmethanol and 11.24 ml (80.64 mmol, 2.2 eq.) of triethylamine in 122 ml of tetrahydrofuran, and the mixture was stirred for 3 h. Tetrahydrofuran was removed under reduced pressure. The crude product was then dissolved in dichloromethane, and the resulting mixture was washed with saturated aqueous sodium chloride solution. The organic phase was dried (sodium sulphate), filtered and concentrated under reduced pressure. The crude product was then purified by normal phase chromatography (mobile phase: cyclohexane/ethyl acetate (20-50%) mixtures). Yield: 4.72 g (68% of theory)

LC/MS [Method 3]: $R_t$=0.98 min; MS (ESIpos): m/z=188 (M+H)⁺,

¹H-NMR (400 MHz, DMSO-d₆): δ [ppm]=8.67-8.48 (m, 1H), 7.89 (td, 1H), 7.54 (d, 1H), 7.42 (ddd, 1H), 5.30 (s, 2H), 3.28 (s, 3H).

Example 11.1B tert-Butyl 2-[4-(5-chloro-2-cyanophenyl)-5-methoxy-2-oxopyridin-1(2H)-yl]-3-(pyridin-2-yl)propanoate (racemate)

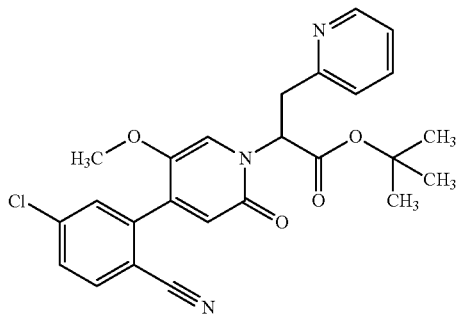 [SMILES: COc1cn(C(Cc2ccccn2)C(=O)OC(C)(C)C)c(=O)cc1-c1cc(Cl)ccc1C#N]

Under argon and at −78° C., 4.60 ml (1.0M in THF, 1.15 eq.) of bis(trimethylsilyl)lithium amide were added dropwise to a solution of 1.50 g (4.00 mmol) of tert-butyl [4-(5-chloro-2-cyanophenyl)-5-methoxy-2-oxopyridin-1(2H)-yl]acetate in 30 ml of tetrahydrofuran, and the mixture was stirred for 15 min. 1.06 g (5.6 mmol, 1.4 eq.) of neat pyridin-2-ylmethyl methanesulphonate were then added. The resulting reaction mixture was stirred at −78° C. for another 30 min and at RT for another 1.5 h.

Saturated aqueous ammonium chloride solution was added to the reaction mixture. After phase separation, the aqueous phase was extracted with ethyl acetate. The combined organic phases were washed with saturated aqueous sodium chloride solution. The organic phase was dried (sodium sulphate), filtered and concentrated under reduced pressure. The crude product was then purified by normal phase chromatography (mobile phase: dichloromethane/methanol (2-5%) mixtures). Yield 1.99 g (93% pure, 99% of theory)

LC/MS [Method 1]: $R_t$=0.97 min; MS (ESIpos): m/z=466 (M+H)$^+$.

Example 11.1C

2-[4-(5-Chloro-2-cyanophenyl)-5-methoxy-2-oxopyridin-1(2H)-yl]-3-(pyridin-2-yl)propanoic acid (racemate)

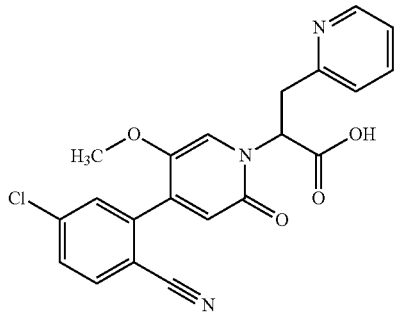 [SMILES: COc1cn(C(Cc2ccccn2)C(=O)O)c(=O)cc1-c1cc(Cl)ccc1C#N]

1.99 g (purity 93%, 3.98 mmol) of tert-butyl 2-[4-(5-chloro-2-cyanophenyl)-5-methoxy-2-oxopyridin-1(2H)-yl]-3-(pyridin-2-yl)propanoate (racemate) in 40 ml of dichloromethane and 20 ml (259.6 mmol) of TFA were reacted according to General Method 6A. Yield: 220 mg (purity 93%, 13% of theory)

LC/MS [Method 1]: $R_t$=0.64 min; MS (ESIpos): m/z=410 (M+H)$^+$, $^1$H-NMR (400 MHz, DMSO-d$_6$): δ [ppm]=13.08 (br. s, 1H), 8.48 (d, 1H), 7.95 (d, 1H), 7.73-7.60 (m, 3H), 7.27 (s, 1H), 7.24-7.11 (m, 2H), 6.40 (s, 1H), 5.55 (t, 1H), 3.66-3.57 (m, 2H), 3.49 (s, 3H).

Example 12.1A 5-(Bromomethyl)-1,3-oxazole

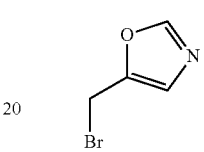

Under argon and at 0° C., 1.02 ml (13.12 mmol, 1.3 eq.) of methanesulphonyl chloride were added dropwise to a solution of 1.83 ml (13.12 mmol, 1.3 eq.) of triethylamine and 1.0 g (10.09 mmol, 1 eq.) of 1,3-oxazol-5-ylmethanol in 14 ml of N,N-dimethylformamide, and the mixture was stirred at 0° C. for 1 h. 2.45 g (28.26 mmol, 2.8 eq.) of lithium bromide were then added, and this reaction mixture was stirred at 0° C. for 1 h. After addition of water, the mixture was extracted with ethyl acetate. The combined organic phases were washed with saturated aqueous sodium chloride solution, dried over sodium sulphate and concentrated under reduced pressure. The crude product was then purified by normal phase chromatography (mobile phase: dichloromethane). Yield 1.23 g (80% pure, 60% of theory)

$^1$H-NMR (400 MHz, DMSO-d$_6$): δ [ppm]=8.42 (s, 1H), 7.26 (s, 1H), 4.93 (s, 2H).

Example 12.1B tert-Butyl 2-[4-(5-chloro-2-cyanophenyl)-5-methoxy-2-oxopyridin-1(2H)-yl]-oxazol-5-yl)propanoate (racemate)

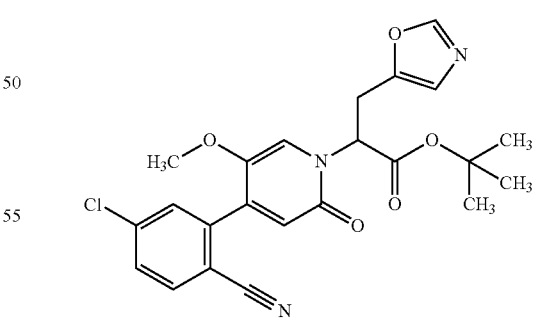

1.5 g (4.00 mmol) of tert-butyl [4-(5-chloro-2-cyanophenyl)-5-methoxy-2-oxopyridin-1(2H)-yl]acetate and 1.78 g (51% pure, 5.60 mmol, 1.4 eq.) of 5-(bromomethyl)-1,3-oxazole were reacted according to General Method 8B. Yield: 1.89 g (60% pure, 62% of theory).

LC/MS [Method 1]: $R_t$=0.98 min; MS (ESIpos): m/z=456 (M+H)$^+$.

Example 12.1C

2-[4-(5-Chloro-2-cyanophenyl)-5-methoxy-2-oxopyridin-1(2H)-yl]-3-(1,3-oxazol-5-yl)propanoic acid (racemate)

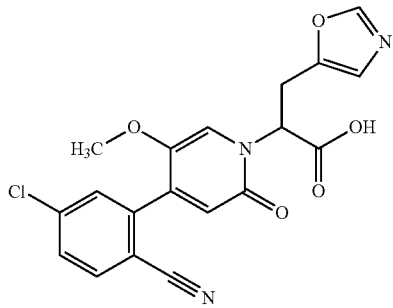 [SMILES: COc1cn(C(Cc2cnco2)C(=O)O)c(=O)cc1-c1cc(Cl)ccc1C#N]

1.89 g (purity 60%, 2.48 mmol) of tert-butyl 2-[4-(5-chloro-2-cyanophenyl)-5-methoxy-2-oxopyridin-1(2H)-yl]-3-(1,3-oxazol-5-yl)propanoate (racemate) in 28 ml of dichloromethane and 14 ml (435 mmol) of TFA were reacted according to General Method 6A. Yield: 597 mg (purity 80%, 48% of theory)

LC/MS [Method 1]: $R_t$=0.70 min; MS (ESIpos): m/z=400 (M+H)$^+$, $^1$H-NMR (400 MHz, DMSO-d$_6$): δ [ppm]=13.24 (br. s, 1H), 8.17 (s, 1H), 8.02-7.93 (m, 1H), 7.77-7.66 (m, 2H), 7.35 (s, 1H), 6.85 (s, 1H), 6.47 (s, 1H), 5.32 (dd, 1H), 3.63-3.72 (m, 1H), 3.58-3.47 (m, 4H).

Example 13.1A tert.-Butyl 2-[5-chloro-4-(5-chloro-2-cyanophenyl)-2-oxopyridin-1(2H)-yl]-3-(1,3-oxazol-5-yl)propanoate-(racemate)

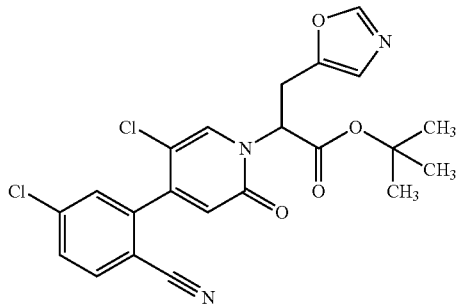 [SMILES: CC(C)(C)OC(=O)C(Cc1cnco1)n1cc(Cl)c(-c2cc(Cl)ccc2C#N)cc1=O]

610 mg (1.61 mmol) of tert-butyl [5-chloro-4-(5-chloro-2-cyanophenyl)-2-oxopyridin-1(2H)-yl]acetate and 1.57 g (23% pure, 2.25 mmol, 1.4 eq.) of 5-(bromomethyl)-1,3-oxazole were reacted according to General Method 8B. Yield: 468 mg (purity 83%, 52% of theory)

LC/MS [Method 1]: $R_t$=1.05 min; MS (ESIpos): m/z=460 (M+H)$^+$.

Example 13.1B

2-[5-Chloro-4-(5-chloro-2-cyanophenyl)-2-oxopyridin-1(2H)-yl]-3-(1,3-oxazol-5-yl)propanoic acid (racemate)

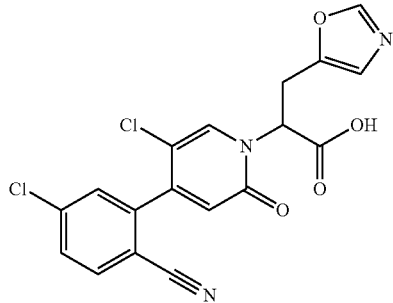 [SMILES: N#Cc1ccc(Cl)cc1-c1cc(=O)n(C(Cc2cnco2)C(=O)O)cc1Cl]

468 mg (purity 83%, 0.84 mmol) of tert-butyl 2-[5-chloro-4-(5-chloro-2-cyanophenyl)-2-oxopyridin-1(2H)-yl]-3-(1,3-oxazol-5-yl)propanoate (racemate) in 9 ml of dichloromethane and 4.5 ml (58.4 mmol) of TFA were reacted according to General Method 6A. Yield: 290 mg (purity 85%, 72% of theory)

LC/MS [Method 1]: $R_t$=0.76 min; MS (ESIpos): m/z=404 (M+H)$^+$, $^1$H-NMR (400 MHz, DMSO-d$_6$): δ [ppm]=13.48 (br. s, 1H), 8.17 (s, 1H), 8.10 (s, 1H), 8.08-8.01 (m, 1H), 7.81-7.75 (m, 2H), 6.87 (s, 1H), 6.64 (s, 1H), 5.39 (br. s, 1H), 3.65 (dd, 1H), 3.56 (dd, 1H).

Example 14.1A

6-Methoxypyridin-3-ol

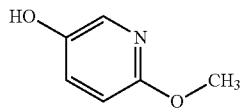

At RT, 50 g (327 mmol) of 6-methoxypyridin-3-ylboronic acid were added to a solution of 46.0 g (392 mmol) of N-methylmorpholine N-oxide in 500 ml of dichloromethane, and the mixture was stirred at 50° C. for 14 h. Additional N-methylmorpholine N-oxide was added until the reaction had gone to completion. The reaction mixture was concentrated under reduced pressure and the crude product was purified by flash chromatography (silica gel 60, cyclohexane/ethyl acetate mixtures). Yield: 32.9 g (80% of theory)

LC/MS [Method 1]: $R_t$=0.37 min; MS (ESIpos): m/z=126 (M+H)$^+$, $^1$H-NMR (400 MHz, DMSO-d$_6$): δ [ppm]=9.27 (s, 1H), 7.67 (d, 1H), 7.16 (dd, 1H), 6.66 (d, 1H), 3.74 (s, 3H).

Example 14.1B

2-Methoxy-5-(tetrahydro-2H-pyran-2-yloxy)pyridine

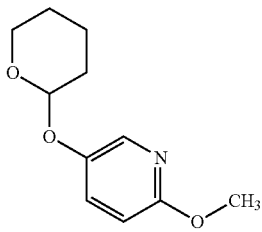

10.1 g (119.9 mmol, 1.5 eq.) of 3,4-dihydro-2H-pyran and 1.4 g (8.0 mmol, 0.1 eq.) of 4-toluenesulphonic acid were added to a solution of 10.0 g (79.9 mmol) of 6-methoxy-pyridin-3-ol in 150 ml of dichloromethane, and the mixture was stirred at RT for 5 days. After addition of water/dichloromethane and phase separation, the aqueous phase was extracted with dichloromethane. The combined organic phases were dried (sodium sulphate), filtered and concentrated under reduced pressure. Yield: 17.3 g (100% of theory)

LC/MS [Method 1]: $R_t$=0.95 min; MS (ESIpos): m/z=210 (M+H)$^+$.

Example 14.1C

4-Iodo-2-methoxy-5-(tetrahydro-2H-pyran-2-yloxy)pyridine

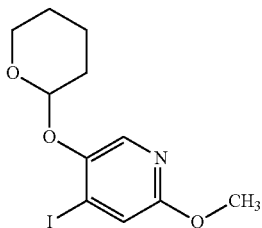 [SMILES: COc1cc(I)c(OC2CCCCO2)cn1]

At −78° C., 13.6 ml (90.1 mmol, 1.2 eq.) of 1,2-bis(dimethylamino)ethane and 54.0 ml (86.4 mmol, 1.15 eq.) of n-butyllithium were added to a solution of 16.2 g (75.1 mmol) of 2-methoxy-5-(tetrahydro-2H-pyran-2-yloxy)pyridine in 250 ml of THF, and the mixture was stirred at −78° C. for 1 h. 24.8 g (97.6 mmol, 1.3 eq.) of iodine were then added, and the reaction mixture was stirred at −78° C. for 1 h and then allowed to warm to RT overnight. The reaction mixture was quenched with water and extracted three times with ethyl acetate. The combined organic phases were washed with saturated sodium thiosulphate solution, dried (sodium sulphate), filtered and concentrated under reduced pressure. Yield: 25.1 g (82% pure, 82% of theory).

LC/MS [Method 1]: $R_t$=1.18 min; MS (ESIpos): m/z=336 (M+H)$^+$.

Example 14.1D

4-Iodo-6-methoxypyridin-3-ol

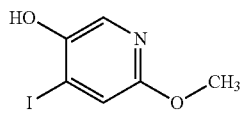

50 ml (3 molar, 150 mmol) of hydrochloric acid were added to a solution of 25.1 g (purity 82%, 61.3 mmol) of 4-iodo-2-methoxy-5-(tetrahydro-2H-pyran-2-yloxy)pyridine in 50 ml of dioxane and 50 ml of water, and the mixture was stirred at RT for 2 h. The reaction mixture was then filtered and the precipitate was rinsed with water and dried under high vacuum. Yield: 13.5 g (93% pure, 81% of theory).

LC/MS [Method 1]: $R_t$=0.76 min; MS (ESIpos): m/z=252 (M+H)$^+$, $^1$H-NMR (400 MHz, DMSO-d$_6$): δ [ppm]=7.70 (s, 1H), 7.22 (s, 1H), 3.74 (s, 3H).

Example 14.1E 5-(Difluoromethoxy)-4-iodo-2-methoxypyridine

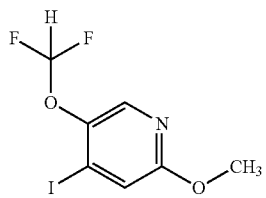

4.8 ml of aqueous potassium hydroxide solution (6M) were added to a solution of 600 mg (93% pure, 2.22 mmol) of 4-iodo-6-methoxypyridin-3-ol in 4.8 ml of acetonitrile, the mixture was cooled in an ice bath and 863 μl (75% pure, 3.56 mmol, 1.6 eq.) of difluoromethyl trifluormethanesulphonate [*Angew. Chem. Int. Ed.* 2013, 52, 1-5; *Journal of Fluorine Chemistry* 2009, 130, 667-670] were added with vigorous stirring. The reaction mixture was stirred for 2 min and diluted with 33 ml of water. The aqueous phase was extracted twice with in each case 40 ml of diethyl ether. The combined organic phases were dried (sodium sulphate), filtered, concentrated under reduced pressure and dried. The crude product was purified by flash chromatography (silica gel, petroleum ether/ethyl acetate (12-20%) mixtures). Yield: 407 mg (purity 90%, 55% of theory)

$^1$H-NMR (400 MHz, DMSO-d$_6$): δ [ppm]=8.1 (s, 1H), 7.45 (s, 1H), 7.16 (t, 1H), 3.84 (s, 3H).

Example 14.1F

4-Chloro-2-[5-(difluoromethoxy)-2-methoxypyridin-4-yl]benzonitrile

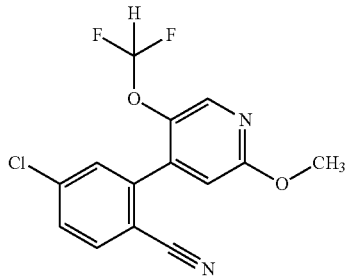 [SMILES: COc1cc(-c2cc(Cl)ccc2C#N)c(OC(F)F)cn1]

460 mg (purity 90%, 1.38 mmol) of 5-(difluoromethoxy)-4-iodo-2-methoxypyridine and 299 mg (1.65 mmol, 1.2 eq.) of 5-chloro-2-cyanophenylboronic acid in the presence of [1,1-bis(diphenylphosphino)ferrocene]palladium(II) chloride/dichloromethane monoadduct were reacted according to General Method 2A. The crude product was purified by flash chromatography (silica gel, petroleum ether/ethyl acetate (10-15%) mixtures). Yield: 230 mg (purity 80%, 43% of theory)

LC/MS [Method 1]: $R_t$=1.12 min; MS (ESIpos): m/z=311 (M+H)$^+$, $^1$H-NMR (400 MHz, DMSO-d$_6$): δ [ppm]=8.26 (s, 1H), 8.06 (d, 1H), 7.82-7.74 (m, 2H), 7.09 (s, 1H), 7.06 (t, 1H), 3.91 (s, 3H).

Example 14.1G

4-Chloro-2-[5-(difluoromethoxy)-2-oxo-1,2-dihydropyridin-4-yl]benzonitrile

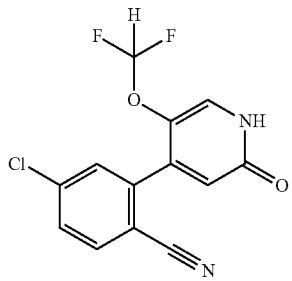 [SMILES: N#Cc1ccc(Cl)cc1-c1cc(=O)[nH]cc1OC(F)F]

230 mg (purity 80%, 0.59 mmol) of 4-chloro-2-[5-(difluoromethoxy)-2-methoxypyridin-4-yl]benzonitrile and pyridinium hydrobromide were reacted according to General Method 3A. The crude product was purified by flash chromatography (silica gel, dichloromethane/methanol (3-25%) mixtures). Yield: 167 mg (95% of theory)

LC/MS [Method 1]: $R_t$=0.79 min; MS (ESIpos): m/z=297 (M+H)$^+$, $^1$H-NMR (400 MHz, DMSO-d$_6$): δ [ppm]=11.88 (br. s, 1H), 8.03 (d, 1H), 7.80-7.65 (m, 3H), 6.87 (t, 1H), 6.56 (s, 1H).

Example 14.1H tert-Butyl [4-(5-chloro-2-cyanophenyl)-5-(difluoromethoxy)-2-oxopyridin-1(2H)-yl]acetate

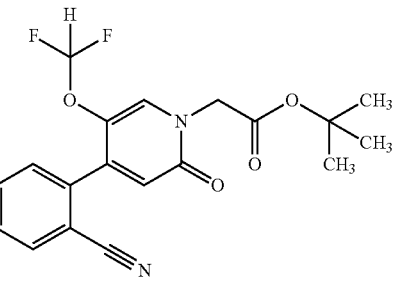

1.19 g (purity 92%, 3.69 mmol) of 4-chloro-2-[5-(difluoromethoxy)-2-oxo-1,2-dihydropyridin-4-yl]benzonitrile and 1.2 eq. of tert-butyl bromoacetate were reacted according to General Method 4B at 100° C. Yield: 1.30 g (95% pure, 81% of theory).

LC/MS [Method 1]: $R_t$=0.97 min; MS (ESIpos): m/z=411 (M+H)$^+$, $^1$H-NMR (400 MHz, DMSO-d$_6$): δ [ppm]=8.09-7.97 (m, 2H), 7.81-7.70 (m, 2H), 6.81 (t, 1H), 6.63 (s, 1H), 4.66 (s, 2H), 1.44 (s, 9H).

Example 14.1I tert-Butyl 2-[4-(5-chloro-2-cyanophenyl)-5-(difluoromethoxy)-2-oxopyridin-1(2H)-yl]-3-(1,3-oxazol-5-yl)propanoate (racemate)

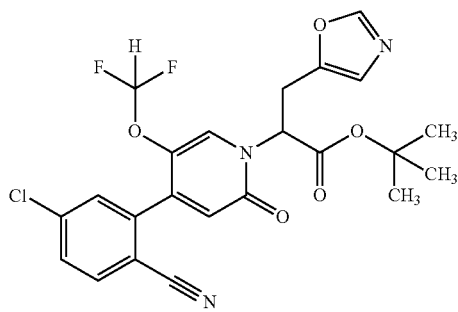 [SMILES: CC(C)(C)OC(=O)C(Cc1cnco1)n1cc(OC(F)F)c(-c2cc(Cl)ccc2C#N)cc1=O]

600 mg (1.39 mmol) of tert-butyl [4-(5-chloro-2-cyanophenyl)-5-(difluoromethoxy)-2-oxopyridin-1(2H)-yl]acetate and 421 mg (80% pure, 2.08 mmol, 1.5 eq.) of 5-(bromomethyl)-1,3-oxazole were reacted according to General Method 8B. Yield: 320 mg (47% of theory)

LC/MS [Method 1]: $R_t$=0.97 min; MS (ESIpos): m/z=492 (M+H)$^+$, $^1$H-NMR (400 MHz, DMSO-d$_6$): δ [ppm]=8.18 (s, 1H), 8.03 (d, 1H), 7.86 (s, 1H), 7.82-7.71 (m, 2H), 6.90 (s, 1H), 6.72 (t, 1H), 6.62 (s, 1H), 5.35 (dd, 1H), 3.68-3.48 (m, 2H), 1.40 (s, 9H).

Example 14.1J

2-[4-(5-Chloro-2-cyanophenyl)-5-(difluoromethoxy)-2-oxopyridin-1(2H)-yl]-oxazol-5-yl) propanoic acid (racemate)

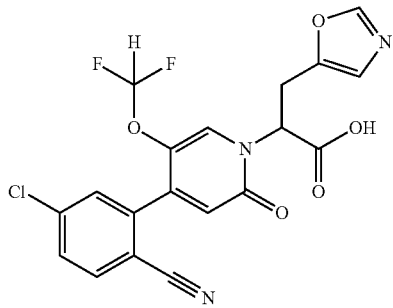 [SMILES: N#Cc1ccc(Cl)cc1-c1cc(=O)n(C(Cc2cnco2)C(=O)O)cc1OC(F)F]

320 mg (0.65 mmol) of tert-butyl 2-[4-(5-chloro-2-cyanophenyl)-5-(difluoromethoxy)-2-oxopyridin-1(2H)-yl]-3-(1,3-oxazol-5-yl)propanoate (racemate) in 10 ml of dichloromethane and 5 ml (64.9 mmol) of TFA were reacted according to General Method 6A. Yield: 290 mg (quant.)

LC/MS [Method 1]: $R_t$=0.74 min; MS (ESIpos): m/z=436 (M+H)$^+$, $^1$H-NMR (400 MHz, DMSO-d$_6$): δ [ppm]=13.42 (br. s, 1H), 8.15 (s, 1H), 8.03 (d, 1H), 7.87 (s, 1H), 7.81-7.69 (m, 2H), 6.86 (s, 1H), 6.72 (t, 1H), 6.60 (s, 1H), 5.37 (dd, 1H), 3.64 (dd, 2H), 3.53 (dd, 1H).

Example 15.1A 4-(Bromomethyl)-1,3-oxazole

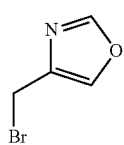

Under argon and at 0° C., 1.06 ml (13.72 mmol, 1.3 eq.) of methanesulphonyl chloride were added dropwise to a solution of 1.91 ml (13.72 mmol, 1.3 eq.) of triethylamine and 1.05 g (10.56 mmol) of 1,3-oxazol-4-ylmethanol in 15 ml of N,N-dimethylformamide, and the mixture was stirred at 0° C. for 1 h. 2.57 g (29.56 mmol, 2.8 eq.) of lithium bromide were then added, and the reaction mixture was stirred at 0° C. for 1 h. After addition of water, the mixture was extracted with ethyl acetate. The combined organic phases were washed with saturated aqueous sodium chloride solution, dried over sodium sulphate and concentrated under reduced pressure. The crude product was converted without further work-up. Yield 1.97 g (50% pure, 58% of theory)

$^1$H-NMR (400 MHz, DMSO-d$_6$): δ [ppm]=8.40 (s, 1H), 8.18 (s, 1H), 4.59 (s, 2H).

Example 15.1B tert-Butyl 2-[4-(5-chloro-2-cyanophenyl)-5-methoxy-2-oxopyridin-1(2H)-yl]-oxazol-4-yl)propanoate (racemate)

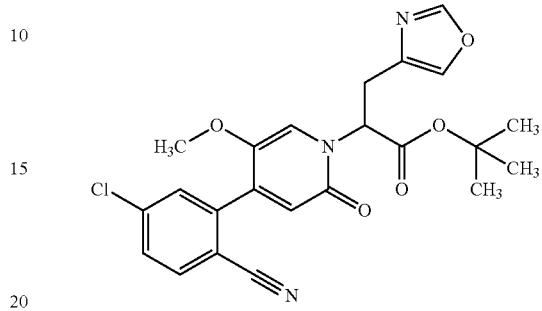

813 mg (2.17 mmol) of tert-butyl [4-(5-chloro-2-cyanophenyl)-5-methoxy-2-oxopyridin-1(2H)-yl]acetate and 983.8 mg (50% pure, 3.04 mmol, 1.4 eq.) of 4-(bromomethyl)-1,3-oxazole were reacted according to General Method 8B. Yield: 655 mg (65% of theory)

LC/MS [Method 1]: $R_t$=0.98 min; MS (ESIpos): m/z=456 (M+H)$^+$, $^1$H-NMR (400 MHz, DMSO-d$_6$): δ [ppm]=8.28 (s, 1H), 7.97 (d, 1H), 7.78 (s, 1H), 7.75-7.61 (m, 2H), 7.31 (s, 1H), 6.45 (s, 1H), 5.34 (dd, 1H), 3.56 (s, 3H), 3.50-3.39 (m, 1H), 3.36-3.26 (m, 1H), 1.41 (s, 9H).

Example 15.1C

2-[4-(5-Chloro-2-cyanophenyl)-5-methoxy-2-oxopyridin-1(2H)-yl]-3-(1,3-oxazol-4-yl)propanoic acid (racemate)

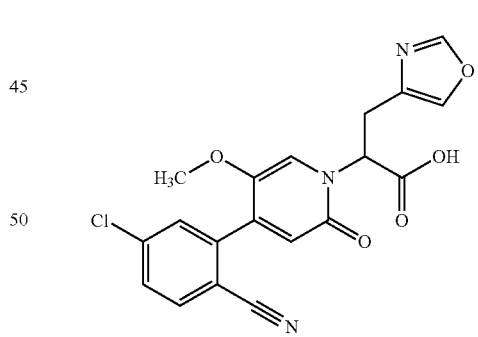

655 mg (1.41 mmol) of tert-butyl 2-[4-(5-chloro-2-cyanophenyl)-5-methoxy-2-oxopyridin-1(2H)-yl]-3-(1,3-oxazol-4-yl)propanoate (racemate) in 14 ml of dichloromethane and 7 ml (90.86 mmol) of TFA were reacted according to General Method 6A. Yield: 403 mg (70% of theory)

LC/MS [Method 1]: $R_t$=0.73 min; MS (ESIpos): m/z=400 (M+H)$^+$, $^1$H-NMR (400 MHz, DMSO-d$_6$): δ [ppm]=13.14 (br. s, 1H), 8.26 (s, 1H), 7.97 (d, 1H), 7.78-7.65 (m, 3H), 7.33 (s, 1H), 6.43 (s, 1H), 5.36 (dd, 1H), 3.55 (s, 3H), 3.53-3.43 (m, 1H), 3.38-3.25 (m, 1H).

Example 16.1A tert.-Butyl 2-[5-chloro-4-(5-chloro-2-cyanophenyl)-2-oxopyridin-1(2H)-yl]-3-(1,3-oxazol-4-yl)propanoate-(racemate)

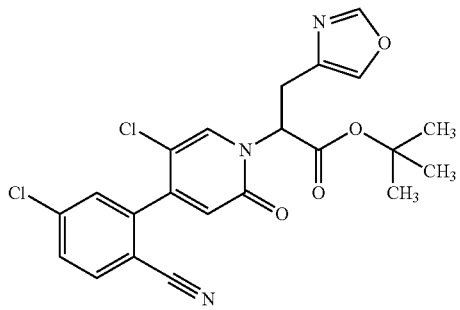 [SMILES: CC(C)(C)OC(=O)C(Cc1cocn1)n1cc(Cl)c(-c2cc(Cl)ccc2C#N)cc1=O]

600 mg (1.58 mmol) of tert-butyl [5-chloro-4-(5-chloro-2-cyanophenyl)-2-oxopyridin-1(2H)-yl]acetate and 717.6 mg (50% pure, 2.22 mmol, 1.4 eq.) of 4-(bromomethyl)-1,3-oxazole were reacted according to General Method 8B. Yield: 530 mg (73% of theory)

LC/MS [Method 1]: $R_t$=1.07 min; MS (ESIpos): m/z=460 (M+H)$^+$, $^1$H-NMR (400 MHz, DMSO-d$_6$): δ [ppm]=8.29 (s, 1H), 8.11-7.97 (m, 2H), 7.87-7.69 (m, 3H), 6.62 (s, 1H), 5.45-5.25 (m, 1H), 3.55-3.38 (m, 1H), 3.38-3.25 (m, 1H), 1.41 (s, 9H).

Example 16.1B

2-[5-Chloro-4-(5-chloro-2-cyanophenyl)-2-oxopyridin-1(2H)-yl]-3-(1,3-oxazol-4-yl)propanoic acid (racemate)

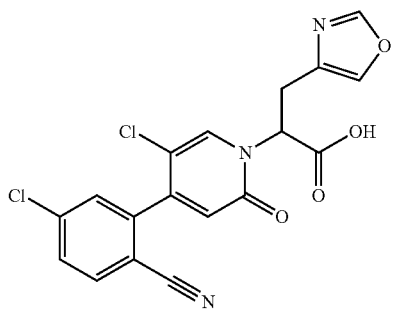

530 mg (1.15 mmol) of tert-butyl 2-[5-chloro-4-(5-chloro-2-cyanophenyl)-2-oxopyridin-1(2H)-yl]-3-(1,3-oxazol-4-yl)propanoate (racemate) in 12 ml of dichloromethane and 6 ml (77.9 mmol) of TFA were reacted according to General Method 6A. Yield: 359 mg (77% of theory)

LC/MS [Method 1]: $R_t$=0.78 min; MS (ESIpos): m/z=404 (M+H)$^+$, $^1$H-NMR (400 MHz, DMSO-d$_6$): δ [ppm]=13.36 (br. s, 1H), 8.26 (s, 1H), 8.11-7.98 (m, 2H), 7.87-7.67 (m, 3H), 6.59 (s, 1H), 5.42 (dd, 1H), 3.59-3.41 (m, 1H), 3.38-3.28 (m, 1H).

Example 17.1A

Dibenzyl 1,3-acetonedicarboxylate

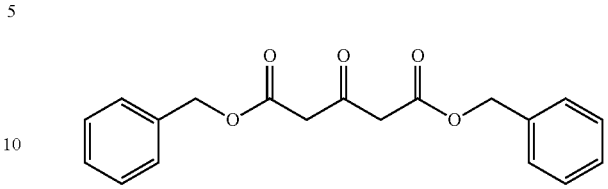

14.1 g (81.0 mmol) of dimethyl 1,3-acetonedicarboxylate and 16.8 ml (162 mmol) of benzyl alcohol were combined at room temperature. The mixture was stirred at 170-180 C, and methanol formed was distilled off. The mixture was then first cooled to room temperature, and excess methanol and benzyl alcohol were then distilled off at 1 mbar and at most 150° C. The residue was separated by flash chromatography (500 g silica cartridge, cyclohexane/ethyl acetate gradient), giving the title compound. Yield 9.0 g (74% pure, 25% of theory)

LC/MS [Method 3]: $R_t$=2.38 min; MS (ESIneg): m/z=325 (M−H)$^-$.

Example 17.1B

Benzyl 1-(1-tert-butoxy-1-oxobutan-2-yl)-4-hydroxy-6-oxo-1,6-dihydropyridine-3-carboxylate (racemate)

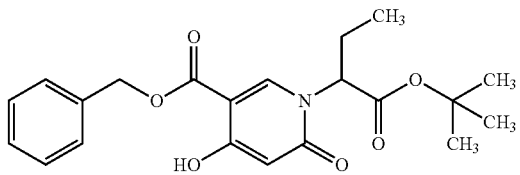 [SMILES: CCC(C(=O)OC(C)(C)C)n1cc(C(=O)OCc2ccccc2)c(O)cc1=O]

1.00 g (74% pure, 2.27 mmol) of dibenzyl 1,3-acetonedicarboxylate and 515 mg (3.17 mmol) of diethoxymethyl acetate were heated under reflux at 100° C. for 2.5 h. The mixture was cooled to room temperature and the reaction mixture was codistilled three times with toluene. The residue was dissolved in 8 ml of ethanol and a solution of 387 mg (2.38 mmol) of tert-butyl 2-aminobutanoate in 2 ml of ethanol was added at 0° C. The mixture was stirred at room temperature for 1 h, and 0.53 ml (2.3 mmol) of sodium ethoxide (21% in ethanol) was then added dropwise. After 30 min at room temperature, a further 0.26 ml (1.2 mmol) of sodium ethoxide (21% in ethanol) was added and the mixture was stirred for another 30 min. The reaction was terminated by addition of 50 ml of saturated aqueous ammonium chloride solution and 25 ml of ethyl acetate. The phases were separated and the aqueous phase was extracted three times with 50 ml of ethyl acetate. The combined organic phases were washed with saturated aqueous sodium chloride solution, dried over magnesium sulphate and filtered, and the solvent was removed under reduced pressure. The crude product was separated by flash chromatography (100 g silica cartridge, cyclohexane/ethyl acetate gradient), giving the title compound. Yield 0.46 g (75% pure, 39% of theory)

LC/MS [Method 1]: $R_t$=1.13 min; MS (ESIpos): m/z=388 (M+H)$^+$.

Example 17.1C

2-{5-[(Benzyloxy)carbonyl]-4-hydroxy-2-oxopyridin-1(2H)-yl}butanoic acid (racemate)

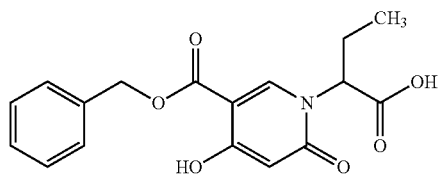 [SMILES: CCC(C(=O)O)n1cc(C(=O)OCc2ccccc2)c(O)cc1=O]

At 0° C. (ice bath cooling), 0.92 ml (12 mmol) of trifluoroacetic acid was added to a solution of 460 mg (1.19 mmol) of benzyl 1-(1-tert-butoxy-1-oxobutan-2-yl)-4-hydroxy-6-oxo-1,6-dihydropyridine-3-carboxylate (racemate) in 1.2 ml of dichloromethane. The mixture was warmed to room temperature and then stirred for another 3 h. The solvent was removed under reduced pressure and the residue was then codistilled three times with 10 ml of toluene. The crude product was purified by preparative HPLC (column: Chromatorex C18, 10 μm, 125 mm×30 mm, mobile phase: acetonitrile/0.05%-formic acid gradient (0 to 3 min 10% acetonitrile, to 35 min 90% acetonitrile and for a further 3 min 90% acetonitrile)], giving the title compound. Yield: 193 mg (49% of theory)

LC/MS [Method 1]: $R_t$=0.85 min; MS (ESIpos): m/z=332 (M+H)$^+$, $^1$H-NMR (400 MHz, DMSO-d$_6$): δ [ppm]=13.0 (br. s, 1H), 10.9 (s, 1H), 8.38 (s, 1H), 7.48-7.32 (m, 5H), 5.70 (s, 1H), 5.37-5.28 (m, 2H), 5.07 (dd, 1H), 2.16-1.93 (m, 2H), 0.78 (t, 3H).

Example 17.1D

Benzyl 4-hydroxy-6-oxo-1-[1-oxo-1-(pyrazol[1,5-a]pyridin-5-ylamino)butan-2-yl]-1,6-dihydropyridine-3-carboxylate (racemate)

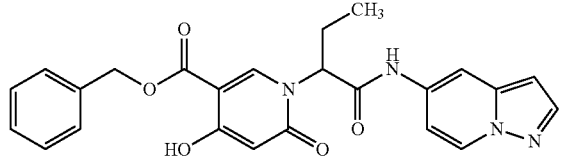 [SMILES: CCC(C(=O)Nc1ccn2nccc2c1)n1cc(C(=O)OCc2ccccc2)c(O)cc1=O]

193 mg (583 μmol.) of 2-{5-[(benzyloxy)carbonyl]-4-hydroxy-2-oxopyridin-1(2H)-yl}butanoic acid (racemate) and 116 mg (874 μmol, 1.5 eq.) of pyrazol[1,5-a]pyridine-5-amine were reacted according to General Method 5D. Yield: 233 mg (purity 94%, 84% of theory)

LC/MS [Method 1]: $R_t$=0.95 min; MS (ESIpos): m/z=447 (M+H)$^+$.

Example 17.1E

Benzyl 6-oxo-1-[1-oxo-1-(pyrazol[1,5-a]pyridin-5-ylamino)butan-2-yl]-4-{[(trifluoromethyl)sulphonyl]-oxy}-1,6-dihydropyridine-3-carboxylate (racemate)

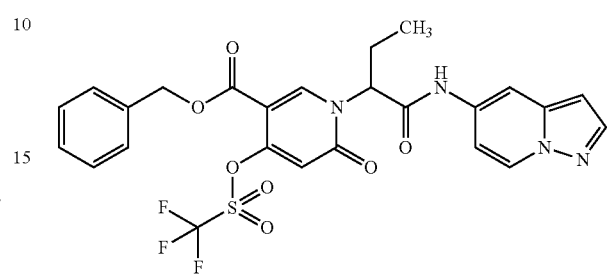

233 mg (94% pure, 491 μmol) of benzyl 4-hydroxy-6-oxo-1-[1-oxo-1-(pyrazol[1,5-a]pyridin-5-ylamino)butan-2-yl]-1,6-dihydropyridine-3-carboxylate (racemate) were dissolved in 5 ml of dichloromethane, and the reaction solution was cooled to −78° C. At −78° C., 171 μl (1.23 mmol) of triethylamine and 303 mg (736 μmol) of 1-{bis[(trifluoromethyl)sulphonyl]methyl}-4-tert-butylbenzene were added, and the mixture was stirred at room temperature overnight. 3 ml of dimethylformamide were then added dropwise, and the mixture was stirred at room temperature for another 1 h. The solvent was removed under reduced pressure. The residue was purified by flash chromatography (cyclohexane/ethyl acetate gradient), giving the title compound. Yield: 185 mg (65% of theory)

LC/MS [Method 1]: $R_t$=1.15 min; MS (ESIpos): m/z=579 (M+H)$^+$.

Example 17.1F

Benzyl 4-(5-chloro-2-cyanophenyl)-6-oxo-1-[1-oxo-1-(pyrazol[1,5-a]pyridin-5-ylamino)butan-2-yl]-1,6-dihydropyridine-3-carboxylate (racemate)

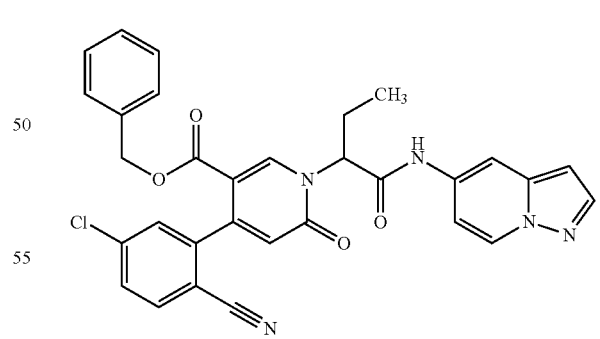

133 mg (959 μmol) of potassium carbonate were dried in the reaction vessel, and 185 mg (320 μmol) of benzyl 6-oxo-1-[1-oxo-1-(pyrazol[1,5-a]pyridin-5-ylamino)butan-2-yl]-4-{[(trifluoromethyl)sulphonyl]-oxy}-1,6-dihydropyridine-3-carboxylate (racemate), 67 mg (0.37 mmol) of 5-chloro-2-cyanophenylboronic acid and 4 ml of dioxane were then added. The suspension was degassed, 37 mg (32 μmol) of tetrakis(triphenylphosphine)palladium(0) were added and the mixture was shaken at 110° C. for 1 h. The reaction was terminated by addition of water and ethyl acetate. The mixture was acidified to pH=6 using 1N hydrochloric acid, and the phases were separated. The aqueous phase was extracted three times with ethyl acetate, the combined organic phases were dried over magnesium sulphate and filtered and the solvent was removed under reduced pressure. The crude product was purified by flash chromatography (cyclohexane/ethyl acetate gradient), giving the title compound. Yield: 147 mg (80% of theory)

LC/MS [Method 1]: $R_t$=1.11 min; MS (ESIpos): m/z=566 (M+H)$^+$.

WORKING EXAMPLES

General Method 1: Amide Coupling Using HATU/DIEA

Under argon and at RT, the appropriate amine (1.1 eq.), N,N-diisopropylethylamine (DIEA) (2.2 eq.) and a solution of HATU (1.2 eq.) in a little dimethylformamide were added to a solution of the appropriate carboxylic acid (1.0 eq.) in dimethylformamide (about 7-15 ml/mmol). The reaction mixture was stirred at RT. After addition of water/ethyl acetate and phase separation, the organic phase was washed with water and with saturated aqueous sodium chloride solution, dried (sodium sulphate or magnesium sulphate), filtered and concentrated under reduced pressure. The crude product was then purified either by normal phase chromatography (mobile phase: cyclohexane/ethyl acetate mixtures or dichloromethane/methanol mixtures) or by preparative RP-HPLC (water/acetonitrile gradient or water/methanol gradient).

General Method 2: Hydrolysis of a Methyl or Ethyl Ester with Lithium Hydroxide

At RT, lithium hydroxide (2-4 eq.) was added to a solution of the appropriate ester (1.0 eq.) in a mixture of tetrahydrofuran/water (3:1, about 7-15 ml/mmol), and the mixture was stirred at RT. The reaction mixture was then adjusted to pH 1 using aqueous hydrochloric acid solution (1N). After addition of water/ethyl acetate, the aqueous phase was extracted three times with ethyl acetate. The combined organic phases were dried (sodium sulphate or magnesium sulphate), filtered and concentrated under reduced pressure. The crude product was then purified either by normal phase chromatography (mobile phase: cyclohexane/ethyl acetate mixtures or dichloromethane/methanol mixtures) or by preparative RP-HPLC (water/acetonitrile gradient or water/methanol gradient).

General Method 3: Hydrolysis of a Tert-Butyl Ester or a Boc-Protected Amine Using TFA At RT, TFA (20 eq.) was added to a solution of the appropriate tert-butyl ester derivative or a Boc-protected amine (1.0 eq.) in dichloromethane (about 25 ml/mmol), and the mixture was stirred at RT for 1-8 h. Subsequently, the reaction mixture was concentrated under reduced pressure. The residue was co-evaporated repeatedly with dichloromethane and/or toluene. The crude product was then purified by preparative RP-HPLC (mobile phase: acetonitrile/water gradient or water/methanol gradient).

General Method 4: Amide Coupling with OXIMA/DIC

N,N'-Diisopropylcarbodiimide (DIC) (1 eq.) was added dropwise to a degassed solution of the appropriate carboxylic acid (1 eq.), aniline (0.1 eq.) and ethyl hydroxyiminocyanoacetate (Oxima) (0.1-1 eq.) in dimethylformamide (0.1M), and the resulting reaction solution was stirred at RT to 40° C. for 8-24 h. The solvent was removed under reduced pressure. The residue was either admixed with water and the desired product was filtered off or purified by normal phase chromatography (cyclohexane/ethyl acetate gradient) or preparative RP-HPLC (water/acetonitrile gradient or water/methanol gradient).

General Method 5: Amide Coupling Using T3P/DIEA

Under argon and at 0° C., N,N-diisopropylethylamine (3 eq.) and propylphosphonic anhydride (T3P, 50% in dimethylformamide, 3 eq.) were added dropwise to a solution of the carboxylic acid and the appropriate amine (1.1-1.5 eq.) in dimethylformamide (0.15-0.05 mmol). The reaction mixture was stirred at RT and then concentrated under reduced pressure. After addition of water/ethyl acetate and phase separation, the aqueous phase was extracted twice with ethyl acetate. The combined organic phases were dried (sodium sulphate or magnesium sulphate), filtered and concentrated under reduced pressure. The crude product was then purified either by flash chromatography (silica gel 60, mobile phase: cyclohexane/ethyl acetate mixtures or dichloromethane/methanol mixtures) or by preparative HPLC (Reprosil C18, water/acetonitrile gradient or water/methanol gradient).

General Method 6: Amide Coupling Using T3P/Pyridine

A solution of the appropriate carboxylic acid (1 eq.) and the appropriate amine (1.1-1.5 eq.) in pyridine (about 0.1M) was heated to 60° C., and T3P (50% in ethyl acetate, 15 eq.) was added dropwise. Alternatively, T3P was added at RT and the mixture was then stirred at RT or heated to 60 to 90° C. After 1-20 h, the reaction mixture was cooled to RT, and water and ethyl acetate were added. The aqueous phase was extracted with ethyl acetate. The combined organic phases were washed with aqueous buffer solution (pH=5), with saturated aqueous sodium bicarbonate solution and with saturated aqueous sodium chloride solution, dried over sodium sulphate and concentrated under reduced pressure. The crude product was then optionally purified either by normal phase chromatography (mobile phase: cyclohexane/ethyl acetate mixtures or dichloromethane/methanol mixtures) or by preparative RP-HPLC (water/acetonitrile gradient or water/methanol gradient).

Example 1

2-({2-[4-(5-Chloro-2-cyanophenyl)-5-methoxy-2-oxopyridin-1(2H)-yl]butanoyl}amino)imidazo[1,2-a]pyridine-6-carboxylic acid (racemate)

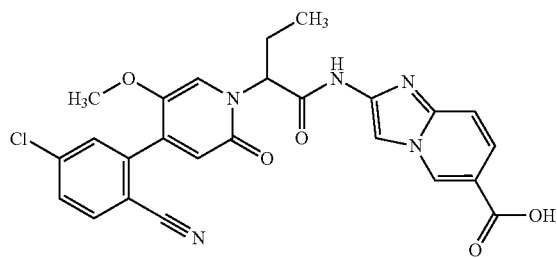 [SMILES: CCC(C(=O)Nc1cn2cc(C(=O)O)ccc2n1)n1cc(OC)c(-c2cc(Cl)ccc2C#N)cc1=O]

59 mg (0.11 mmol) of methyl 2-({2-[4-(5-chloro-2-cyanophenyl)-5-methoxy-2-oxopyridin-1(2H)-yl]butanoyl}amino)imidazo[1,2-a]pyridine-6-carboxylate (racemate) were hydrolysed with lithium hydroxide according to General Method 2. After acidification with aqueous hydrochloric acid (1N), the desired product could be isolated as precipitate. Yield: 45 mg (75% of theory)

LC/MS [Method 1]: $R_t$=0.88 min; MS (ESIpos): m/z=506 (M+H)$^+$, $^1$H-NMR (400 MHz, DMSO-d$_6$): δ [ppm]=13.19 (s, 1H), 11.34 (s, 1H), 9.25 (s, 1H), 8.29 (s, 1H), 8.00 (d, 1H), 7.79-7.70 (m, 2H), 7.63 (dd, 1H), 7.54-7.46 (m, 2H), 6.53 (s, 1H), 5.75 (dd, 1H), 3.70 (s, 3H), 2.28-2.10 (m, 2H), 0.89 (t, 3H).

Example 2

6-({2-[4-(5-Chloro-2-cyanophenyl)-5-methoxy-2-oxopyridin-1(2H)-yl]butanoyl}amino)imidazo[1,2-a]pyridine-2-carboxylic acid (racemate)

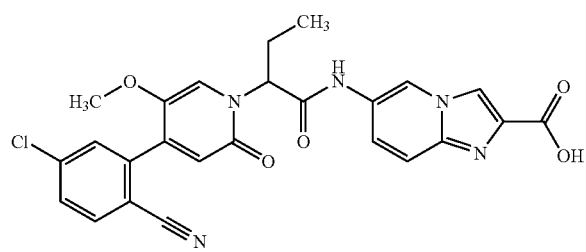 [SMILES: CCC(C(=O)Nc1ccc2nc(C(=O)O)cn2c1)n1cc(OC)c(-c2cc(Cl)ccc2C#N)cc1=O]

86 mg (0.16 mmol) of ethyl 6-({2-[4-(5-chloro-2-cyanophenyl)-5-methoxy-2-oxopyridin-1(2H)-yl]butanoyl}amino)imidazo[1,2-a]pyridine-2-carboxylate (racemate) were hydrolysed with lithium hydroxide according to General Method 2. After aqueous work-up, the crude product was purified by preparative RP-HPLC (Reprosil C18, water/acetonitrile gradient). Yield: 16 mg (19% of theory)

LC/MS [Method 1]: $R_t$=0.74 min; MS (ESIpos): m/z=506 (M+H)$^+$, $^1$H-NMR (400 MHz, DMSO-d$_6$): δ [ppm]=10.75 (s, 1H), 9.32 (s, 1H), 8.54 (s, 1H), 8.01 (d, 1H), 7.78-7.70 (m, 2H), 7.62 (d, 1H), 7.52 (s, 1H), 7.32 (dd, 1H), 6.55 (s, 1H), 5.66 (dd, 1H), 3.70 (s, 3H), 2.28-2.10 (m, 2H), 0.92 (s, 3H).

Example 3

7-({2-[4-(5-Chloro-2-cyanophenyl)-5-methoxy-2-oxopyridin-1(2H)-yl]butanoyl}amino)imidazo[1,2-a]pyridine-2-carboxylic acid (racemate)

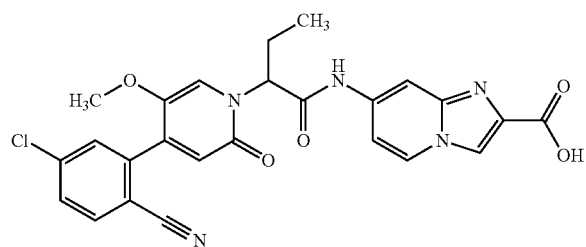 [SMILES: CCC(C(=O)Nc1ccn2cc(C(=O)O)nc2c1)n1cc(OC)c(-c2cc(Cl)ccc2C#N)cc1=O]

18 mg (0.03 mmol) of ethyl 7-({2-[4-(5-chloro-2-cyanophenyl)-5-methoxy-2-oxopyridin-1(2H)-yl]butanoyl}amino)imidazo[1,2-a]pyridine-2-carboxylate (racemate) were hydrolysed with lithium hydroxide according to General Method 2. After aqueous work-up, the crude product was purified by preparative RP-HPLC (Reprosil C18, water/acetonitrile gradient). Yield: 8 mg (45% of theory)

LC/MS [Method 8]: $R_t$=0.95 min; MS (ESIpos): m/z=506 (M+H)$^+$, $^1$H-NMR (400 MHz, DMSO-d$_6$): δ [ppm]=10.82 (s, 1H), 8.48 (d, 1H), 8.32 (s, 1H), 8.04-7.97 (m, 2H), 7.78-7.70 (m, 2H), 7.51 (s, 1H), 7.11 (dd, 1H), 6.55 (s, 1H), 5.62 (dd, 1H), 3.70 (s, 3H), 2.31-2.13 (m, 2H), 0.92 (s, 3H).

Example 4

2-[4-(5-Chloro-2-cyanophenyl)-5-methoxy-2-oxopyridin-1(2H)-yl]-N-(imidazo[1,2-a]pyridin-6-yl)butanamide (racemate)

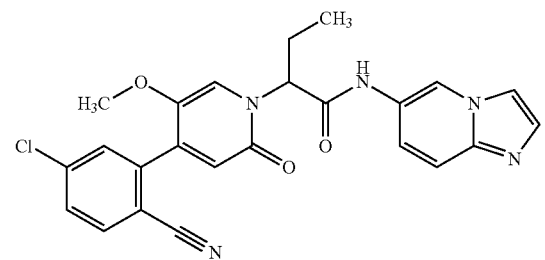 [SMILES: CCC(C(=O)Nc1ccc2nccn2c1)n1cc(OC)c(-c2cc(Cl)ccc2C#N)cc1=O]

87 mg (0.25 mmol) of 2-[4-(5-chloro-2-cyanophenyl)-5-methoxy-2-oxopyridin-1(2H)-yl]butanoic acid (racemate) and 44 mg (0.30 mmol, 1.2 eq.) of imidazo[1,2-a]pyridine-6-amine were reacted according to General Method 1. After aqueous work-up, the crude product was purified by preparative RP-HPLC (Reprosil C18, water/acetonitrile gradient). Yield: 8 mg (7% of theory)

LC/MS [Method 8]: $R_t$=0.93 min; MS (ESIpos): m/z=462 (M+H)$^+$, $^1$H-NMR (400 MHz, DMSO-d$_6$): δ [ppm]=10.64 (s, 1H), 9.25 (s, 1H), 8.03-7.97 (m, 2H), 7.77-7.71 (m, 2H), 7.57 (d, 1H), 7.54 (d, 2H), 7.23 (dd, 1H), 6.55 (s, 1H), 5.66 (dd, 1H), 3.70 (s, 3H), 2.28-2.19 (m, 2H), 0.92 (t, 3H).

Example 5

6-({2-[4-(5-Chloro-2-cyanophenyl)-5-methoxy-2-oxopyridin-1(2H)-yl]-3-cyclobutylpropanoyl}-amino)imidazo[1,2-a]pyridine-2-carboxylic acid (racemate)

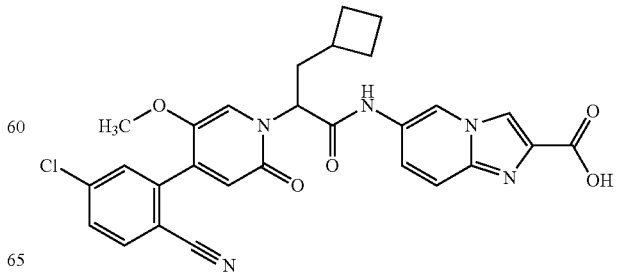

69 mg (0.12 mmol) of ethyl 2-({6-[4-(5-chloro-2-cyanophenyl)-5-methoxy-2-oxopyridin-1(2H)-yl]-3-cyclobutylpropanoyl}amino)imidazo[1,2-a]pyridine-2-carboxylate (racemate) were hydrolysed with lithium hydroxide according to General Method 2. After aqueous work-up, the crude product was purified by preparative RP-HPLC (Reprosil C18, water/acetonitrile gradient). Yield: 38 mg (58% of theory)

LC/MS [Method 1]: $R_t$=0.88 min; MS (ESIpos): m/z=546 (M+H)$^+$, $^1$H-NMR (400 MHz, DMSO-d$_6$): δ [ppm]=10.74 (s, 1H), 9.32 (s, 1H), 8.54 (s, 1H), 8.00 (d, 1H), 7.78-7.70 (m, 2H), 7.62 (d, 1H), 7.53 (s, 1H), 7.34 (dd, 1H), 6.53 (s, 1H), 5.75-5.66 (m, 1H), 3.69 (s, 3H), 2.35-2.18 (m, 3H), 2.02-1.90 (m, 2H), 1.86-1.61 (m, 4H).

Example 6

6-({[4-(5-Chloro-2-cyanophenyl)-5-methoxy-2-oxopyridin-1(2H)-yl]acetyl}amino)imidazo[1,2-a]pyridine-2-carboxylic acid

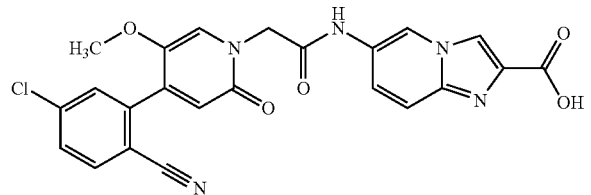 [SMILES: COc1cn(CC(=O)Nc2ccc3nc(C(=O)O)cn3c2)c(=O)cc1-c1cc(Cl)ccc1C#N]

99 mg (0.20 mmol) of ethyl 6-({[4-(5-chloro-2-cyanophenyl)-5-methoxy-2-oxopyridin-1(2H)-yl]acetyl}amino)imidazo[1,2-a]pyridine-2-carboxylate were hydrolysed with lithium hydroxide according to General Method 2. After acidification with aqueous hydrochloric acid (1N), the desired product could be isolated as precipitate and purified further by stirring with acetonitrile/water (2:1). Yield: 42 mg (45% of theory)

LC/MS [Method 1]: $R_t$=0.69 min; MS (ESIpos): m/z=478 (M+H)$^+$, $^1$H-NMR (400 MHz, DMSO-d$_6$): δ [ppm]=10.87 (s, 1H), 9.42 (s, 1H), 8.70 (s, 1H), 8.00 (d, 1H), 7.79-7.68 (m, 3H), 7.62 (s, 1H), 7.56 (d, 1H), 6.52 (s, 1H), 4.86 (s, 2H), 3.64 (s, 3H).

Example 7

6-[(2-{4-[5-Chloro-2-(difluoromethoxy)phenyl]-5-methoxy-2-oxopyridin-1(2H)-yl}butanoyl)amino]-imidazo[1,2-a]pyridine-2-carboxylic acid (racemate)

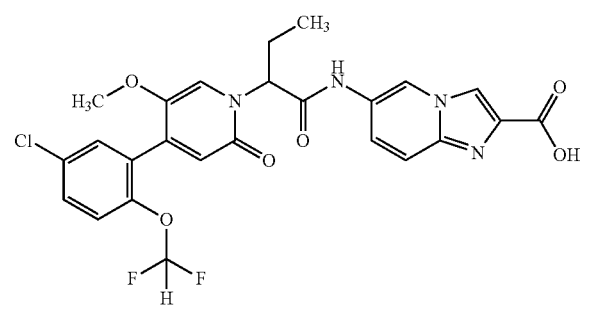 [SMILES: CCC(C(=O)Nc1ccc2nc(C(=O)O)cn2c1)n1cc(OC)c(-c2cc(Cl)ccc2OC(F)F)cc1=O]

198 mg (0.28 mmol) of ethyl 6-[(2-{4-[5-chloro-2-(difluoromethoxy)phenyl]-5-methoxy-2-oxopyridin-1(2H)-yl}butanoyl)amino]imidazo[1,2-a]pyridine-2-carboxylate (racemate) were hydrolysed with lithium hydroxide according to General Method 2. After aqueous work-up, the crude product was purified by preparative RP-HPLC (Reprosil C18, water/acetonitrile gradient). Yield: 85 mg (56% of theory)

LC/MS [Method 1]: $R_t$=0.85 min; MS (ESIpos): m/z=547 (M+H)$^+$, $^1$H-NMR (400 MHz, DMSO-d$_6$): δ [ppm]=10.74 (s, 1H), 9.32 (s, 1H), 8.55 (s, 1H), 7.63 (d, 1H), 7.58 (dd, 1H), 7.50 (dd, 1H), 7.41 (s, 1H), 7.37-7.26 (m, 2H), 7.14 (t, 1H), 6.41 (s, 1H), 5.64 (dd, 1H), 3.64 (s, 3H), 2.27-2.05 (m, 2H), 0.91 (t, 3H).

Example 8

6-[({5-Chloro-4-[5-chloro-2-(difluoromethoxy)phenyl]-2-oxopyridin-1(2H)-yl}acetyl)amino]imidazo[1,2-a]pyridine-2-carboxylic acid

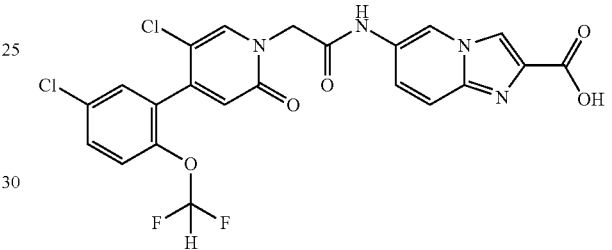

99 mg (0.18 mmol) of ethyl 6-[({5-chloro-4-[5-chloro-2-(difluoromethoxy)phenyl]-2-oxopyridin-1(2H)-yl}acetyl)amino]imidazo[1,2-a]pyridine-2-carboxylate were hydrolysed with lithium hydroxide according to General Method 2. After aqueous work-up, the crude product was purified by preparative RP-HPLC (Reprosil C18, water/acetonitrile gradient). Yield: 26 mg (28% of theory)

LC/MS [Method 1]: $R_t$=0.77 min; MS (ESIpos): m/z=523 (M+H)$^+$, $^1$H-NMR (400 MHz, DMSO-d$_6$): δ [ppm]=10.73 (s, 1H), 9.31 (s, 1H), 8.60 (s, 1H), 8.13 (s, 1H), 7.68 (d, 1H), 7.64 (dd, 1H), 7.52 (d, 1H), 7.42-7.34 (m, 2H), 7.26 (t, 1H), 6.52 (s, 1H), 4.85 (s, 2H).

Example 9

6-({2-[4-(5-Chloro-2-cyanophenyl)-5-methoxy-2-oxopyridin-1(2H)-yl]-3-[(2S)-tetrahydro-2H-pyran-2-yl]propanoyl}amino)imidazo[1,2-a]pyridine-2-carboxylic acid (mixture of enantiomerically pure diastereomers)

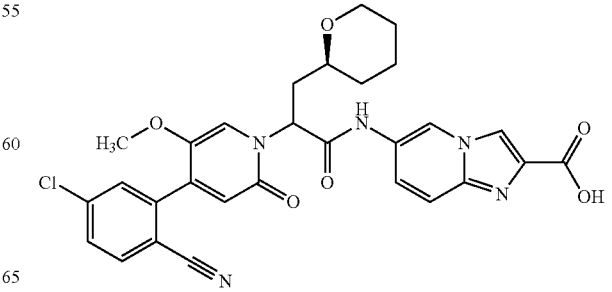

162 mg (0.27 mmol) of ethyl 6-({2-[4-(5-chloro-2-cyanophenyl)-5-methoxy-2-oxopyridin-1(2H)-yl]-3-[(2S)-tetrahydro-2H-pyran-2-yl]propanoyl}amino)imidazo[1,2-a]pyridine-2-carboxylate (mixture of enantiomerically pure diastereomers) were hydrolysed with lithium hydroxide according to General Method 2. After aqueous work-up, the crude product was purified by preparative RP-HPLC (Reprosil C18, water/acetonitrile gradient). Yield: 61 mg (40% of theory)

LC/MS [Method 1]: $R_t$=0.81 min; MS (ESIpos): m/z=576 (M+H)$^+$, $^1$H-NMR (400 MHz, DMSO-d$_6$): δ [ppm]=10.69/10.58 (2×s, 1H), 9.31/9.28 (2×s, 1H), 8.56-8.51 (m, 1H), 8.03-7.97 (m, 1H), 7.77-7.70 (m, 2H), 7.63-7.57 (m, 1H), 7.54/7.50 (2×s, 1H), 7.42-7.33 (m, 1H), 6.53/6.52 (2×s, 1H), 5.85/5.77 (t/dd, 1H), 3.93-3.79 (m, 1H), 3.69 (s, 3H), 3.25-3.15 (m, 1H), 3.14-3.05 (m, 1H), 2.40-2.09 (m, 2H), 1.80-1.71 (m, 1H), 1.68-1.56 (m, 1H), 1.48-1.35 (m, 3H), 1.34-1.20 (m, 1H).

Example 10

Ethyl 6-({2-[4-(5-chloro-2-cyanophenyl)-5-methoxy-2-oxopyridin-1(2H)-yl]-4-methoxybutanoyl}amino)imidazo[1,2-a]pyridine-3-carboxylate (racemate)

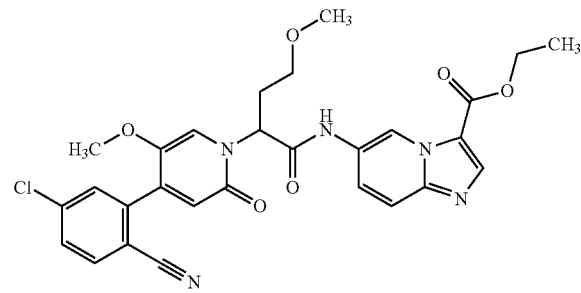 [SMILES: CCOC(=O)c1cnc2ccc(NC(=O)C(CCOC)n3cc(OC)c(-c4cc(Cl)ccc4C#N)cc3=O)cn12]

According to General Method 6, 80 mg (0.21 mmol) of 2-[4-(5-chloro-2-cyanophenyl)-5-methoxy-2-oxopyridin-1(2H)-yl]-4-methoxybutanoic acid (racemate) and 65 mg (0.32 mmol, 1.5 eq.) of ethyl 6-aminoimidazo[1,2-a]pyridine-3-carboxylate were initially charged in pyridine at 60° C. and reacted with one another by addition of T3P. The crude product was purified by preparative HPLC (Chromatorex 125 mm×30 mm, 10 μm, mobile phase: water/acetonitrile, gradient 10-90% acetonitrile). Yield: 66 mg (55% of theory)

LC/MS [Method 1]: $R_t$=0.96 min; MS (ESIpos): m/z=564 (M+H)$^+$, $^1$H-NMR (400 MHz, DMSO-d$_6$): δ [ppm]=10.81 (s, 1H), 10.09 (d, 1H), 8.25 (s, 1H), 8.00 (d, 1H), 7.80 (d, 1H), 7.76-7.71 (m, 2H), 7.66 (dd, 1H), 7.54 (s, 1H), 6.54 (s, 1H), 5.78 (dd, 1H), 4.35 (q, 2H), 3.71 (s, 3H), 3.46-3.39 (m, 1H), 3.30-3.25 (m, 1H), 3.22 (s, 3H), 2.49-2.36 (m, 2H), 1.34 (t, 3H).

Example 11

Ethyl 7-({2-[4-(5-chloro-2-cyanophenyl)-5-methoxy-2-oxopyridin-1(2H)-yl]-4-methoxybutanoyl}amino)imidazo[1,2-a]pyridine-2-carboxylate (racemate)

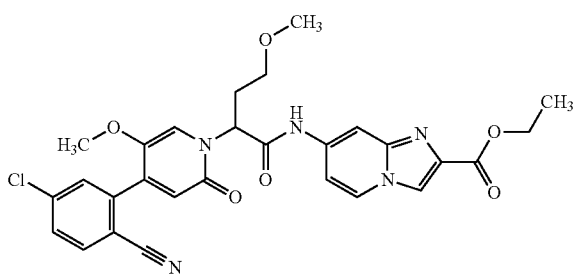 [SMILES: CCOC(=O)c1cn2ccc(NC(=O)C(CCOC)n3cc(OC)c(-c4cc(Cl)ccc4C#N)cc3=O)cc2n1]

According to General Method 6, 75 mg (0.20 mmol) of 2-[4-(5-chloro-2-cyanophenyl)-5-methoxy-2-oxopyridin-1(2H)-yl]-4-methoxybutanoic acid (racemate) and 53 mg (0.26 mmol, 1.3 eq.) of ethyl 7-aminoimidazo[1,2-a]pyridine-2-carboxylate were initially charged in pyridine at 60° C. and reacted with one another by addition of T3P. The crude product was purified by preparative HPLC (Chromatorex 125 mm×30 mm, 10 μm, mobile phase: gradient water/acetonitrile: 10-90% acetonitrile). Yield: 83 mg (74% of theory)

LC/MS [Method 1]: $R_t$=0.91 min; MS (ESIpos): m/z=564 (M+H)$^+$, $^1$H-NMR (400 MHz, DMSO-d$_6$): δ [ppm]=10.69 (s, 1H), 9.32-9.29 (m, 1H), 8.60 (s, 1H), 8.02-7.98 (m, 1H), 7.76-7.72 (m, 2H), 7.64-7.60 (m, 1H), 7.52 (s, 1H), 7.38 (dd, 1H), 6.54 (s, 1H), 5.78 (dd, 1H), 4.30 (q, 2H), 3.69 (s, 3H), 3.45-3.38 (m, 1H), 3.30-3.25 (m, 1H), 3.22 (s, 3H), 2.48-2.36 (m, 2H), 1.31 (t, 3H).

Example 12

7-({2-[4-(5-Chloro-2-cyanophenyl)-5-methoxy-2-oxopyridin-1(2H)-yl]-4-methoxybutanoyl}amino)imidazo[1,2-a]pyridine-2-carboxamide (racemate)

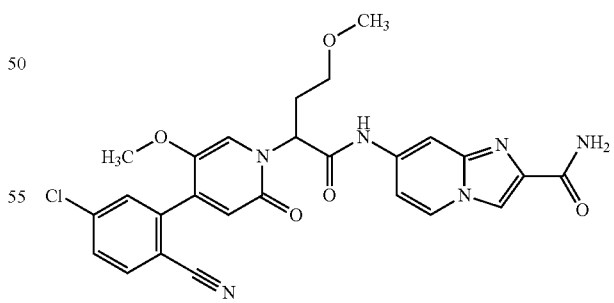

According to General Method 6, 65 mg (0.17 mmol) of 2-[4-(5-chloro-2-cyanophenyl)-5-methoxy-2-oxopyridin-1(2H)-yl]-4-methoxybutanoic acid (racemate) and 44 mg (90% pure, 0.22 mmol, 1.3 eq.) of 7-aminoimidazo[1,2-a]pyridine-2-carboxamide were initially charged in pyridine at 60° C. and reacted with one another by addition of T3P. The crude product was purified by preparative HPLC (Chroma-

Example 13

2-[4-(5-Chloro-2-cyanophenyl)-5-methoxy-2-oxopyridin-1(2H)-yl]-N-(imidazo[1,2-a]pyridin-6-yl)-4-methoxybutanamide (racemate)

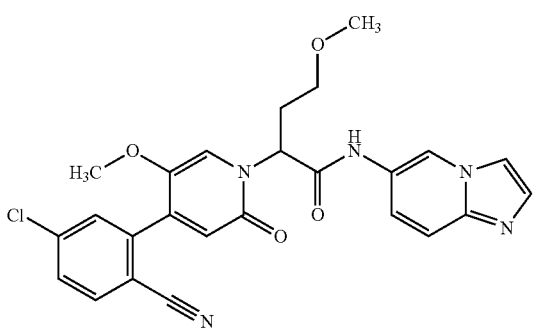 [SMILES: COCCC(C(=O)Nc1ccc2nccn2c1)n1cc(OC)c(-c2cc(Cl)ccc2C#N)cc1=O]

200 mg (0.53 mmol) of 2-[4-(5-chloro-2-cyanophenyl)-5-methoxy-2-oxopyridin-1(2H)-yl]-4-methoxybutanoic acid (racemate) and 78 mg (0.58 mmol, 1.1 eq.) of imidazo[1,2-a]pyridine-6-amine were reacted according to General Method 1. The crude product was purified by flash chromatography (silica gel 50, dichloromethane/methanol gradient) and subsequent thick-layer chromatography (dichloromethane/methanol 10:1). Yield: 47 mg (purity 90%, 16% of theory)

LC/MS [Method 2]: $R_t$=1.80 min; MS (ESIpos): m/z=492 (M+H)$^+$, $^1$H-NMR (400 MHz, DMSO-d$_6$): δ [ppm]=10.59 (s, 1H), 9.23 (s, 1H), 8.03-7.95 (m, 2H), 7.76-7.67 (m, 2H), 7.58-7.50 (m, 3H), 7.25 (dd, 1H), 6.54 (s, 1H), 5.79 (dd, 1H), 3.69 (s, 3H), 3.45-3.37 (m, 1H), 3.31-3.26 (m, 1H), 3.22 (s, 3H), 2.48-2.35 (m, 2H).

torex 125 mm×30 mm, 10 μm, mobile phase: gradient water/acetonitrile: 10%-90% acetonitrile) and then by further preparative HPLC (Kinetex 5 μm C18 150 mm×21.2 mm, gradient water/acetonitrile: 5%-50% acetonitrile). Yield: 8 mg (9% of theory)

LC/MS [Method 1]: $R_t$=0.77 min; MS (ESIpos): m/z=535 (M+H)$^+$, $^1$H-NMR (400 MHz, DMSO-d$_6$): δ [ppm]=10.66 (s, 1H), 9.31-9.29 (m, 1H), 8.39 (s, 1H), 8.02-7.98 (m, 1H), 7.76-7.71 (m, 2H), 7.64-7.61 (m, 1H), 7.58 (d, 1H), 7.53 (s, 1H), 7.38-7.32 (m, 2H), 6.54 (s, 1H), 5.79 (dd, 1H), 3.69 (s, 3H), 3.45-3.38 (m, 1H), 3.28-3.24 (m, 1H), 3.22 (s, 3H), 2.48-2.38 (m, 2H).

Example 14

2-[5-Chloro-4-(5-chloro-2-cyanophenyl)-2-oxopyridin-1(2H)-yl]-N-(imidazo[1,2-a]pyridin-6-yl)-4-methoxybutanamide (racemate)

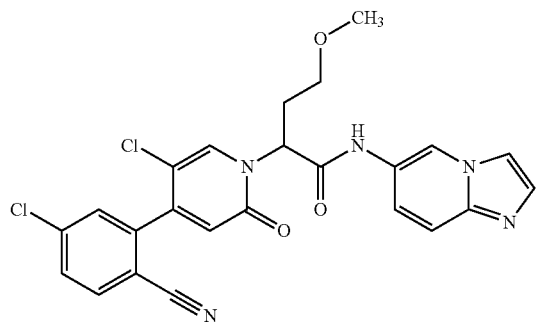 [SMILES: COCCC(C(=O)Nc1ccc2nccn2c1)n1cc(Cl)c(-c2cc(Cl)ccc2C#N)cc1=O]

50 mg (0.13 mmol) of 2-[5-chloro-4-(5-chloro-2-cyanophenyl)-2-oxopyridin-1(2H)-yl]-4-methoxybutanoic acid (racemate) and 28 mg (0.19 mmol, 1.5 eq.) of imidazo[1,2-a]pyridine-6-amine were reacted according to General Method 6. The crude product was purified by preparative HPLC (water/acetonitrile/0.1% formic acid gradient). Yield: 20 mg (32% of theory)

LC/MS [Method 1]: $R_t$=0.75 min; MS (ESIpos): m/z=496 (M+H)$^+$, $^1$H-NMR (400 MHz, DMSO-d$_6$): δ [ppm]=10.66 (s, 1H), 9.23 (s, 1H), 8.23 (s, 1H), 8.09-8.04 (m, 1H), 7.98 (s, 1H), 7.84-7.76 (m, 2H), 7.60-7.50 (m, 2H), 7.24 (dd, 1H), 6.68 (s, 1H), 5.85-5.73 (m, 1H), 3.42 (dt, 1H), 3.29-3.24 (m, 1H), 3.21 (s, 3H), 2.46-2.38 (m, 2H).

Example 15

2-[4-(5-Chloro-2-cyanophenyl)-5-methoxy-2-oxopyridin-1(2H)-yl]-3-cyclobutyl-N-(imidazo[1,2-a]pyridin-6-yl)propanamide (racemate)

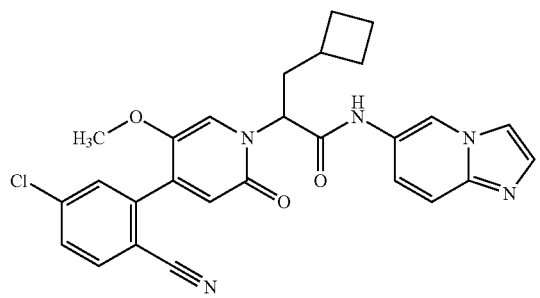 [SMILES: COc1cn(C(CC2CCC2)C(=O)Nc2ccc3nccn3c2)c(=O)cc1-c1cc(Cl)ccc1C#N]

123 mg (94% pure, 0.30 mmol) of 2-[4-(5-chloro-2-cyanophenyl)-5-methoxy-2-oxopyridin-1(2H)-yl]-3-cyclobutylpropanoic acid (racemate) and 47 mg (0.33 mmol, 1.1 eq.) of imidazo[1,2-a]pyridine-6-amine were reacted according to General Method 1. After aqueous work-up, the crude product was purified by preparative RP-HPLC (Reprosil C18, water/acetonitrile gradient). Yield: 45 mg (30% of theory)

LC/MS [Method 1]: $R_t$=0.81 min; MS (ESIpos): m/z=502 (M+H)$^+$, $^1$H-NMR (400 MHz, DMSO-d$_6$): δ [ppm]=10.63 (s, 1H), 9.24 (s, 1H), 8.03-7.97 (m, 2H), 7.77-7.70 (m, 2H), 7.59-7.50 (m, 3H), 7.24 (dd, 1H), 6.53 (s, 1H), 5.71 (t, 1H), 3.69 (s, 3H), 2.31-2.19 (m, 3H), 2.02-1.91 (m, 2H), 1.85-1.62 (m, 4H).

Example 16

2-[4-(5-Chloro-2-cyanophenyl)-5-methoxy-2-oxopyridin-1(2H)-yl]-3-(trans-4-hydroxycyclohexyl)-N-(imidazo[1,2-a]pyridin-6-yl)propanamide (racemate)

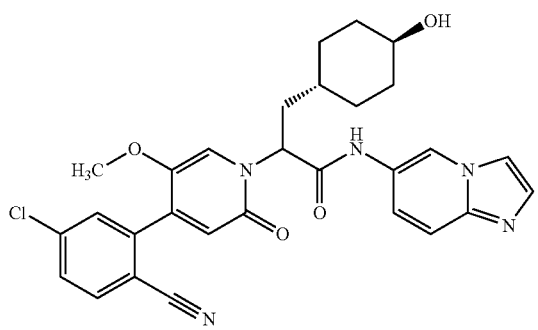 [SMILES: COc1cn(C(C[C@H]2CC[C@H](O)CC2)C(=O)Nc2ccc3nccn3c2)c(=O)cc1-c1cc(Cl)ccc1C#N]

63 mg (96 μmol) of 3-(trans-4-{[tert-butyl(dimethyl)silyl]oxy}cyclohexyl)-2-[4-(5-chloro-2-cyanophenyl)-5-methoxy-2-oxopyridin-1(2H)-yl]-N-(imidazo[1,2-a]pyridin-6-yl)propanamide (racemate) were initially charged in 5 ml of dimethylformamide, and 0.5 ml of aqueous hydrochloric acid (1N) was added. The reaction solution was stirred at room temperature for 1 h and then separated by preparative HPLC (column: Chromatorex C18, 10 μm, 125 mm×30 mm, solvent: acetonitrile/0.1%-formic acid gradient (0 to 3 min 10% acetonitrile, to 35 min 90% acetonitrile and for a further 3 min 90% acetonitrile), giving the title compound. Yield: 25.3 mg (48% of theory)

LC/MS [Method 1]: R$_t$=0.69 min; MS (ESIpos): m/z=546 (M+H)$^+$, $^1$H-NMR (400 MHz, DMSO-d$_6$): δ [ppm]=10.6 (s, 1H), 9.24-9.22 (m, 1H), 8.02-7.97 (m, 2H), 7.77-7.71 (m, 2H), 7.58-7.50 (m, 3H), 7.23 (dd, 1H), 6.55 (s, 1H), 5.85 (dd, 1H), 4.44 (d, 1H), 3.68 (s, 3H), 2.19-2.10 (m, 1H), 1.96-1.87 (m, 1H), 1.83-1.71 (m, 4H), 1.12-0.95 (m, 5H).

Example 17

2-[4-(5-Chloro-2-cyanophenyl)-5-methoxy-2-oxopyridin-1(2H)-yl]-N-(3-chloroimidazo[1,2-a]pyridin-6-yl)butanamide (racemate)

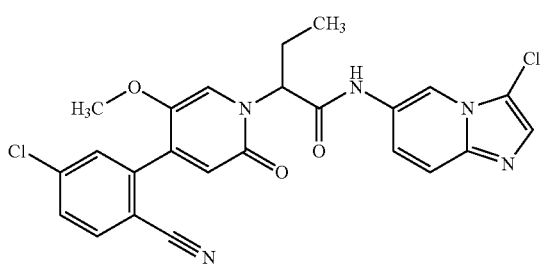 [SMILES: CCC(C(=O)Nc1ccc2ncc(Cl)n2c1)n1cc(OC)c(-c2cc(Cl)ccc2C#N)cc1=O]

At RT, 13 mg (0.10 mmol, 1.0 eq.) of N-chlorosuccinimide were added to a solution of 46 mg (0.25 mmol) of 2-[4-(5-chloro-2-cyanophenyl)-5-methoxy-2-oxopyridin-1(2H)-yl]-N-(imidazo[1,2-a]pyridin-6-yl)butanamide (racemate) in 2 ml of ethanol, and the mixture was stirred at RT overnight. After addition of water/ethyl acetate and phase separation, the aqueous phase was extracted with ethyl acetate. The combined organic phases were washed with saturated aqueous sodium chloride solution, dried (sodium sulphate), filtered and concentrated under reduced pressure. The residue was purified by preparative RP-HPLC (Reprosil C18, water/acetonitrile gradient). Yield: 18 mg (36% of theory)

LC/MS [Method 1]: R$_t$=0.91 min; MS (ESIpos): m/z=496 (M+H)$^+$, $^1$H-NMR (400 MHz, DMSO-d$_6$): δ [ppm]=10.84 (s, 1H), 9.09 (s, 1H), 8.00 (d, 1H), 7.77-7.71 (m, 2H), 7.70-7.65 (m, 2H), 7.52 (s, 1H), 7.36 (dd, 1H), 6.56 (s, 1H), 5.65 (dd, 1H), 3.70 (s, 3H), 2.30-2.12 (m, 2H), 0.93 (t, 3H).

Example 18

2-[4-(5-Chloro-2-cyanophenyl)-5-methoxy-2-oxopyridin-1(2H)-yl]-N-[2-(4-fluorophenyl)-imidazo[1,2-a]pyridin-6-yl]butanamide (racemate)

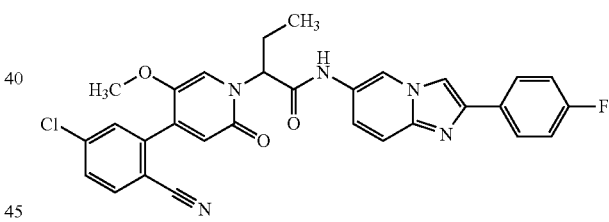

According to General Method 6, 80 mg (0.23 mmol) of 2-[4-(5-chloro-2-cyanophenyl)-5-methoxy-2-oxopyridin-1(2H)-yl]butanoic acid (racemate) and 96 mg (82% pure, 0.35 mmol, 1.5 eq.) of 2-(4-fluorophenyl)imidazo[1,2-a]pyridine-6-amine were initially charged in pyridine at 60° C. and reacted with one another by addition of T3P. The crude product was purified by preparative HPLC (Chromatorex 125 mm×30 mm, 10 μm, mobile phase: water/acetonitrile, gradient 10-90% acetonitrile). Yield: 80 mg (62% of theory)

LC/MS [Method 1]: R$_t$=0.88 min; MS (ESIpos): m/z=556 (M+H)$^+$, $^1$H-NMR (400 MHz, DMSO-d$_6$): δ [ppm]=10.68 (s, 1H), 9.23 (d, 1H), 8.43 (s, 1H), 8.00 (d, 1H), 7.98-7.93 (m, 2H), 7.76-7.72 (m, 2H), 7.59 (d, 1H), 7.53 (s, 1H), 7.30-7.23 (m, 3H), 6.56 (s, 1H), 5.67 (dd, 1H), 3.70 (s, 3H), 2.30-2.09 (m, 2H), 0.93 (t, 3H).

Example 19

2-[4-(5-Chloro-2-cyanophenyl)-5-methoxy-2-oxopyridin-1(2H)-yl]-N-[2-(4-fluorophenyl)-imidazo[1,2-a]pyridin-6-yl]-4-methoxybutanamide (racemate)

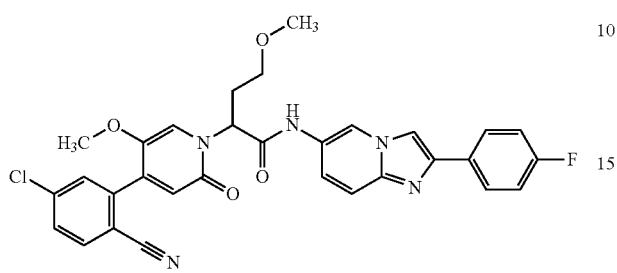

According to General Method 6, 75 mg (0.20 mmol) of 2-[4-(5-chloro-2-cyanophenyl)-5-methoxy-2-oxopyridin-1(2H)-yl]-4-methoxybutanoic acid (racemate) and 83 mg (82% pure, 0.30 mmol, 1.5 eq.) of 2-(4-fluorophenyl)imidazo[1,2-a]pyridine-6-amine were initially charged in pyridine at 60° C. and reacted with one another by addition of T3P. The crude product was purified by preparative HPLC (Chromatorex 125 mm×30 mm, 10 μm, mobile phase: water/acetonitrile, gradient: 10-90% acetonitrile). Yield: 53 mg (45% of theory)

LC/MS [Method 1]: $R_t$=0.86 min; MS (ESIpos): m/z=586 (M+H)$^+$, $^1$H-NMR (400 MHz, DMSO-d$_6$): δ [ppm]=10.63 (s, 1H), 9.21 (d, 1H), 8.43 (s, 1H), 8.02-7.98 (m, 1H), 7.98-7.93 (m, 2H), 7.76-7.72 (m, 2H), 7.58 (d, 1H), 7.54 (s, 1H), 7.30 (dd, 1H), 7.28-7.23 (m, 2H), 6.55 (s, 1H), 5.80 (dd, 1H), 3.70 (s, 3H), 3.46-3.39 (m, 1H), 3.30-3.26 (m, 1H), 3.23 (s, 3H), 2.48-2.35 (m, 2H).

Example 20

2-[4-(5-Chloro-2-cyanophenyl)-5-methoxy-2-oxopyridin-1(2H)-yl]-N-([1,2,4]triazolo[4,3-a]pyridin-6-yl)butanamide (racemate)

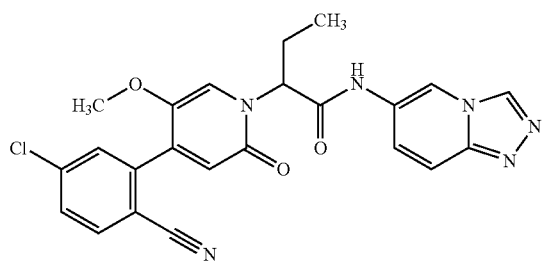 [SMILES: CCC(C(=O)Nc1ccc2nncn2c1)n1cc(OC)c(-c2cc(Cl)ccc2C#N)cc1=O]

69 mg (0.19 mmol) of 2-[4-(5-chloro-2-cyanophenyl)-5-methoxy-2-oxopyridin-1(2H)-yl]butanoic acid (racemate) and 29 mg (0.21 mmol, 1.1 eq.) of [1,2,4]triazolo[4,3-a]pyridine-6-amine were reacted according to General Method 1. After aqueous work-up, the crude product was purified by preparative RP-HPLC (Reprosil C18, water/acetonitrile gradient). Yield: 58 mg (65% of theory)

LC/MS [Method 1]: $R_t$=0.87 min; MS (ESIpos): m/z=463 (M+H)$^+$, $^1$H-NMR (400 MHz, DMSO-d$_6$): δ [ppm]=10.90 (s, 1H), 9.45 (s, 1H), 8.45 (s, 1H), 8.00 (d, 1H), 7.87 (d, 1H), 7.77-7.70 (m, 2H), 7.68 (dd, 1H), 7.52 (s, 1H), 6.56 (s, 1H), 5.64 (dd, 1H), 3.70 (s, 3H), 2.30-2.11 (m, 2H), 0.92 (t, 3H).

Example 21

2-[4-(5-Chloro-2-cyanophenyl)-5-methoxy-2-oxopyridin-1(2H)-yl]-4-methoxy-N-([1,2,4]triazolo[4,3-a]pyridin-6-yl)butanamide (racemate)

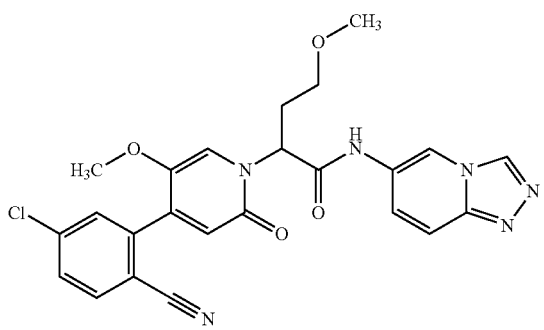 [SMILES: COCCC(C(=O)Nc1ccc2nncn2c1)n1cc(OC)c(-c2cc(Cl)ccc2C#N)cc1=O]

150 mg (0.398 mmol) of 2-[4-(5-chloro-2-cyanophenyl)-5-methoxy-2-oxopyridin-1(2H)-yl]-4-methoxybutanoic acid (racemate) and 59 mg (0.44 mmol, 1.1 eq.) of [1,2,4]triazolo[4,3-a]pyridine-6-amine were reacted according to General Method 1. Yield: 27 mg (14% of theory)

LC/MS [Method 1]: $R_t$=0.84 min; MS (ESIpos): m/z=493 (M+H)$^+$, $^1$H-NMR (400 MHz, DMSO-d$_6$): δ [ppm]=10.8 (s, 1H), 9.44 (d, 1H), 8.45 (s, 1H), 8.02-7.98 (m, 1H), 7.86 (d, 1H), 7.76-7.71 (m, 3H), 7.53 (s, 1H), 6.55 (s, 1H), 5.77 (dd, 1H), 3.70 (s, 3H), 3.43 (dt, 1H), 3.31-3.26 (m, 1H), 3.22 (s, 3H), 2.49-2.36 (m, 2H).

Example 22

2-[4-(5-Chloro-2-cyanophenyl)-5-methoxy-2-oxopyridin-1(2H)-yl]-4-methoxy-N-(3-methyl[1,2,4]triazolo[4,3-a]pyridin-6-yl)butanamide (racemate)

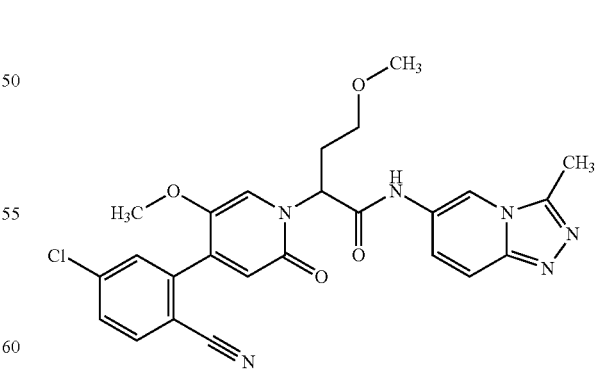

130 mg (0.35 mmol) of 2-[4-(5-chloro-2-cyanophenyl)-5-methoxy-2-oxopyridin-1(2H)-yl]-4-methoxybutanoic acid (racemate) and 76 mg (74% pure, 0.38 mmol, 1.1 eq.) of 3-methyl[1,2,4]triazolo[4,3-a]pyridine-6-amine were reacted according to General Method 1. The crude product was purified by flash chromatography (silica gel 50, dichloromethane/methanol gradient). Yield: 30 mg (purity 90%, 15% of theory)

LC/MS [Method 2]: $R_t$=2.29 min; MS (ESIpos): m/z=507 (M+H)$^+$, $^1$H-NMR (400 MHz, DMSO-d$_6$): δ [ppm]=10.77 (s, 1H), 8.90 (s, 1H), 8.02-7.98 (m, 1H), 7.77-7.70 (m, 3H), 7.51 (s, 1H), 7.38 (dd, 1H), 6.54 (s, 1H), 5.78 (dd, 1H), 3.70 (s, 3H), 3.46-3.39 (m, 1H), 3.30-3.25 (m, 1H), 3.22 (s, 3H), 2.63 (s, 3H), 2.48-2.39 (m, 2H).

Example 23

2-[4-(5-Chloro-2-cyanophenyl)-5-methoxy-2-oxopyridin-1(2H)-yl]-4-methoxy-N-(3-ethyl[1,2,4]triazolo[4,3-a]pyridin-6-yl)butanamide (racemate)

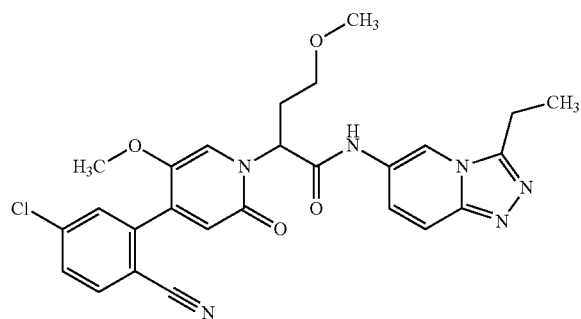 [SMILES: CCc1nnc2ccc(NC(=O)C(CCOC)n3cc(OC)c(-c4cc(Cl)ccc4C#N)cc3=O)cn12]

50 mg (0.13 mmol) of 2-[4-(5-chloro-2-cyanophenyl)-5-methoxy-2-oxopyridin-1(2H)-yl]-4-methoxybutanoic acid (racemate) and 26 mg (0.16 mmol, 1.2 eq.) of 3-ethyl[1,2,4]triazolo[4,3-a]pyridine-6-amine were initially charged in 1.5 ml of dimethylformamide, and 0.11 ml (81 mg, 6.0 eq.) of triethylamine was added. 237 μl (796 μmol, 3.0 eq.) of T3P (50% in ethyl acetate) were then added dropwise. The reaction mixture was left to stir at RT overnight, water and ethyl acetate were then added and the aqueous phase was extracted twice with ethyl acetate. The combined organic phases were washed with saturated aqueous sodium chloride solution, dried over magnesium sulphate and concentrated under reduced pressure. The crude product was purified by flash chromatography (silica gel 50, dichloromethane/methanol gradient). Yield: 64 mg (89% of theory)

LC/MS [Method 1]: $R_t$=0.79 min; MS (ESIpos): m/z=521 (M+H)$^+$, $^1$H-NMR (400 MHz, DMSO-d$_6$): δ [ppm]=10.76 (s, 1H), 8.92 (s, 1H), 8.03-7.97 (m, 1H), 7.78-7.71 (m, 3H), 7.51 (s, 1H), 7.38 (dd, 1H), 6.54 (s, 1H), 5.77 (dd, 1H), 3.70 (s, 3H), 3.46-3.38 (m, 1H), 3.31-3.25 (m, 1H), 3.22 (s, 3H), 3.03 (d, 2H), 2.44 (d, 2H), 1.36 (t, 3H).

Example 24

N-(3-Butyl[1,2,4]triazolo[4,3-a]pyridin-6-yl)-2-[4-(5-chloro-2-cyanophenyl)-5-methoxy-2-oxopyridin-1(2H)-yl]-4-methoxybutanamide (racemate)

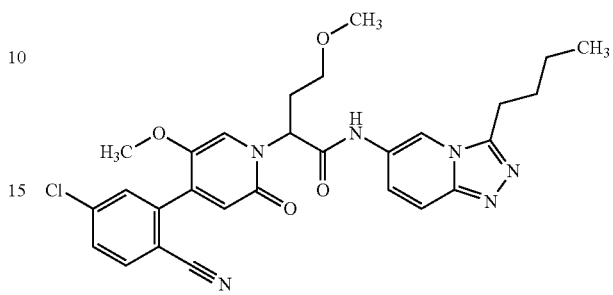

100 mg (0.27 mmol) of 2-[4-(5-chloro-2-cyanophenyl)-5-methoxy-2-oxopyridin-1(2H)-yl]-4-methoxybutanoic acid (racemate) and 71 mg (85% pure, 0.32 mmol, 1.2 eq.) of 3-butyl[1,2,4]triazolo[4,3-a]pyridine-6-amine were initially charged in 3.0 ml of dimethylformamide, and 0.22 ml (161 mg, 6.0 eq.) of triethylamine was added. 474 μl (796 μmol, 3.0 eq.) of T3P (50% in ethyl acetate) were then added dropwise. The reaction mixture was left to stir at RT overnight, water and ethyl acetate were then added and the aqueous phase was extracted twice with ethyl acetate. The combined organic phases were washed with aqueous saturated sodium chloride solution, dried over magnesium sulphate and concentrated under reduced pressure. The crude product was purified by flash chromatography (silica gel 50, dichloromethane/methanol gradient) and subsequent preparative HPLC (Chromatorex 125 mm×30 mm, 10 μm, mobile phase: water/acetonitrile, gradient 10-90% acetonitrile). Yield: 17 mg (12% of theory)

LC/MS [Method 1]: $R_t$=1.01 min; MS (ESIpos): m/z=549 (M+H)$^+$, $^1$H-NMR (400 MHz, DMSO-d$_6$): δ [ppm]=10.77 (s, 1H), 9.31 (dd, 1H), 8.02-7.98 (m, 1H), 7.76-7.70 (m, 3H), 7.66 (dd, 1H), 7.53 (s, 1H), 6.54 (s, 1H), 5.76 (dd, 1H), 3.69 (s, 3H), 3.45-3.38 (m, 1H), 3.28-3.25 (m, 1H), 3.21 (s, 3H), 2.78 (t, 2H), 2.47-2.37 (m, 2H), 1.77-1.68 (m, 2H), 1.36 (sxt, 2H), 0.91 (t, 3H).

Example 25

2-[4-(5-Chloro-2-cyanophenyl)-5-methoxy-2-oxopyridin-1(2H)-yl]-N-{3-[(dimethylamino)-methyl][1,2,4]triazolo[4,3-a]pyridin-6-yl}-4-methoxybutanamide (racemate)

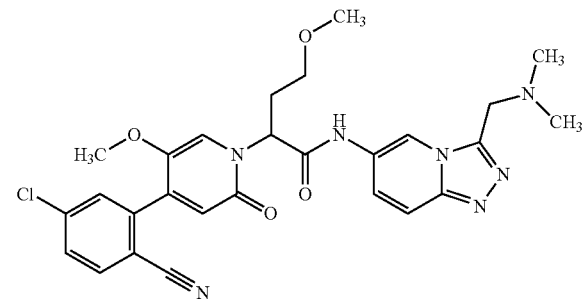 [SMILES: COCCC(C(=O)Nc1ccc2nnc(CN(C)C)n2c1)n1cc(OC)c(-c2cc(Cl)ccc2C#N)cc1=O]

75 mg (0.20 mmol) of 2-[4-(5-chloro-2-cyanophenyl)-5-methoxy-2-oxopyridin-1(2H)-yl]-4-methoxybutanoic acid (racemate) and 46 mg (0.24 mmol, 1.2 eq.) of 3-[(dimethylamino)methyl][1,2,4]triazolo[4,3-a]pyridine-6-amine were reacted according to General Method 1. The crude product was purified by preparative HPLC (Chromatorex 125 mm×30 mm, 10 μm, mobile phase: water/acetonitrile, gradient 10-90% acetonitrile). Yield: 96 mg (87% of theory)

LC/MS [Method 1]: $R_t$=1.01 min; MS (ESIpos): m/z=550 (M+H)$^+$, $^1$H-NMR (400 MHz, DMSO-d$_6$): δ [ppm]=10.91 (s, 1H), 10.22 (br. s, 1H), 9.47 (dd, 1H), 8.02-7.98 (m, 1H), 7.93 (dd, 1H), 7.81 (dd, 1H), 7.73 (s, 2H), 7.51 (s, 1H), 6.55 (s, 1H), 5.74 (dd, 1H), 4.60 (s, 2H), 3.70 (s, 3H), 3.47-3.39 (m, 1H), 3.30-3.26 (m, 1H), 3.22 (s, 3H), 2.88 (s, 6H), 2.48-2.38 (m, 2H).

Example 26

2-[4-(5-Chloro-2-cyanophenyl)-5-methoxy-2-oxopyridin-1(2H)-yl]-4-methoxy-N-[3-(morpholin-4-ylmethyl)[1,2,4]triazolo[4,3-a]pyridin-6-yl]butanamide (racemate)

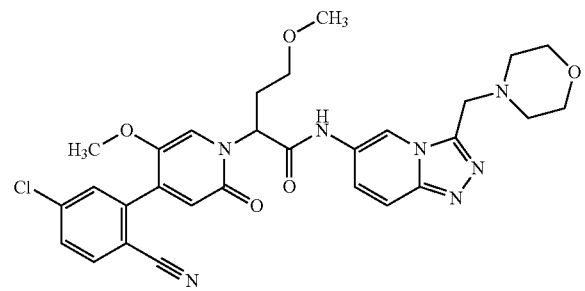 [SMILES: COCCC(C(=O)Nc1ccc2nnc(CN3CCOCC3)n2c1)n1cc(OC)c(-c2cc(Cl)ccc2C#N)cc1=O]

According to General Method 6, 75 mg (0.20 mmol) of 2-[4-(5-chloro-2-cyanophenyl)-5-methoxy-2-oxopyridin-1(2H)-yl]-4-methoxybutanoic acid (racemate) and 91 mg (77% pure, 0.30 mmol, 1.5 eq.) of 3-(morpholin-4-ylmethyl) [1,2,4]triazolo[4,3-a]pyridine-6-amine were initially charged in pyridine at 60° C. and reacted with one another by addition of T3P. The crude product was purified by flash chromatography (silica gel 50, mobile phase: dichloromethane/methanol mixtures). Yield: 31 mg (purity 92%, 24% of theory)

LC/MS [Method 1]: $R_t$=0.68 min; MS (ESIpos): m/z=592 (M+H)$^+$, $^1$H-NMR (400 MHz, DMSO-d$_6$): δ [ppm]=10.81 (s, 1H), 9.37-9.35 (m, 1H), 8.00 (d, 1H), 7.80-7.68 (m, 4H), 7.53 (s, 1H), 6.54 (s, 1H), 5.76 (dd, 1H), 3.76-3.71 (m, 1H), 3.69 (s, 3H), 3.68-3.62 (m, 1H), 3.59-3.53 (m, 4H), 3.45-3.38 (m, 1H), 3.30-3.24 (m, 1H), 3.21 (s, 3H), 2.48-2.35 (m, 2H).

Example 27

2-[5-Chloro-4-(5-chloro-2-cyanophenyl)-2-oxopyridin-1(2H)-yl]-N-(imidazo[1,5-a]pyridin-6-yl)-4-methoxybutanamide (racemate)

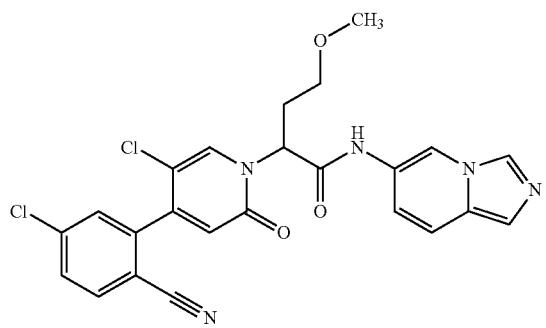 [SMILES: COCCC(C(=O)Nc1ccc2cncn2c1)n1cc(Cl)c(-c2cc(Cl)ccc2C#N)cc1=O]

50 mg (90% pure, 0.12 mmol) of 2-[5-chloro-4-(5-chloro-2-cyanophenyl)-2-oxopyridin-1(2H)-yl]-4-methoxybutanoic acid (racemate) and 33 mg (69% pure, 0.18 mmol, 1.5 eq.) of imidazo[1,5-a]pyridine-6-amine were reacted according to General Method 1. The crude product was purified by preparative HPLC (water/acetonitrile/0.1% formic acid gradient). Yield: 7.9 mg (13% of theory)

LC/MS [Method 1]: $R_t$=0.77 min; MS (ESIpos): m/z=496 (M+H)$^+$, $^1$H-NMR (400 MHz, DMSO-d$_6$): δ [ppm]=10.57 (s, 1H), 9.07 (s, 1H), 8.37 (s, 1H), 8.23 (s, 1H), 8.07 (d, 1H), 7.86-7.76 (m, 2H), 7.55 (d, 1H), 7.32 (s, 1H), 6.83-6.76 (m, 1H), 6.68 (s, 1H), 5.85-5.71 (m, 1H), 3.42 (dt, 2H), 3.30-3.25 (m, 1H), 3.20 (s, 3H), 2.42 (q, 2H).

Example 28

2-[4-(5-Chloro-2-cyanophenyl)-5-methoxy-2-oxopyridin-1(2H)-yl]-N-(imidazo[1,2-a]pyridin-6-yl)-3-(pyridin-2-yl)propanamide (racemate)

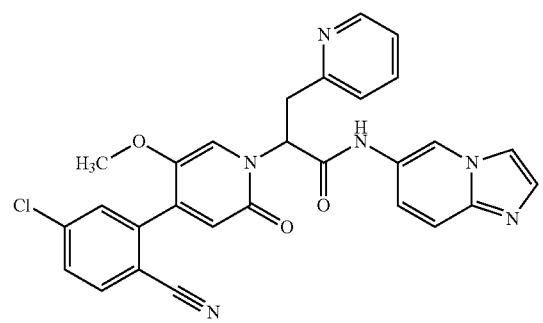 [SMILES: COc1cn(C(Cc2ccccn2)C(=O)Nc2ccc3nccn3c2)c(=O)cc1-c1cc(Cl)ccc1C#N]

30 mg (93% pure, 0.068 mmol) of 2-[4-(5-chloro-2-cyanophenyl)-5-methoxy-2-oxopyridin-1(2H)-yl]-3-(pyridin-2-yl)propanoic acid (racemate) and 15.0 mg (90% pure, 0,102 mmol, 1.5 eq.) of imidazo[1,2-a]pyridine-6-amine were reacted according to General Method 6. The crude product was purified by preparative HPLC (water/acetonitrile/0.1% formic acid gradient). The product was then dissolved in acetonitrile and filtered through a solid phase extraction cartridge (StratoSpheres SPE PL-HCO₃ MP-Resin). The filtrate was lyophilised. Yield: 11 mg (31% of theory)

LC/MS [Method 1]: $R_t$=0.66 min; MS (ESIneg): m/z=523 (M−H)⁻,

¹H-NMR (400 MHz, DMSO-$d_6$): δ [ppm]=10.68 (s, 1H), 9.23 (s, 1H), 8.49 (d, 1H), 8.05-7.92 (m, 2H), 7.76-7.63 (m, 3H), 7.62-7.47 (m, 3H), 7.34 (d, 1H), 7.28-7.17 (m, 2H), 6.43 (s, 1H), 6.16 (t, 1H), 3.69 (d, 2H), 3.64 (s, 3H).

Example 29

2-[4-(5-Chloro-2-cyanophenyl)-5-methoxy-2-oxopyridin-1(2H)-yl]-N-(imidazo[1,2-a]pyridin-6-yl)-3-(1,3-oxazol-5-yl)propanamide (racemate)

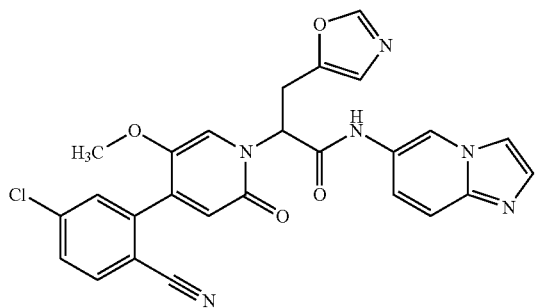 [SMILES: COc1cn(C(Cc2cnco2)C(=O)Nc2ccc3nccn3c2)c(=O)cc1-c1cc(Cl)ccc1C#N]

50 mg (80% pure, 0.10 mmol) of 2-[4-(5-chloro-2-cyanophenyl)-5-methoxy-2-oxopyridin-1(2H)-yl]-3-(1,3-oxazol-5-yl)propanoic acid (racemate) and 26.6 mg (90% pure, 0.18 mmol, 1.8 eq.) of imidazo[1,2-a]pyridine-6-amine were reacted according to General Method 6. The crude product was purified by preparative HPLC (water/acetonitrile/0.1% formic acid gradient). Yield: 35 mg (68% of theory)

LC/MS [Method 8]: $R_t$=0.82 min; MS (ESIpos): m/z=515 (M+H)⁺,

¹H-NMR (400 MHz, DMSO-$d_6$): δ [ppm]=10.66 (s, 1H), 9.32-9.14 (m, 1H), 8.24 (s, 1H), 8.05-7.93 (m, 2H), 7.77-7.65 (m, 2H), 7.64-7.50 (m, 3H), 7.23 (dd, 1H), 6.92 (s, 1H), 6.51 (s, 1H), 5.99 (dd, 1H), 3.82-3.70 (m, 1H), 3.70-3.59 (m, 4H).

Example 30

2-[5-Chloro-4-(5-chloro-2-cyanophenyl)-2-oxopyridin-1(2H)-yl]-N-(imidazo[1,2-a]pyridin-6-yl)-3-(1,3-oxazol-5-yl)propanamide (racemate)

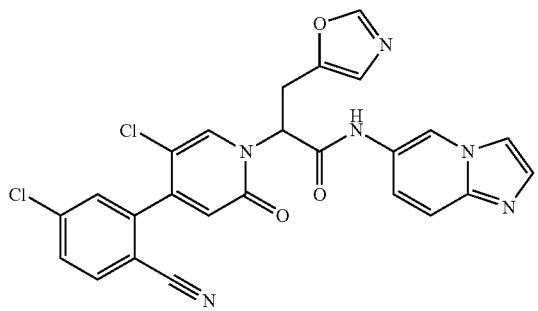 [SMILES: N#Cc1ccc(Cl)cc1-c1cc(=O)n(C(Cc2cnco2)C(=O)Nc2ccc3nccn3c2)cc1Cl]

50 mg (85% pure, 0,105 mmol) of 2-[5-chloro-4-(5-chloro-2-cyanophenyl)-2-oxopyridin-1(2H)-yl]-3-(1,3-oxazol-5-yl)propanoic acid (racemate) and 26.5 mg (90% pure, 0,179 mmol, 1.7 eq.) of imidazo[1,2-a]pyridine-6-amine were reacted according to General Method 6. The crude product was purified by preparative HPLC (water/acetonitrile/0.1% formic acid gradient). Yield: 21 mg (purity 83%, 32% of theory)

LC/MS [Method 2]: $R_t$=1.87 min; MS (ESIpos): m/z=519 (M+H)⁺,

¹H-NMR (400 MHz, DMSO-$d_6$): δ [ppm]=10.73 (s, 1H), 9.22 (s, 1H), 8.35 (s, 1H), 8.25 (s, 1H), 8.08-8.03 (m, 1H), 8.00 (s, 1H), 7.82-7.75 (m, 2H), 7.59-7.53 (m, 2H), 7.24-7.15 (m, 1H), 6.92 (s, 1H), 6.66 (s, 1H), 5.98 (dd, 1H), 3.78 (dd, 1H), 3.66 (dd, 1H).

Example 31

2-[4-(5-Chloro-2-cyanophenyl)-5-(difluoromethoxy)-2-oxopyridin-1(2H)-yl]-N-(imidazo[1,2-a]pyridin-6-yl)-3-(1,3-oxazol-5-yl)propanamide (racemate)

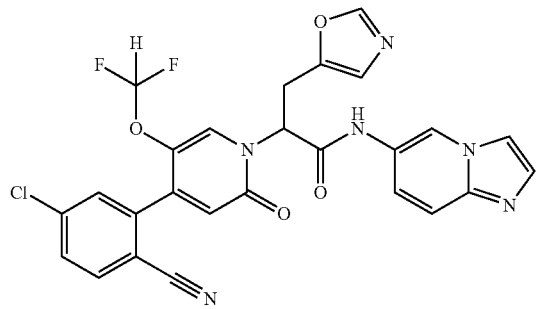 [SMILES: N#Cc1ccc(Cl)cc1-c1cc(=O)n(C(Cc2cnco2)C(=O)Nc2ccc3nccn3c2)cc1OC(F)F]

40 mg (0.092 mmol) of 2-[4-(5-chloro-2-cyanophenyl)-5-(difluoromethoxy)-2-oxopyridin-1(2H)-yl]-3-(1,3-oxazol-5-yl)propanoic acid (racemate) and 20.4 mg (90% pure, 0,138 mmol, 1.5 eq.) of imidazo[1,2-a]pyridine-6-amine were reacted according to General Method 6. The crude product was purified by preparative HPLC (water/acetonitrile/0.1% formic acid gradient). Yield: 20 mg (40% of theory)

LC/MS [Method 1]: $R_t$=0.67 min; MS (ESIpos): m/z=551 (M+H)⁺,

¹H-NMR (400 MHz, DMSO-$d_6$): δ [ppm]=10.79 (s, 1H), 9.24 (s, 1H), 8.25 (s, 1H), 8.19-8.11 (m, 1H), 8.09-7.99 (m, 2H), 7.81-7.71 (m, 2H), 7.65-7.54 (m, 2H), 7.30-7.20 (m, 1H), 6.92 (s, 1H), 6.84 (t, 1H), 6.63 (s, 1H), 5.99 (dd, 1H), 3.73 (dd, 1H), 3.64 (dd, 1H).

Example 32

2-[4-(5-Chloro-2-cyanophenyl)-5-methoxy-2-oxopyridin-1(2H)-yl]-N-(imidazo[1,2-a]pyridin-6-yl)-3-(1,3-oxazol-4-yl)propanamide (racemate)

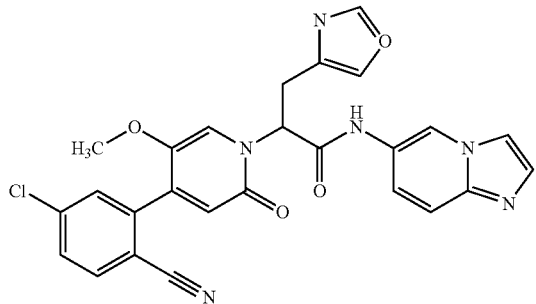

40 mg (0.1 mmol) of 2-[4-(5-chloro-2-cyanophenyl)-5-methoxy-2-oxopyridin-1(2H)-yl]-3-(1,3-oxazol-4-yl)propanoic acid (racemate) and 19.7 mg (0.15 mmol, 1.5 eq.) of imidazo[1,2-a]pyridine-6-amine were reacted according to General Method 6. The crude product was purified by preparative HPLC (water/acetonitrile/0.1% formic acid gradient). Yield: 43.8 mg (84% of theory)

LC/MS [Method 1]: $R_t$=0.65 min; MS (ESIpos): m/z=515 (M+H)$^+$, $^1$H-NMR (400 MHz, DMSO-d$_6$): δ [ppm]=10.69 (s, 1H), 9.25 (s, 1H), 8.30 (s, 1H), 8.06-7.91 (m, 2H), 7.82 (s, 1H), 7.76-7.65 (m, 2H), 7.63-7.50 (m, 3H), 7.27 (dd, 1H), 6.48 (s, 1H), 6.00 (dd, 1H), 3.68 (s, 3H), 3.54 (dd, 1H), 3.42 (dd, 1H).

Example 33

2-[5-Chloro-4-(5-chloro-2-cyanophenyl)-2-oxopyridin-1(2H)-yl]-N-(imidazo[1,2-a]pyridin-6-yl)-3-(1,3-oxazol-4-yl)propanamide (racemate)

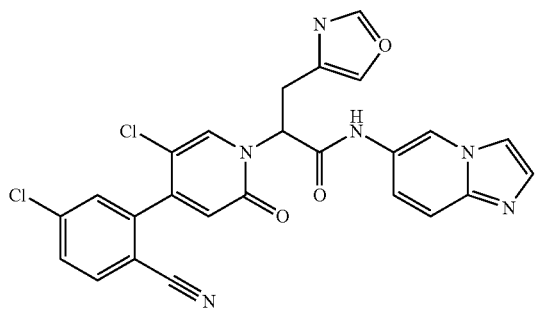

40 mg (0.1 mmol) of 2-[5-chloro-4-(5-chloro-2-cyanophenyl)-2-oxopyridin-1(2H)-yl]-3-(1,3-oxazol-4-yl)propanoic acid (racemate) and 19.8 mg (0.15 mmol, 1.5 eq.) of imidazo[1,2-a]pyridine-6-amine were reacted according to General Method 6. The crude product was purified by preparative HPLC (water/acetonitrile/0.1% formic acid gradient). Yield: 41 mg (79% of theory)

LC/MS [Method 1]: $R_t$=0.70 min; MS (ESIpos): m/z=519 (M+H)$^+$, $^1$H-NMR (400 MHz, DMSO-d$_6$): δ [ppm]=10.78 (s, 1H), 9.25 (s, 1H), 8.35-8.19 (m, 2H), 8.10-7.94 (m, 2H), 7.89-7.67 (m, 3H), 7.66-7.47 (m, 2H), 7.26 (d, 1H), 6.62 (s, 1H), 5.99 (dd, 1H), 3.57 (dd, 1H), 3.42 (dd, 1H).

Example 34

2-[4-(5-Chloro-2-cyanophenyl)-5-methoxy-2-oxopyridin-1(2H)-yl]-N-(pyrazolo[1,5-a]pyridin-5-yl)butanamide (racemate)

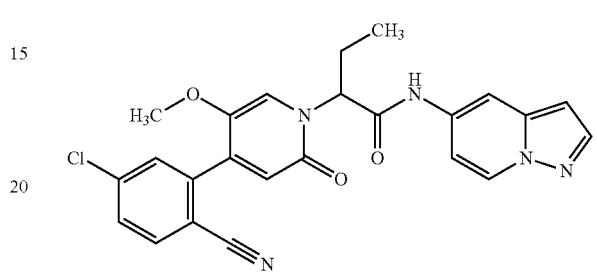

138 mg (0.39 mmol) of 2-[4-(5-chloro-2-cyanophenyl)-5-methoxy-2-oxopyridin-1(2H)-yl]butanoic acid (racemate) and 47 mg (0.35 mmol) of pyrazolo[1,5-a]pyridine-5-amine [B. C. Baguley et al. *Bioorganic and Medicinal Chemistry*, 2012, 20, 69-85] were reacted according to General Method 5. After aqueous work-up, the crude product was purified by flash chromatography (silica gel 50, cyclohexane/ethyl acetate gradient). Yield: 82 mg (51% of theory)

LC/MS [Method 1]: $R_t$=0.97 min; MS (ESIpos): m/z=462 (M+H)$^+$, $^1$H-NMR (400 MHz, DMSO-d$_6$): δ [ppm]=10.75 (s, 1H), 8.62 (d, 1H), 8.14 (d, 1H), 8.00 (d, 1H), 7.92 (d, 1H), 7.70-7.70 (m, 2H), 7.51 (s, 1H), 6.97 (dd, 1H), 6.55 (s, 1H), 6.50 (d, 1H), 5.64 (dd, 1H), 3.70 (s, 3H), 2.27-2.09 (m, 2H), 0.92 (t, 3H).

Example 35

2-[4-(5-Chloro-2-cyanophenyl)-5-methoxy-2-oxopyridin-1(2H)-yl]-4-methoxy-N-(pyrazolo[1,5-a]pyridin-5-yl)butanamide (racemate)

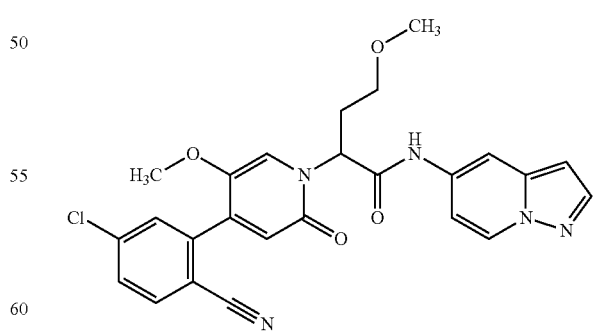

800 mg (2.12 mmol) of 2-[4-(5-chloro-2-cyanophenyl)-5-methoxy-2-oxopyridin-1(2H)-yl]-4-methoxybutanoic acid (racemate) and 424 mg (3.19 mmol, 1.5 eq.) of pyrazolo[1,5-a]pyridine-5-amine were reacted according to General Method 1. The crude product was purified by flash chromatography (silica gel 50, dichloromethane/methanol gradient), and the product was stirred with acetonitrile and filtered off with suction. Yield: 550 mg (53% of theory)

LC/MS [Method 1]: R$_t$=0.94 min; MS (ESIpos): m/z=492 (M+H)$^+$, $^1$H-NMR (400 MHz, DMSO-d$_6$): δ [ppm]=10.70 (s, 1H), 8.61 (d, 1H), 8.14 (d, 1H), 8.02-7.98 (m, 1H), 7.92 (d, 1H), 7.76-7.72 (m, 2H), 7.53 (s, 1H), 7.00 (dd, 1H), 6.54 (s, 1H), 6.50 (dd, 1H), 5.77 (dd, 1H), 3.69 (s, 3H), 3.45-3.38 (m, 1H), 3.31-3.25 (m, 1H), 3.21 (s, 3H), 2.48-2.36 (m, 2H).

Example 36

2-[4-(5-Chloro-2-cyanophenyl)-5-methoxy-2-oxopyridin-1(2H)-yl]-4-methoxy-N-(pyrazolo[1,5-a]pyridin-5-yl)butanamide (enantiomer 1)

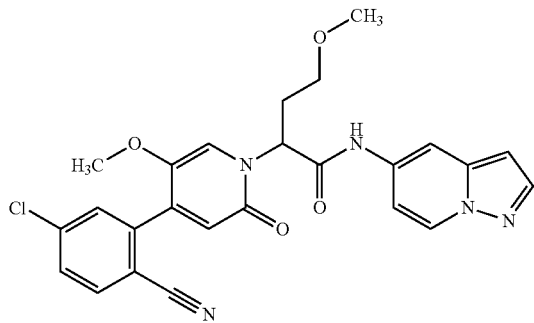 [SMILES: COCCC(C(=O)Nc1ccn2nccc2c1)n1cc(OC)c(-c2cc(Cl)ccc2C#N)cc1=O]

Enantiomer separation of 45.3 mg of the racemate from Example 35 gave 12.3 mg of the title compound Example 36 (enantiomer 1) in addition to 14.4 mg of enantiomer 2.

Chiral HPLC: enantiomer 1: R$_t$=2.75 min; 100% ee [comparison: enantiomer 2: R$_t$=1.71 min; 100% ee]

Separating method: Column: Daicel IF 5 μm 250 mm×20 mm; mobile phase: 40% isohexane, 60% ethanol; temperature: 23° C.; flow rate: 20 ml/min; UV detection: 220 nm.

Analysis: Column: Daicel Chiralpak IF 3 μm 50 mm×4.6 mm, mobile phase: 50% isohexane, 50% ethanol; flow rate: 1 ml/min; UV detection: 220 nm.

$^1$H-NMR (400 MHz, DMSO-d$_6$): δ [ppm]=10.70 (s, 1H), 8.61 (d, 1H), 8.14 (d, 1H), 8.02-7.87 (m, 1H), 7.92 (d, 1H), 7.76-7.72 (m, 2H), 7.53 (s, 1H), 7.00 (dd, 1H), 6.54 (s, 1H), 6.51-6.49 (m, 1H), 5.77 (dd, 1H), 3.69 (s, 3H), 3.45-3.38 (m, 1H), 3.31-3.25 (m, 1H), 3.21 (s, 3H), 2.48-2.36 (m, 2H).

Example 37

2-[5-Chloro-4-(5-chloro-2-cyanophenyl)-2-oxopyridin-1(2H)-yl]-4-methoxy-N-(pyrazolo[1,5-a]pyridin-5-yl)butanamide (racemate)

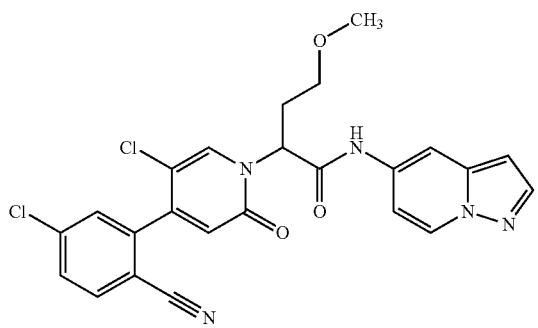 [SMILES: COCCC(C(=O)Nc1ccn2nccc2c1)n1cc(Cl)c(-c2cc(Cl)ccc2C#N)cc1=O]

110 mg (0.26 mmol) of 2-[5-chloro-4-(5-chloro-2-cyanophenyl)-2-oxopyridin-1(2H)-yl]-4-methoxybutanoic acid (racemate) and 51 mg (0.39 mmol, 1.5 eq.) of pyrazolo[1,5-a]pyridine-5-amine were reacted according to General Method 6. The crude product was purified by preparative HPLC (water/acetonitrile/0.1% formic acid gradient). Yield: 95 mg (74% of theory)

LC/MS [Method 1]: R$_t$=1.00 min; MS (ESIpos): m/z=496 (M+H)$^+$, $^1$H-NMR (400 MHz, DMSO-d$_6$): δ [ppm]=10.76 (br. s, 1H), 8.62 (d, 1H), 8.23 (s, 1H), 8.11 (d, 1H), 8.07 (d, 1H), 7.92 (d, 1H), 7.84-7.76 (m, 2H), 6.98 (dd, 1H), 6.68 (s, 1H), 6.50 (d, 1H), 5.85-5.67 (m, 1H), 3.42 (dt, 1H), 3.27 (dt, 1H), 3.20 (s, 3H), 2.47-2.38 (m, 2H).

Example 38

2-[5-Chloro-4-(5-chloro-2-cyanophenyl)-2-oxopyridin-1(2H)-yl]-4-methoxy-N-(pyrazolo[1,5-a]pyridin-5-yl)butanamide (enantiomer 1)

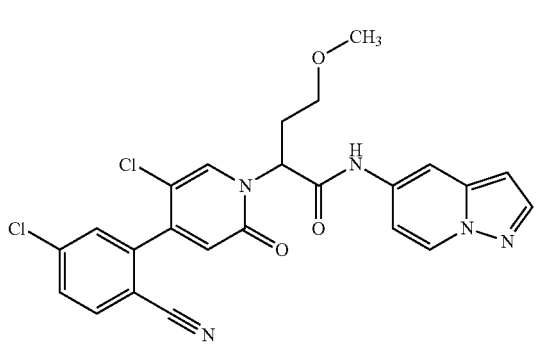 [SMILES: COCCC(C(=O)Nc1ccn2nccc2c1)n1cc(Cl)c(-c2cc(Cl)ccc2C#N)cc1=O]

Enantiomer separation of 90 mg of the racemate from Example 37 gave 34 mg of the title compound Example 38 (enantiomer 1) in addition to 33 mg of enantiomer 2.

Chiral HPLC: enantiomer 1: R$_t$=7.88 min; 100% ee [comparison: enantiomer 2: R$_t$=4.37 min; 100% ee]

Separation method (SFC): Column: Daicel Chiralpak AZ-H 5 μm 250 mm×20 mm; mobile phase: 70% carbon dioxide, 30% 2-propanol; temperature: 40° C.; flow rate: 80 ml/min; UV detection: 210

Analysis (SFC): Column: Daicel Chiralpak AZ-H 250 mm×4.6 mm; mobile phase: 60% carbon dioxide, 40% 2-propanol; flow rate: 3 ml/min, temperature: 30° C.; UV detection: 210 nm.

Example 39

4-(5-Chloro-2-cyanophenyl)-6-oxo-1-[1-oxo-1-(pyrazol[1,5-a]pyridin-5-ylamino)butan-2-yl]-1,6-dihydropyridine-3-carboxylic acid (racemate)

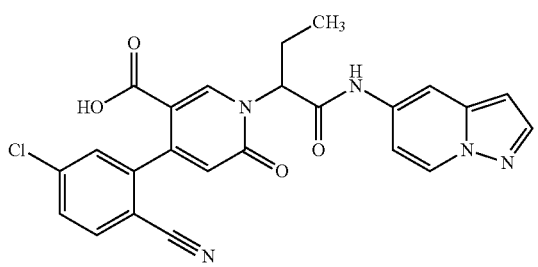 [SMILES: CCC(C(=O)Nc1ccn2nccc2c1)n1cc(C(=O)O)c(-c2cc(Cl)ccc2C#N)cc1=O]

147 mg (260 µmol) of benzyl 4-(5-chloro-2-cyanophenyl)-6-oxo-1-[1-oxo-1-(pyrazol[1,5-a]pyridin-5-ylamino)butan-2-yl]-1,6-dihydropyridine-3-carboxylate (racemate) were initially charged in 3 ml of tetrahydrofuran, and 14 mg (13 µmol) of palladium (10% on carbon) were added. The reaction mixture was hydrogenated at standard pressure for 3 h. The reaction mixture was then filtered off and the solvent was removed under reduced pressure. The residue was purified by preparative HPLC [column: Chromatorex C18, 10 µm, 125 mm×30 mm, mobile phase: acetonitrile/0.05%-formic acid gradient (0 to 3 min 10% acetonitrile, to 35 min 90% acetonitrile and for a further 3 min 90% acetonitrile)], giving the title compound. Yield: 36 mg (29% of theory)

LC/MS [Method 1]: $R_t$=0.81 min; MS (ESIpos): m/z=476 (M+H)$^+$, $^1$H-NMR (400 MHz, DMSO-d$_6$): δ [ppm]=12.9 (br. s, 1H), 10.9 (s, 1H), 8.62 (d, 1H), 8.59 (s, 1H), 8.12 (s, 1H), 7.95-7.90 (m, 2H), 7.69-7.64 (m, 2H), 6.95 (dd, 1H), 6.50 (d, 1H), 6.47 (s, 1H), 5.64 (dd, 1H), 2.29-2.19 (m, 1H), 2.14-2.01 (m, 1H), 0.94 (t, 3H).

Example 40

2-[4-(5-Chloro-2-cyanophenyl)-5-methoxy-2-oxopyridin-1(2H)-yl]-N-(3-chloropyrazolo[1,5-a]pyridin-5-yl)butanamide (racemate)

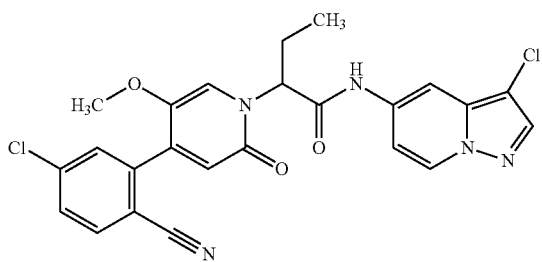 [SMILES: CCC(C(=O)Nc1ccn2ncc(Cl)c2c1)n1cc(OC)c(-c2cc(Cl)ccc2C#N)cc1=O]

At RT, 30 mg (0.22 mmol, 1.45 eq.) in total of N-chlorosuccinimide were added to a solution of 71 mg (0.15 mmol) of 2-[4-(5-chloro-2-cyanophenyl)-5-methoxy-2-oxopyridin-1(2H)-yl]-N-(pyrazolo[1,5-a]pyridin-5-yl)butanamide (racemate) in 2 ml of ethanol, and the mixture was stirred at RT overnight. The reaction mixture was concentrated under reduced pressure. After addition of water/ethyl acetate and phase separation, the aqueous phase was extracted with ethyl acetate. The combined organic phases were washed with saturated aqueous sodium chloride solution, dried (sodium sulphate), filtered, concentrated under reduced pressure and dried. Yield: 80 mg (quant.)

LC/MS [Method 1]: $R_t$=1.12 min; MS (ESIpos): m/z=496 (M+H)$^+$, $^1$H-NMR (400 MHz, DMSO-d$_6$): δ [ppm]=10.91 (s, 1H), 8.66 (d, 1H), 8.14 (d, 1H), 8.09 (s, 1H), 8.00 (d, 1H), 7.77-7.71 (m, 2H), 7.50 (s, 1H), 7.01 (dd, 1H), 6.56 (s, 1H), 5.62 (dd, 1H), 3.71 (s, 3H), 2.29-2.12 (m, 2H), 0.92 (t, 3H).

Example 41

2-[4-(5-Chloro-2-cyanophenyl)-5-methoxy-2-oxopyridin-1(2H)-yl]-N-(3-chloropyrazolo[1,5-a]pyridin-5-yl)-4-methoxybutanamide (racemate)

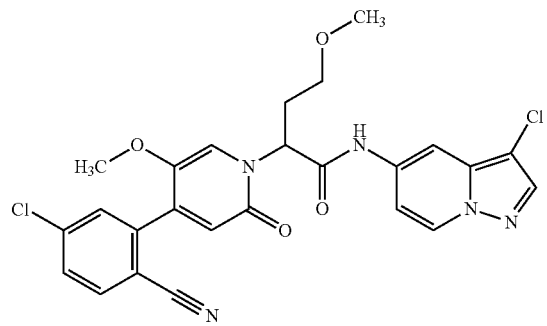 [SMILES: COCCC(C(=O)Nc1ccn2ncc(Cl)c2c1)n1cc(OC)c(-c2cc(Cl)ccc2C#N)cc1=O]

100 mg (90% pure, 0.18 mmol) of 2-[4-(5-chloro-2-cyanophenyl)-5-methoxy-2-oxopyridin-1(2H)-yl]-4-methoxy-N-(pyrazolo[1,5-a]pyridin-5-yl)butanamide (racemate) were dissolved in 3.0 ml of ethanol, 29 mg (0.20 mmol, 1.1 eq.) of N-chlorosuccinimide were added and the mixture was left to stir at RT overnight. A drop of dimethylformamide and a further 4.9 mg (37 µmol, 0.2 eq.) of N-chlorosuccinimide were then added, and the mixture was left to stir for a further 4 h. The reaction solution was then purified by preparative HPLC (Chromatorex 125 mm×30 mm, 10 µm, mobile phase: water/acetonitrile, gradient 10% acetonitrile to 90% acetonitrile). Yield: 16 mg (17% of theory)

LC/MS [Method 1]: $R_t$=1.02 min; MS (ESIpos): m/z=526/528 (M+H)$^+$, $^1$H-NMR (400 MHz, DMSO-d$_6$): δ [ppm]=10.85 (s, 1H), 8.66 (dd, 1H), 8.14 (d, 1H), 8.09 (s, 1H), 8.02-7.99 (m, 1H), 7.76-7.72 (m, 2H), 7.52 (s, 1H), 7.05 (dd, 1H), 6.54 (s, 1H), 5.75 (dd, 1H), 3.70 (s, 3H), 3.46-3.38 (m, 1H), 3.30-3.25 (m, 1H), 3.21 (s, 3H), 2.48-2.40 (m, 2H).

B) Assessment of Physiological efficacy

The suitability of the compounds according to the invention for treating thromboembolic disorders can be demonstrated in the following assay systems:
a) Test Descriptions (In Vitro)
a.1) Measurement of FXIa Inhibition The factor XIa inhibition of the substances according to the invention is determined using a biochemical test system which utilizes the reaction of a peptidic factor XIa substrate to determine the enzymatic activity of human factor XIa. Here, factor XIa cleaves from the peptic factor XIa substrate the C-terminal aminomethylcoumarin (AMC), the fluorescence of which is measured. The determinations are carried out in microtitre plates.

Test substances are dissolved in dimethyl sulphoxide and serially diluted in dimethyl sulphoxide (3000 µM to 0.0078 µM; resulting final concentrations in the test: 50 µM to 0.00013 µM). In each case 1 µl of the diluted substance solutions is placed into the wells of white microtitre plates from Greiner (384 wells). 20 µl of assay buffer (50 mM of Tris/HCl pH 7.4; 100 mM of sodium chloride; 5 mM of calcium chloride; 0.1% of bovine serum albumin) and 20 µl of factor XIa from Kordia (0.45 nM in assay buffer) are then added successively. After 15 min of incubation, the enzyme reaction is started by addition of 20 µl of the factor XIa substrate Boc-Glu(OBzl)-Ala-Arg-AMC dissolved in assay buffer (10 μM in assay buffer) from Bachem, the mixture is incubated at room temperature (22° C.) for 30 min and fluorescence is then measured (excitation: 360 nm, emission: 460 nm). The measured emissions of the test batches with test substance are compared to those of control batches without test substance (only dimethyl sulphoxide instead of test substance in dimethyl sulphoxide), and $IC_{50}$ values are calculated from the concentration/activity relationships. Activity data from this test are listed in Table A below:

TABLE A

| Example No. | $IC_{50}$ [nM] | Example No. | $IC_{50}$ [nM] |
|---|---|---|---|
| 1 | 32 | 2 | 2.3 |
| 3 | 6.6 | 4 | 65 |
| 5 | 1.0 | 6 | 11 |
| 7 | 12 | 8 | 380 |
| 9 | 0.5 | 10 | 36 |
| 11 | 20 | 12 | 3.1 |
| 13 | 16 | 14 | 31 |
| 15 | 41 | 16 | 11 |
| 17 | 65 | 18 | 220 |
| 19 | 33 | 20 | 86 |
| 21 | 21 | 22 | 28 |
| 23 | 53 | 24 | 63 |
| 25 | 20 | 26 | 24 |
| 27 | 96 | 28 | 12 |
| 29 | 16 | 30 | 96 |
| 31 | 500 | 32 | 92 |
| 33 | 310 | 34 | 21 |
| 35 | 4.0 | 36 | 3.6 |
| 37 | 29 | 38 | 15 |
| 39 | 180 | 40 | 140 |
| 41 | 26 | | | a.2) Determination of the Selectivity

To demonstrate the selectivity of the substances with respect to FXIa inhibition, the test substances are examined for their inhibition of other human serin proteases, such as factor Xa, trypsin and plasmin. To determine the enzymatic activity of factor Xa (1.3 nmol/l from Kordia), trypsin (83 mU/ml from Sigma) and plasmin (0.1 μg/ml from Kordia), these enzymes are dissolved (50 mmol/l of Tris buffer [C,C,C-tris(hydroxymethyl)aminomethane], 100 mmol/l of NaCl, 0.1% BSA [bovine serum albumin], 5 mmol/l of calcium chloride, pH 7.4) and incubated for 15 min with test substance in various concentrations in dimethyl sulphoxide and also with dimethyl sulphoxide without test substance. The enzymatic reaction is then started by addition of the appropriate substrates (5 μmol/l of Boc-Ile-Glu-Gly-Arg-AMC from Bachem for factor Xa and trypsin, 5 50 μmol/l of MeOSuc-Ala-Phe-Lys-AMC from Bachem for plasmin). After an incubation time of 30 min at 22° C., fluorescence is measured (excitation: 360 nm, emission: 460 nm). The measured emissions of the test mixtures with test substance are compared to the control mixtures without test substance (only dimethyl sulphoxide instead of test substance in dimethyl sulphoxide) and $IC_{50}$ values are calculated from the concentration/activity relationships.

a.3) Thrombin Generation Assay (Thrombogram)

The effect of the test substances on the thrombogram (thrombin generation assay according to Hemker) is determined in vitro in human plasma (Octaplas® from Octapharma).

In the thrombin generation assay according to Hemker, the activity of thrombin in coagulating plasma is determined by measuring the fluorescent cleavage products of the substrate 1-1140 (Z-Gly-Gly-Arg-AMC, Bachem). The reactions are carried out in the presence of varying concentrations of test substance or the corresponding solvent. To start the reaction, reagents from Thrombinoscope (30 pM or 0.1 pM recombinant tissue factor, 24 μM phospholipids in HEPES) are used. In addition, a thrombin calibrator from Thrombinoscope is used whose amidolytic activity is required for calculating the thrombin activity in a sample containing an unknown amount of thrombin. The test is carried out according to the manufacturer's instructions (Thrombinoscope BV): 4 μl of test substance or of the solvent, 76 μl of plasma and 20 μl of PPP reagent or thrombin calibrator are incubated at 37° C. for 5 min After addition of 20 μl of 2.5 mM thrombin substrate in 20 mM HEPES, 60 mg/ml of BSA, 102 mM of calcium chloride, the thrombin generation is measured every 20 s over a period of 120 min. Measurement is carried out using a fluorometer (Fluoroskan Ascent) from Thermo Electron fitted with a 390/460 nm filter pair and a dispenser.

Using the Thrombinoscope software, the thrombogram is calculated and represented graphically. The following parameters are calculated: lag time, time to peak, peak, ETP (endogenous thrombin potential) and start tail.

a.4) Determination of Anticoagulatory Activity

The anticoagulatory activity of the test substances is determined in vitro in human plasma and rat plasma. To this end, blood is drawn off in a mixing ratio of sodium citrate/blood of 1:9 using a 0.11 molar sodium citrate solution as receiver Immediately after the blood has been drawn off, it is mixed thoroughly and centrifuged at about 4000 g for 15 minutes. The supernatant is pipetted off.

The prothrombin time (PT, synonyms: thromboplastin time, quick test) is determined in the presence of varying concentrations of test substance or the corresponding solvent using a commercial test kit (Neoplastin® from Boehringer Mannheim or Hemoliance® RecombiPlastin from Instrumentation Laboratory). The test compounds are incubated with the plasma at 37° C. for 3 minutes. Coagulation is then started by addition of thromboplastin, and the time when coagulation occurs is determined. The concentration of test substance which effects a doubling of the prothrombin time is determined.

The activated partial thromboplastin time (APTT) is determined in the presence of varying concentrations of test substance or the corresponding solvent using a commercial test kit (PTT reagent from Roche). The test compounds are incubated with the plasma and the PTT reagent (cephalin, kaolin) at 37° C. for 3 minutes. Coagulation is then started by addition of 25 mM calcium chloride, and the time when coagulation occurs is determined. The concentration of test substance which effects an extension by 50% or a doubling of the APTT is determined.

a.5) Determination of the Plasma Kallikrein Activity

To determine the plasma kallikrein inhibition of the substances according to the invention, a biochemical test system is used which utilizes the reaction of a peptidic plasma kallikrein substrate to determine the enzymatic activity of human plasma kallikrein. Here, plasma kallikrein cleaves from the peptic plasma kallikrein substrate the C-terminal aminomethylcoumarin (AMC), the fluorescence of which is measured. The determinations are carried out in microtitre plates.

Test substances are dissolved in dimethyl sulphoxide and serially diluted in dimethyl sulphoxide (3000 μM to 0.0078 μM; resulting final concentrations in the test: 50 μM to 0.00013 μM). In each case 1 μl of the diluted substance solutions is placed into the wells of white microtitre plates from Greiner (384 wells). 20 μl of assay buffer (50 mM Tris/HCl pH 7.4; 100 mM sodium chloride solution; 5 mM of calcium chloride solution; 0.1% of bovine serum albumin) and 20 µl of plasma kallikrein from Kordia (0.6 nM in assay buffer) are then added successively. After 15 min of incubation, the enzyme reaction is started by addition of 20 µl of the substrate H-Pro-Phe-Arg-AMC dissolved in assay buffer (10 µM in assay buffer) from Bachem, the mixture is incubated at room temperature (22° C.) for 30 min and fluorescence is then measured (excitation: 360 nm, emission: 460 nm). The measured emissions of the test batches with test substance are compared to those of control batches without test substance (only dimethyl sulphoxide instead of test substance in dimethyl sulphoxide), and $IC_{50}$ values are calculated from the concentration/activity relationships.

TABLE B

| Example No. | $IC_{50}$ [nM] | Example No. | $IC_{50}$ [nM] |
|---|---|---|---|
| 1 | 140 | 2 | 16 |
| 3 | 13 | 4 | 44 |
| 5 | 7.1 | 6 | 61 |
| 7 | 150 | 9 | 4.8 |
| 10 | 7.0 | 11 | 5.0 |
| 12 | 4.9 | 13 | 13 |
| 14 | 65 | 15 | 31 |
| 16 | 17 | 17 | 24 |
| 18 | 130 | 19 | 25 |
| 20 | 23 | 21 | 8.0 |
| 22 | 8.3 | 23 | 13 |
| 24 | 16 | 25 | 23 |
| 26 | 12 | 27 | 50 |
| 28 | 8.8 | 29 | 11 |
| 30 | 120 | 31 | 970 |
| 32 | 36 | 33 | 250 |
| 34 | 17 | 35 | 4.3 |
| 36 | 3.2 | 37 | 65 |
| 38 | 29 | 39 | 1800 |
| 40 | 51 | 41 | 11 | a.6) Determination of Endothelium Integrity

The activity of the compounds according to the invention is characterized by means of an in vitro permeability assay on "human umbilical venous cells" (HUVEC). Using the EOS apparatus (EC IS: Electric Cell-substrate Impedance Sensing; Applied Biophysics Inc; Troy, N.Y.), it is possible to measure continuously variations in the transendothelial electrical resistance (TEER) across an endothelial cell monolayer plated over gold electrodes. HUVECs are sown on a 96-well sensor electrode plate (96W1 E, Ibidi GmbH, Martinsried, Germany). Hyperpermeability of the confluent cell monolayer formed is induced by stimulation with kininogen, prekallikrein and factor XII (100 nM each). The compounds according to the invention are added prior to the addition of the substances indicated above. The customary concentrations of the compounds are $1\times10^{-10}$ to $1\times10^{-6}$ M.

a.7) Determination of the In Vitro Permeability of Endothelial Cells

In a further hyperpermeability model, the activity of the substances on the modulation of macromolecular permeability is determined HUVECs are sown on a fibronectin-coated Transwell filter membrane (24-well plates, 6.5 mm insert with 0.4 µM polycarbonate membran; Costar #3413). The filter membrane separates the upper from the lower cell culture space, with the confluent endothelial cell layer on the floor of the upper cell culture space. 250 g/ml of 40 kDa FITC dextan (Invitrogen, D1844) are added to the medium of the upper chamber. Hyperpermeability of the monolayer is induced by stimulation with kininogen, prekallikrein and factor XII (100 nM each). Every 30 min, medium samples are removed from the lower chamber and relative fluorescence as a parameter for changes in macromolecular permeability as a function of time is determined using a fluorimeter. The compounds according to the invention are added prior to the addition of the substances indicated above. The customary concentrations of the compounds are $1\times10^{-10}$ to $1\times10^{-6}$ M.

b) Determination of Antithrombotic Activity (In Vivo)

b.1) Arterial Thrombosis Model (Iron(II) Chloride-Induced Thrombosis) in Combination with Ear Bleeding Time in Rabbits The antithrombotic activity of the FXIa inhibitors is tested in an arterial thrombosis model. Thrombus formation is triggered here by causing chemical injury to a region in the carotid artery in rabbits. Simultaneously, the ear bleeding time is determined Male rabbits (Crl:KBL (NZW)BR, Charles River) receiving a normal diet and having a body weight of 2.2-2.5 kg are anaesthetized by intramuscular administration of xylazine and ketamine (Rompun, Bayer, 5 mg/kg and Ketavet, Pharmacia & Upjohn GmbH, 40 mg/kg body weight). Anaesthesia is furthermore maintained by intravenous administration of the same preparations (bolus: continuous infusion) via the right auricular vein.

The right carotid artery is exposed and the vessel injury is then caused by wrapping a piece of filter paper (10 mm×10 mm) on a Parafilm® strip (25 mm×12 mm) around the carotid artery without disturbing the blood flow. The filter paper contains 100 µL of a 13% strength solution of iron(II) chloride (Sigma) in water. After 5 min, the filter paper is removed and the vessel is rinsed twice with aqueous 0.9% strength sodium chloride solution. 30 min after the injury the injured region of the carotid artery is extracted surgically and any thrombotic material is removed and weighed.

The test substances are administered either intravenously to the anaesthetized animals via the femoral vein or orally to the awake animals via gavage, in each case 5 min and 2 h, respectively, before the injury.

Ear bleeding time is determined 2 min after injury to the carotid artery. To this end, the left ear is shaved and a defined 3-mm-long incision (blade Art. Number 10-150-10, Martin, Tuttlingen, Germany) is made parallel to the longitudinal axis of the ear. Care is taken here not to damage any visible vessels. Any blood that extravasates is taken up in 15 second intervals using accurately weighed filter paper pieces, without touching the wound directly. Bleeding time is calculated as the time from making the incision to the point in time where no more blood can be detected on the filter paper. The volume of the extravasated blood is calculated after weighing of the filter paper pieces.

c) Determination of the Effect on Extravasation/Oedema Formation and/or Neovascularization in the Eve (In Vivo)

c.1) Test of the Efficacy of Substances in the Laser-Induced Choroidal Neovascularization Model This study serves to investigate the efficacy of a test substance on reduction of extravasation/oedema formation and/or choroidal neovascularization in the rat model of laser-induced choroidal neovascularization.

To this end, pigmented rats of the Brown-Norway strain not showing any signs of ophthalmic disorders are selected and randomized into treatment groups. On day 0, the animals are anaesthetized by intraperitoneal injection (15 mg/kg xylazine and 80 mg/kg ketamine). Following instillation of a drop of a 0.5% strength tropicamide solution to dilate the pupils, choroidal neovascularization is triggered on six defined locations around the optical nerve using a 532 nm argon laser photocoagulator (diameter 50-75 µm, intensity 150 mW, duration 100 ms). The test substance and the appropriate vehicle (e.g. PBS, isotonic saline) are administered either systemically by the oral or intraperitonal route, or topically to the eye by repeated administration as eye drops or intravitreal injection. The body weight of all the animals is determined before the start of the study, and then daily during the study.

On day 21, an angiography is carried out using a fluorescence fundus camera (e.g. Kowe, HRA). Under anaesthesia and after another pupil dilation, a 10% strength sodium fluorescein dye is injected subcutaneously (s.c.). 2-10 min later, pictures of the eye background are taken. The degree of extravasation/the oedema, represented by the leakage of fluorescein, is assessed by two to three blinded observers and classified into degrees of severity from 0 (no extravasation) to 3 (strong colouration exceeding the actual lesion).

The animals are sacrificed on day 23, after which the eyes are removed and fixated in 4% strength paraformaldehyde solution for one hour at room temperature. After one washing, the retina is carefully peeled off and the sclera-choroidea complex is stained using an FITC isolectin B4 antibody and then applied flat to a microscope slide. The preparations obtained in this manner are evaluated using a fluorescence microscope (Apotom, Zeiss) at an excitation wavelength of 488 nm. The area or volume of the choroidal neovascularization (in $\mu m^2$ and $\mu m^3$, respectively) is calculated by morphometric analysis using Axiovision 4.6 software.

c.2) Test of the Efficacy of Substances in the Oxygen-Induced Retinopathy Model

It has been shown that oxygen-induced retinopathy is a useful animal model for the study of pathological retinal angiogenesis. This model is based on the observation that hyperoxia during early postnatal development in the retina causes arrest or delay of the growth of normal retinal blood vessels. When, after a 7-day hyperoxia phase, the animals are returned to normoxic room air, this is equivalent to relative hypoxia since the retina is missing the normal vessels which are required to ensure adequate supply of the neural tissue under normoxic conditions. The ischaemic situation caused in this manner results in an abnormal neovascularization which has some similarities with pathophysiological neovascularization in eye disorders such as wet AMD. In addition, the neovascularization caused is highly reproducible, quantifiable and an important parameter for examining the disease mechanisms and possible treatments for various forms of retinal disorders.

The aim of this study is to examine the efficacy of daily systemically administered doses of the test compound on the growth of retinal vessels in the oxygen-induced retinopathy model. Neonates of C57Bl/6 mice and their mothers are exposed to hyperoxia (70% oxygen) on postnatal day 7 (PD7) for 5 days. From PD12, the mice are kept under normoxic conditions (room air, 21% oxygen) until PD17. From day 12 to day 17, the mice are treated daily with the test substance or the corresponding vehicle. On day 17, all mice are anaesthetized with isoflurane and then sacrificed by cervical fracture. The eyes are removed and fixated in 4% Formalin. After washing in phosphate-buffered saline, the retina is excised, a flat preparation thereof is produced and this is stained with isolectin B4 antibody. Quantification of neovascularization is carried out using a Zeiss ApoTome.

C) Working Examples of Pharmaceutical Compositions

The substances according to the invention can be converted to pharmaceutical preparations as follows:

Tablet:
Composition:

100 mg of the compound of Example 1, 50 mg of lactose (monohydrate), 50 mg of maize starch, 10 mg of polyvinylpyrrolidone (PVP 25) (from BASF, Germany) and 2 mg of magnesium stearate.

Tablet weight 212 mg. Diameter 8 mm, radius of curvature 12 mm

Production:

The mixture of the compound of Example 1, lactose and starch is granulated with a 5% strength solution (m/m) of the PVP in water. After drying, the granules are mixed with the magnesium stearate for 5 min. This mixture is compressed in a conventional tabletting press (see above for format of the tablet).

Oral Suspension:
Composition:

1000 mg of the compound of Example 1, 1000 mg of ethanol (96%), 400 mg of Rhodigel (xanthan gum) (from FMC, USA) and 99 g of water.

10 ml of oral suspension correspond to a single dose of 100 mg of the compound of the invention.

Production:

The Rhodigel is suspended in ethanol, and the compound of Example 1 is added to the suspension. The water is added while stirring. The mixture is stirred for about 6 h until swelling of the Rhodigel is complete.

Solution or Suspension for Topical Administration to the Eve (Eye Drops):

A sterile pharmaceutical preparation for topical administration to the eye can be prepared by reconstituting a lyophilisate of the inventive compound in sterile saline. Suitable preservatives for such a solution or suspension are, for example, benzalkonium chloride, thiomersal or phenylmercury nitrate in a concentration range of from 0.001 to 1 percent by weight.

The invention claimed is:
1. A compound of the formula

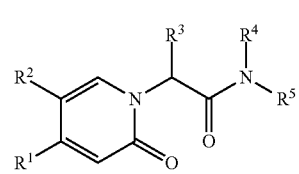

(I)

in which
$R^1$ represents a group of the formula

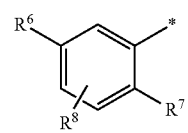

where * is the point of attachment to the oxopyridine ring,
$R^6$ represents bromine, chlorine, fluorine, methyl, difluoromethyl, trifluoromethyl, methoxy, difluoromethoxy or trifluoromethoxy, R⁷ represents bromine, chlorine, fluorine, cyano, nitro, hydroxy, methyl, difluoromethyl, trifluoromethyl, methoxy, ethoxy, difluoromethoxy, trifluoromethoxy, ethynyl, 3,3,3-trifluoroprop-1-yn-1-yl or cyclopropyl, R⁸ represents hydrogen, chlorine or fluorine, R² represents hydrogen, bromine, chlorine, fluorine, cyano, $C_1$-$C_3$-alkyl, difluoromethyl, trifluoromethyl, 1,1-difluoroethyl, 2,2-difluoroethyl, 2,2,2-trifluoroethyl, C1-C3-alkoxy, difluoromethoxy, trifluoromethoxy, 1,1-difluoroethoxy, 2,2-difluoroethoxy, 2,2,2-trifluoroethoxy, hydroxycarbonyl, methylcarbonyl or cyclopropyl, R³ represents hydrogen, $C_1$-$C_5$-alkyl, $C_1$-$C_4$-alkoxy, difluoromethyl, trifluoromethyl, 1,1-difluoroethyl, 3,3,3-trifluoro-2-hydroxyprop-1-yl, 3,3,3-trifluoro-2-methoxyprop-1-yl, 3,3,3-trifluoro-2-ethoxyprop-1-yl, prop-2-yn-1-yl, cyclopropyloxy or cyclobutyloxy, where alkyl may be substituted by a substituent selected from the group consisting of fluorine, cyano, hydroxy, difluoromethyl, trifluoromethyl, methoxy, ethoxy, difluoromethoxy, trifluoromethoxy, $C_3$-$C_6$-cycloalkyl, 4- to 6-membered oxoheterocyclyl, 1,4-dioxanyl, oxazolyl, phenyl and pyridyl, where cycloalkyl may be substituted by 1 to 2 substituents independently of one another selected from the group consisting of fluorine, hydroxy, methyl, ethyl, methoxy, ethoxy, difluoromethyl, trifluoromethyl, difluoromethoxy and trifluoromethoxy, R⁴ represents hydrogen, R⁵ represents a group of the formula

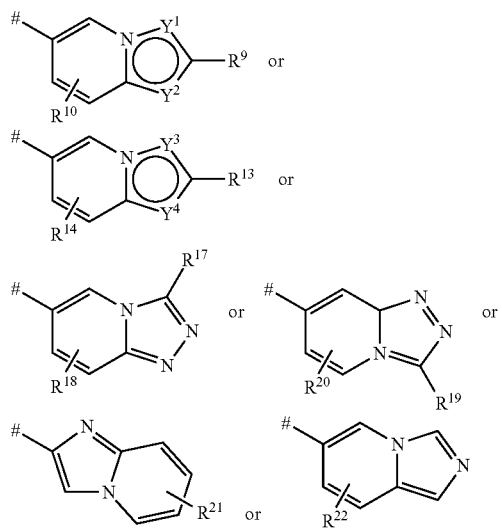

where # is the point of attachment to the nitrogen atom, $Y^1$ represents a nitrogen atom or C—$R^{11}$,
  where
    $R^{11}$ represents hydrogen, chlorine, hydroxy, methoxy or $C_1$-$C_3$-alkoxycarbonyl, $Y^2$ represents a nitrogen atom or C—$R^{12}$,
  where
    $R^{12}$ represents hydrogen, chlorine, hydroxy or methoxy, $R^9$ represents hydrogen, hydroxycarbonyl, hydroxycarbonylmethyl or phenyl, where phenyl may be substituted by 1 to 2 fluorine substituents, $R^{10}$ represents hydrogen, chlorine, fluorine or methyl, $Y^3$ represents a nitrogen atom or C—$R^{15}$,
  where
    $R^{15}$ represents hydrogen, chlorine, hydroxy or methoxy, $y^4$ represents a nitrogen atom or C—$R^{16}$,
  where
    $R^{16}$ represents hydrogen, chlorine, hydroxy or methoxy, $R^{13}$ represents hydrogen, hydroxycarbonyl, hydroxycarbonylmethyl, $C_1$-$C_3$-alkoxycarbonyl or aminocarbonyl, $R^{14}$ represents hydrogen, chlorine, fluorine or methyl, $R^{17}$ represents hydrogen, chlorine, hydroxy, $C_1$-$C_4$-alkyl, methoxy, $C_1$-$C_3$-alkylaminomethyl or morpholinylmethyl, $R^{18}$ represents hydrogen, chlorine, fluorine or methyl, $R^{19}$ represents hydrogen, chlorine, hydroxy or methoxy, $R^{20}$ represents hydrogen, chlorine, fluorine or methyl, $R^{21}$ represents hydrogen, hydroxycarbonyl or hydroxycarbonylmethyl, $R^{22}$ represents hydrogen, chlorine, fluorine or methyl, or one of the salts thereof, solvates thereof or solvates of the salts thereof.

2. The compound of claim 1, wherein
R¹ represents a group of the formula

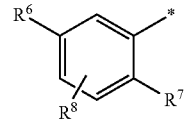

where * is the point of attachment to the oxopyridine ring,

R⁶ represents chlorine,

R⁷ represents cyano, difluoromethyl, trifluoromethyl, difluoromethoxy or trifluoromethoxy, R⁸ represents hydrogen, R² represents chlorine, cyano, methoxy, ethoxy or difluoromethoxy, R³ represents hydrogen, methyl, ethyl, n-propyl, 2-methylprop-1-yl, n-butyl or ethoxy, where methyl may be substituted by a substituent selected from the group consisting of difluoromethyl, trifluoromethyl, cyclopropyl, cyclobutyl, cyclohexyl, oxetanyl, tetrahydrofuranyl, tetrahydro-2H-pyranyl and 1,4-dioxanyl, where cyclopropyl, cyclobutyl, cyclohexyl and oxetanyl may be substituted by 1 to 2 substituents independently of one another selected from the group consisting of fluorine, hydroxy, methyl, ethyl and methoxy, and
  where ethyl, n-propyl and n-butyl may be substituted by a substituent selected from the group consisting of fluorine, methoxy and trifluoromethoxy, R⁴ represents hydrogen, R⁵ represents a group of the formula

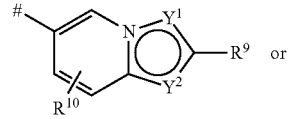

-continued

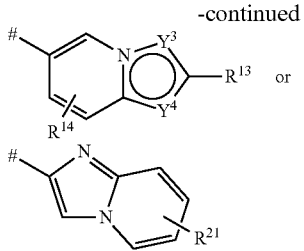

where # is the point of attachment to the nitrogen atom,
$Y^1$ represents a nitrogen atom or $C-R^{11}$,
  where
    $R^{11}$ represents hydrogen, chlorine, hydroxy or methoxy,
$Y^2$ represents a nitrogen atom or $C-R^{12}$,
  where
    $R^{12}$ represents hydrogen, chlorine, hydroxy or methoxy,
$R^9$ represents hydrogen or hydroxycarbonyl,
$R^{10}$ represents hydrogen or fluorine,
$Y^3$ represents a nitrogen atom or $C-R^{15}$,
  where
    $R^{15}$ represents hydrogen, chlorine, hydroxy or methoxy,
$Y^4$ represents a nitrogen atom or $C-R^{16}$,
  where
    $R^{16}$ represents hydrogen, chlorine, hydroxy or methoxy,
$R^{13}$ represents hydrogen or hydroxycarbonyl,
$R^{14}$ represents hydrogen or fluorine,
$R^{21}$ represents hydrogen or hydroxycarbonyl,
or one of the salts thereof, solvates thereof or solvates of the salts thereof.

3. The compound of claim 1, wherein
$R^1$ represents a group of the formula

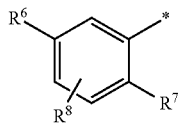

where * is the point of attachment to the oxopyridine ring,
$R^6$ represents chlorine,
$R^7$ represents cyano or difluoromethoxy,
$R^8$ represents hydrogen,
$R^2$ represents methoxy,
$R^3$ represents methyl or ethyl
  where methyl may be substituted by a substituent selected from the group consisting of cyclobutyl and tetrahydro-2H-pyranyl,
  and
  where ethyl may be substituted by a methoxy substituent,
$R^4$ represents hydrogen,
$R^5$ represents a group of the formula

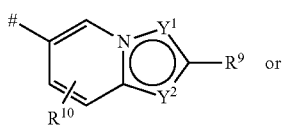

or

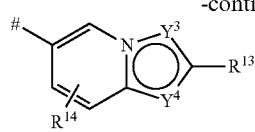

where # is the point of attachment to the nitrogen atom,
$Y^1$ represents $C-R^{11}$,
  where
    $R^{11}$ represents hydrogen or chlorine,
$Y^2$ represents a nitrogen atom,
$R^9$ represents hydrogen or hydroxycarbonyl,
$R^{10}$ represents hydrogen,
$Y^3$ represents a nitrogen atom,
and
$Y^4$ represents $C-R^{16}$,
  where
    $R^{16}$ represents hydrogen,
or
$Y^3$ represents $C-R^{15}$,
  where
    $R^{15}$ represents hydrogen or chlorine,
and
$Y^4$ represents a nitrogen atom,
$R^{13}$ represents hydrogen or hydroxycarbonyl,
$R^{14}$ represents hydrogen,
or one of the salts thereof, solvates thereof or solvates of the salts thereof.

4. A method of making the compound of claim 1 of the formula (I), or one of the salts thereof, solvates thereof or solvates of the salts thereof, characterized in that either
  [A] a compound of the formula

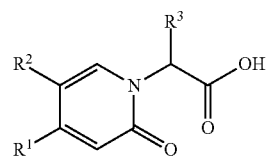
(II)

in which
$R^1$, $R^2$ and $R^3$ are each as defined in claim 1,
is reacted in the first step with a compound of the formula

(III)

in which
$R^4$ and $R^5$ are each as defined in claim 1,
in the presence of a dehydrating agent, and
optionally in a second step converted by acidic or basic ester hydrolysis into a compound of the formula (I),
or
[B] a compound of the formula

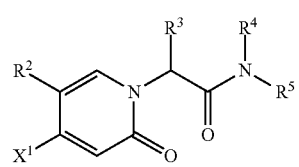
(IV)

in which $R^2$, $R^3$, $R^4$ and $R^5$ have the meaning given in claim 1, and $X^1$ represents chlorine, bromine or iodine, is reacted with a compound of the formula $$R^1\text{-}Q \qquad (V)$$

in which $R^1$ has the meaning given in claim 1, and

Q represents —B(OH)$_2$, a boronic ester, preferably boronic acid pinacol ester, or —BF$_3^-$K$^+$, under Suzuki coupling conditions to give a compound of the formula (I).

5. A medicament comprising the compound of claim 1 in combination with an inert, nontoxic, pharmaceutically suitable excipient.

6. A medicament for the treatment of thrombotic or thromboembolic disorders comprising the compound of claim 1 in combination with an inert, nontoxic, pharmaceutically suitable excipient.

7. A method for the treatment of thrombotic or thromboembolic disorders comprising administering an effective amount of the compound of claim 1.

8. A method for combating thrombotic or thromboembolic disorders comprising administering a therapeutically effective amount of the compound of claim 1.

9. A method for treating thrombotic or thromboembolic disorders comprising administering an effective amount of the medicament of claim 5.

* * * * *